United States Patent
Koussa et al.

(10) Patent No.: US 11,353,423 B2
(45) Date of Patent: Jun. 7, 2022

(54) ELECTROPHORESIS DIAGNOSTIC METHODS AND KITS

(71) Applicant: Vital Biosciences, Inc., Kitchener (CA)

(72) Inventors: Mounir A. Koussa, Kitchener (CA); Andrew Ward, Everett, MA (US); Padric Garden, Charlestown, MA (US); Anthony Pulido, Charlestown, MA (US); Bradley Demarco, Charlestown, MA (US); Christopher Blanchard, Charlestown, MA (US); ArunRichard Chandrasekaran, Charlestown, MA (US); Joshua Forman, Winchester, MA (US); Lisa Caldwell, Charlestown, MA (US)

(73) Assignee: Vital Biosciences, Inc., Kitchener (CA)

( * ) Notice: Subject to any disclaimer, the term of this patent is extended or adjusted under 35 U.S.C. 154(b) by 379 days.

(21) Appl. No.: 16/468,479

(22) PCT Filed: Dec. 22, 2017

(86) PCT No.: PCT/US2017/068302
§ 371 (c)(1),
(2) Date: Jun. 11, 2019

(87) PCT Pub. No.: WO2018/119437
PCT Pub. Date: Jun. 28, 2018

(65) Prior Publication Data
US 2020/0150083 A1    May 14, 2020

Related U.S. Application Data

(60) Provisional application No. 62/438,583, filed on Dec. 23, 2016.

(51) Int. Cl.
| | |
|---|---|
| G01N 27/447 | (2006.01) |
| C12P 19/34 | (2006.01) |
| C12Q 1/6811 | (2018.01) |

(52) U.S. Cl.
CPC ........ *G01N 27/44726* (2013.01); *C12P 19/34* (2013.01); *C12Q 1/6811* (2013.01)

(58) Field of Classification Search
None
See application file for complete search history.

(56) References Cited

U.S. PATENT DOCUMENTS

| 2008/0124752 A1 | 5/2008 | Ryals et al. |
| 2010/0275282 A1 | 10/2010 | Round et al. |

(Continued)

FOREIGN PATENT DOCUMENTS

| WO | WO 2013/067489 A1 | 5/2013 |
| WO | WO 2015/006626 A1 | 1/2015 |

(Continued)

OTHER PUBLICATIONS

Hansen, et al., "Nanoswitch-linked immunosorbent assay (NLISA) for fast, sensitive, and specific protein detection," PNAS Early Edition, 2017, pp. 1-6.

(Continued)

*Primary Examiner* — J. Christopher Ball
(74) *Attorney, Agent, or Firm* — Morgan, Lewis & Bockius LLP

(57) ABSTRACT

The invention described herein provides, in part, improved methods, compositions, and kits for detecting analytes in biological samples.

29 Claims, 45 Drawing Sheets

Specification includes a Sequence Listing.

(56) References Cited

U.S. PATENT DOCUMENTS

2014/0255939 A1   9/2014   Wong et al.
2016/0279257 A1   9/2016   Koussa et al.

FOREIGN PATENT DOCUMENTS

| WO | WO 2016/089588 A1 | 6/2016 |
| WO | WO 2016089588 A1 | 6/2016 |
| WO | WO 2017/003950 A2 | 1/2017 |
| WO | WO 2017003950 A2 | 1/2017 |
| WO | WO 2017/139409 A1 | 8/2017 |
| WO | WO 2017/165585 A1 | 9/2017 |
| WO | WO 2018/023088 A1 | 2/2018 |

OTHER PUBLICATIONS

Koussa, et al., "DNA nanoswitches a quantative platform for gel-based biomolecular interaction analysis," Nature Methods, 2014, 30 pages.
Koussa, et al., "Protocol for sortase-mediated construction of DNA-protein hybrids and functional nanostructures," Methods, 67(2), 2014, 20 pages.
Chai, et al., "A reversible fluorescence nanoswitch based on carbon quantum dots nanoassembly for detection of pyrophosphate ion," Sensors and Actuators B 220 (2015), pp. 138-145.
International Search Report & Written Opinion PCT Application No. PCT/US17/68302, dated Jun. 18, 2018, 11 pages.

A.

0.7% Agarose Gel in 0.5x TBE, 200V for 30 min, PMT 500
NS: C22, HA Crude and Purified Urine, Incubated 4 Hours

B.

1. NTA (Fully Deprotonated)

2. EDTA (Fully Deprotonated)

3. EGTA (Fully Deprotonated)

4. BAPTA (Fully Deprotonated)

A.

0.5X TBE, 200V 23min SYBR Prestained, PMT500h50

B.

0.5X TBE, SYBR Pre-Stain, 200V 20mins, PMT600h50

A.

B.

1. Gel Electrophoresis

2. Fraction Loop Yield

C.

1. Gel Electrophoresis
2. Fraction Loop Yield

D.

1. Gel Electrophoresis
2. Fractional Loop Yield

A.

| Conjugate | Yield (nM) |
|---|---|
| 2601-D | 51 |
| 2603-6 | 103 |
| Poly-D | 36 |
| Poly-6 | 52 |

E.

F.

G.

H.

I.

J.

K.

L.

M.

N.

O.

QuickVue controls sent through zeba columns (in 0.02% Tween/PBS)

A.

B.

C.

D.

E.

A.

B.

5/8 inches above gel

3/8 inches above gel 0.7% Agarose Gel in TBE, 200V for 20 min, PMT 500
BioBio NS Incubated 15 mins 0.7% Agarose Gel in TBE, 40mA for 20 min, PMT 500
BioBio NS Incubated 15 mins Looped Unlooped

A

B

C.

E.

F.

| Time | % bound |
|---|---|
| 120 min | 0.00 |
| 60 min | 0.00 |
| 30 min | 22.10 |
| 15 min | 35.73 |
| 5 min | 44.94 |
| 0 min | 51.32 |

G.

"Key"

"Bridge"

|  | 1 | 2 | 3 | 4 | 5 | 6 | 7 | 8 | 9 |
|---|---|---|---|---|---|---|---|---|---|
| SA | − | + | + | − | + | + | + | + | OS Bio-bio +SA |
| Key/Bridge oligo | − | − | − | + | + | + | + | + | |
| Biotin | − | − | + | − | − | + | − | + | |

A. 30-nt key oligo

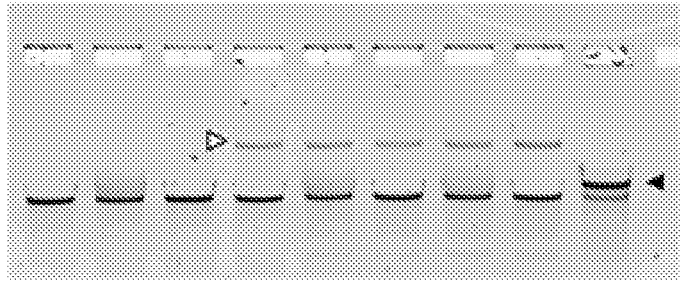

B. 20-nt key oligo

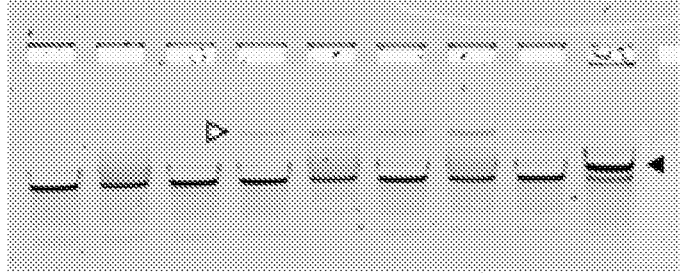

C. 40-nt bridge oligo

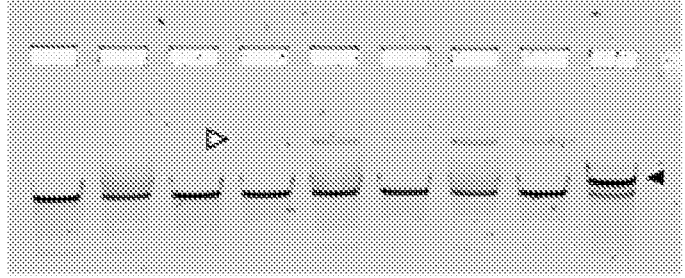

Reaction mixtures (followed table, done for A, B, C sets):

For 1-6:
    i. Added SA, RT for 15 mins
    ii. Added key/bride oligo and RT for 1 h
    iii. Added saturated biotin and RT for 1 h For 7-8:
    i. Added key/bride oligo and RT for 1 h
    ii. Added SA, RT for 15 mins
    iii. Added saturated biotin and RT for 1 h

- Final concentrations: NS conc: 80 pM, SA: 3 nM, key/bridge oligo: 1.25 nM

I.

B.

C.

A.

B.

A.

B.

C.

D.

E.

F.

G.

H.

I.

J.

K.

A

B

ELECTROPHORESIS DIAGNOSTIC METHODS AND KITS

CROSS-REFERENCE TO RELATED APPLICATIONS

This application is a U.S. National Stage under 35 U.S.C. 371 of international application No. PCT/US2017/068302, filed Dec. 22, 2017, which claims the benefit of priority to U.S. Provisional Application 62/438,583, filed Dec. 23, 2016, each of which is incorporated herein by reference in its entirety.

FIELD OF THE INVENTION

The application relates to methods, compositions, and kits for detecting analytes in biological samples.

BACKGROUND

The detection of analytes has various clinical and non-clinical applications in industries ranging from medicine, biological research, to environmental science and beyond. Traditional methods for analyte detection involve assays such as enzyme-linked immunosorbent assays (ELISA), mass spectrometry, and high pressure liquid chromatography (HPLC). While HPLC and mass spectrometry may be used to detect analytes on the basis of charge and/or size, ELISA may be used to detect an analyte based on antigens on the analyte that are recognizable by capture and detection agents (e.g., antibodies, aptamers, etc.). In particular, ELISA assay has become a relatively common detection method utilized in the life sciences. However, conventional ELISA may be time-consuming as it involves various incubation and washing steps and may not provide sufficient sensitivity for various applications. Further, the parameters for carrying out ELISA assays are highly variable thus rendering the assay difficult to develop as a universal platform, particularly as home diagnostics for individual users.

Accordingly, there remains a need for improved methods for detecting an analyte in a sample that takes less time and input to perform compared to conventional ELISA, while maintaining or improving the sensitivity of detection.

SUMMARY OF THE INVENTION

As described herein, the application is directed to nanoswitch compositions, methods of using and preparing the same, and kits that meet the needs in the art for improved methods for detecting analytes (or biomarkers) in a sample such as a bodily fluid or other sample derived from a subject or patient.

In an embodiment, the application is directed to a nanoswitch for detecting a biomarker (or an analyte). In some embodiments, the nanoswitch may include a nucleic acid scaffold (i.e., a scaffold nucleic acid) that is hybridized to one or more oligonucleotides. In some embodiments, the nanoswitch may include a set of binding partners configured to bind the biomarker, wherein the set of binding partners are linked to the nucleic acid scaffold or the one or more oligonucleotides and include a first binding partner and a second binding partner. The binding of the first binding partner and the second binding partner to a biomarker (or analyte) of interest may be sequential, or simultaneous, or in any order (e.g., first then second, second then first, first simultaneous with second, etc.). In some embodiments, a binding partner (e.g., a first or second binding partner) may be, for example, an antibody or an antigen. As described herein, binding of the biomarker by the set of binding partners causes the nucleic acid scaffold to form a loop. In some embodiments described herein, a loop refers to a looped nanoswitch that may be detectable by gel electrophoresis. In some embodiments, the loop may be a detectable loop that may be detected or quantified by one or more of the analytical methods described herein. In some embodiments, the loop may be detachable or undetachable, as described herein.

In an embodiment, the application is directed to a nanoswitch for detecting a biomarker (or an analyte) where, in some embodiments, the nanoswitch includes a nucleic acid scaffold that includes an M13 scaffold or a fragment thereof that may be hybridized to one or more oligonucleotides. In some embodiments, the nanoswitch may include a set of binding partners configured to bind the biomarker, wherein the set of binding partners are linked to the nucleic acid scaffold or the one or more oligonucleotides and include a first binding partner and a second binding partner.

In an embodiment, the application is directed to a nanoswitch for detecting a biomarker (or an analyte) where, in some embodiments, the nanoswitch includes a nucleic acid scaffold that includes single strand DNA that may be hybridized to one or more oligonucleotides, wherein the single strand DNA optionally includes p8064 single strand DNA. In some embodiments, the nanoswitch may include a set of binding partners configured to bind the biomarker, wherein the set of binding partners are linked to the nucleic acid scaffold or the one or more oligonucleotides and include a first binding partner and a second binding partner.

In an embodiment, the application is directed to a nanoswitch for detecting a biomarker (or an analyte) that may be considered a megaloop nanoswitch. In some embodiments, the nanoswitch includes a nucleic acid scaffold hybridized to one or more oligonucleotides. In some embodiments, the nanoswitch includes a set of binding partners configured to bind the biomarker, wherein the set of binding partners are linked to the nucleic acid scaffold or the one or more oligonucleotides and include a first binding partner and a second binding partner. In some embodiments, the nanoswitch includes a latch having latch oligonucleotides hybridized to the nucleic acid scaffold, wherein the latch oligonucleotides may include streptavidin, desthiobiotin, biotin, or a combination thereof.

In an embodiment, the application is directed to a nanoswitch for detecting a biomarker (or an analyte) that may be considered a megaloop nanoswitch. In some embodiments, the nanoswitch includes a nucleic acid scaffold hybridized to one or more oligonucleotides. In some embodiments, the nanoswitch includes a set of binding partners configured to bind the biomarker, wherein the set of binding partners are linked to the nucleic acid scaffold or the one or more oligonucleotides and include a first binding partner and a second binding partner. In some embodiments, the nanoswitch includes single strand extension oligonucleotides hybridized to the nucleic acid scaffold and configured to hybridize a key oligonucleotide.

In an embodiment, the application is directed to a nanoswitch for detecting a biomarker (or an analyte) that may be considered a megaloop nanoswitch. In some embodiments, the nanoswitch includes a nucleic acid scaffold hybridized to one or more oligonucleotides, wherein the nucleic acid scaffold includes at least two regions available to hybridize a bridge oligonucleotide. In some embodiments, the nanoswitch includes a set of binding partners configured to bind the biomarker, wherein the set of binding partners are linked to the nucleic acid scaffold or the one or more oligonucleotides and include a first binding partner and a second binding partner.

In an embodiment, the application is directed to a biomarker or analyte test system that may be configured to receive a sample and determine the presence of a biomarker or analyte in the sample. In some embodiments, the test system includes a case, a nanoswitch source disposed in the case including a nanoswitch as described herein that forms a loop in when binding the biomarker. In some embodiments, the test system includes a sample receiver (e.g., a sponge or porous element) connected to the case and configured to receive sample. In some embodiments, the test system includes an electrophoretic medium (e.g., a gel electrophoresis medium) disposed in the case and connected to the nanoswitch source and the sample receiver. In some embodiments, the test system includes an electrophoretic medium (e.g., a gel electrophoresis medium) disposed in the case in fluid communication with the nanoswitch source and the sample receiver.

In an embodiment, the application is directed to a method of preparing a nanoswitch as described herein. In some embodiments, the method includes the step of preparing the nucleic acid scaffold. In some embodiments, the method includes the step of coupling an oligonucleotide to the nucleic acid scaffold. In some embodiments, the method includes the step of functionalizing one or more of the nucleic acid scaffold and the oligonucleotide with a set of binding partners.

In an embodiment, the application is directed to a method of preparing a nanoswitch as described herein. In some embodiments, the method includes the step of preparing the nucleic acid scaffold. In some embodiments, the method includes the step of functionalizing an oligonucleotide with a set of binding partners to provide a functionalized oligonucleotide. In some embodiments, the method includes the step of coupling the functionalized oligonucleotide to the nucleic acid scaffold.

In an embodiment, the application is directed to a method of detecting a biomarker (or an analyte) in a sample provided by a subject. In some embodiments, the method includes the step of contacting the sample with nanoswitches described herein to bind the biomarkers in the sample. In some embodiments, the method includes the step of separating the nanoswitches bound to the biomarkers in the sample from unbound nanoswitches by gel electrophoresis in an electrophoretic medium (e.g., a gel electrophoresis medium).

DETAILED DESCRIPTION OF THE INVENTION

The application is directed improved methods, compositions, and kits for detecting analytes, including, for example, detecting analytes and/or complex formation, monitoring binding interactions, measuring association and/or dissociation kinetics, and the like. In various embodiments, polymers (i.e., nanoswitches) may be used that change conformation upon analyte binding, and are then separated and distinguished from each other via gel electrophoresis. The improved methods may be performed at home, in a laboratory setting, or along with a high-throughput analyzer for medical or scientific applications. The methods described here may provide significant advantages including speed, sensitivity, and accuracy compared to prior art detection techniques. Further still, the methods described herein may be relatively inexpensive and easy to perform thereby offering a distinct advantage for use as home diagnostics.

Basic Nanoswitch Approach

In various embodiments, the application relates to a nanoswitch-based detection of an analyte including, for example, detecting analytes and/or complex formation, monitoring binding interactions, measuring association and/ or dissociation kinetics, and the like, as described herein and various means of improvement as described herein.

Figure 26:
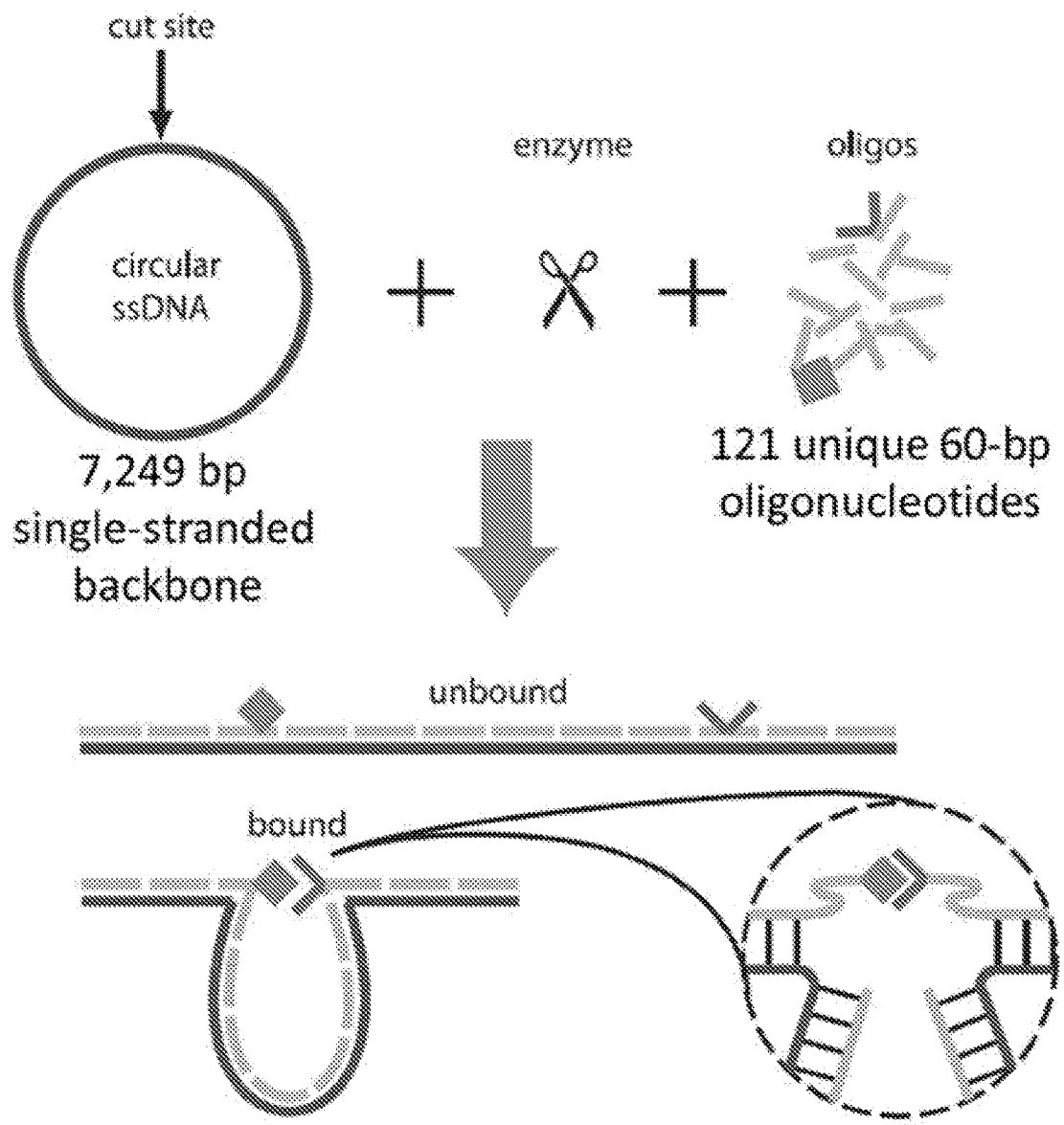
FIG. 26 provides an illustration of an exemplary nanoswitch (NS) synthesis and method of use.

FIG. 26 provides an illustration of exemplary nanoswitch (NS) synthesis and method of use. For example, in some embodiments, DNA nanoswitches may be made by hybridizing one or more oligonucleotides to a longer scaffold nucleic acid, wherein at least one such oligonucleotide is conjugated to a binding partner of an analyte of interest. In some embodiments, a plurality of oligonucleotides is hybridized to the scaffold. In other embodiments, the method described herein may be performed with a single oligonucleotide or with no oligonucleotide and simply conjugation of the binding partner to the scaffold itself. The use of hybridizing oligonucleotides facilitates specific positioning of the binding partner along the length of the scaffold. Further, use of the hybridizing oligonucleotides renders the nanoswitch technology more versatile and universal since a plurality of oligonucleotides may be created that differ with respect to the binding partners conjugated to them.

Various methods may be used to generate a nanoswitch as is known in the art. Exemplary methods are described for example, in WO 2013/067489, WO 2016/089588, and Koussa, et al. Nature Methods 12, 123-126 (2015), the entire contents of which are hereby incorporated by reference. In some embodiments, nanoswitches are generated by single-strand nicking of a double stranded nucleic acid, followed by hybridization to the nicked nucleic acid with one or more oligonucleotides conjugated to a binding partner of interest. The nicking action may be sequence-independent or sequence-dependent. The binding partners may be but are not limited to antibodies and antigen binding antibody fragments. The scaffold nucleic acid may be scaffold DNA such as linearized M13 DNA.

In the presence of an analyte of interest, the two binding partners of the nanoswitch bind to a single analyte thereby causing the nanoswitch to form a loop. In some embodiments, such loop formation requires the action of at least two binding partners. In other embodiments, nanoswitches described herein may comprise two or more binding partners, with each binding interaction involving two or more binding partners rendering a different conformation that can be distinguished from other conformations using gel electrophoresis. In some embodiments involving multiple binding partners, a loop is formed when only one pair of binding partner bind to a single analyte. In still other embodiments, the method may involve two physically separate polymers such as two physically separate nucleic acids, each conjugated to a binding partner, and in the presence of the analyte the two binding partners bind to the analyte, thereby causing the physical interaction of the two polymers. The result is a complex comprising the two polymers joined together via a common analyte and at two binding partners to such analyte.

In various embodiments, the resulting mixture is run on a gel, such as an agarose gel, and imaged so as to distinguish the nanoswitches with different conformations.

In various embodiments, the invention described herein relates to an improved method for analyte detection of an analyte including, for example, detecting analytes and/or complex formation, monitoring binding interactions, measuring association and/or dissociation kinetics, and the like, by placing a nucleic acid complex, which comprises a single-stranded scaffold nucleic acid hybridized to one or more single-stranded oligonucleotides, where a first single-stranded oligonucleotide is linked to a first binding partner and a second single-stranded oligonucleotide in the plurality is linked to a second binding partner, under conditions that allow for binding of binding partners to each other, and detecting a change in the nucleic acid complex using gel electrophoresis, e.g. a change in the apparent length of the nucleic acid complex as determined from migration through a gel when binding between the partners occurs as compared to the absence of binding (e.g. a change in migration distance as the result of a change in nucleic acid topology, e.g. detecting the presence or absence of a looped structure, e.g. a looped linker structure, being formed when binding between the partners occurs, e.g. comparing a looped structure (indicating that binding between the partners occurred) to a linear structure (indicating that binding between the partners has not occurred) and observing a "gel shift"). In various embodiments, the binding partners may be entities that measurably interact with each other, e.g. an antibody (or functional fragment thereof, e.g. containing a relevant paratope) and an antigen (or epitope-containing fragment thereof), a receptor and a ligand, etc. In various embodiments, either of the binding partners may be an analyte for which detection is desired. For example, in various embodiments, the analyte for which detection is desired is an antigen (or epitope-containing fragment thereof) that is recognized by an antibody (or functional fragment thereof, e.g. containing a relevant paratope).

Throughout the disclosure, various improvements of the nanoswitch methods and compositions are provided. Such improvements are separate embodiments described herein, but also may be combined to perform the methods or make the compositions (e.g. this disclosure envisions using the various improvements individually or in combination).

Improvements Related to Nanoswitches

In various embodiments, the nanoswitches comprise a scaffold or backbone nucleic acid comprising one or more binding partners. The scaffold nucleic acid may be of any length sufficient to allow association and dissociation of binding partners to occur, to be detected, and to be distinguished from other events. In some embodiments, the scaffold nucleic acid is at least about 100 nucleotides in length. In some embodiments, the scaffold nucleic acid is about 100 to about 200,000 nucleotides in length. For example, the scaffold nucleic acid may be about 100, about 200, about 300, about 400, about 500, about 600, about 700, about 800, about 900, about 1,000, about 2,000, about 3,000, about 4,000, about 5,000, about 6,000, about 7,000, about 8,000, about 9,000, about 10,000, about 11,000, about 12,000, about 13,000, about 14,000, about 15,000, about 16,000, about 17,000, about 18,000, about 19,000, about 20,000, about 30,000, about 40,000, about 50,000, about 60,000, about 70,000, about 80,000, about 90,000, about 100,000, about 125,000, about 150,000, about 175,000, or about 200,000 nucleotides in length. In some embodiments, the scaffold nucleic acid may be greater than about 100, about 200, about 300, about 400, about 500, about 600, about 700, about 800, about 900, about 1,000, about 2,000, about 3,000, about 4,000, about 5,000, about 6,000, about 7,000, about 8,000, about 9,000, about 10,000, about 11,000, about 12,000, about 13,000, about 14,000, about 15,000, about 16,000, about 17,000, about 18,000, about 19,000, about 20,000, about 30,000, about 40,000, about 50,000, about 60,000, about 70,000, about 80,000, about 90,000, about 100,000, about 125,000, about 150,000, about 175,000, or about 200,000 nucleotides in length. In some embodiments, the scaffold nucleic acid may be less than about 100, about 200, about 300, about 400, about 500, about 600, about 700, about 800, about 900, about 1,000, about 2,000, about 3,000, about 4,000, about 5,000, about 6,000, about 7,000, about 8,000, about 9,000, about 10,000, about 11,000, about 12,000, about 13,000, about 14,000, about 15,000, about 16,000, about 17,000, about 18,000, about 19,000, about 20,000, about 30,000, about 40,000, about 50,000, about 60,000, about 70,000, about 80,000, about 90,000, about 100,000, about 125,000, about 150,000, about 175,000, or about 200,000 nucleotides in length.

In some embodiments, the scaffold nucleic acid may be a naturally occurring nucleic acid. In an embodiment, the scaffold nucleic acid comprises a M13 scaffold such as M13mp18. The M13 scaffolds are disclosed by Rothemund (2006) Nature 440:297-302, the entire contents of which are hereby incorporated by reference. In an embodiment, the scaffold nucleic acid may be lambda DNA. In other embodiments, the scaffold nucleic acid may also be non-natural or synthetic nucleic acids such as polymerase chain reaction (PCR)-generated nucleic acids, rolling circle amplification (RCA)-generated nucleic acids, etc.

In some embodiments, the binding partners are positioned along the scaffold nucleic acid to yield loops and thus length changes that are detectable (for example, by gel electrophoresis). The scaffold may be at least partially or fully single-stranded, or at least partially or fully double-stranded, or at least partially or fully triple-stranded, or at least partially or fully quadruple-stranded, or more (e.g., comprising at least five strands, six strands, seven strands, eight strands, nine strands, or ten strands, or more). The complex may comprise varying lengths of double-stranded regions. The scaffold nucleic acid may comprise DNA, RNA, DNA analogs, RNA analogs, or a combination thereof. In some embodiments, the binding partners are conjugated to a scaffold nucleic acid via hybridization of oligonucleotides to the scaffold, wherein such oligonucleotides are themselves conjugated to a binding partner. In an embodiment, the scaffold nucleic acid is a DNA.

In some embodiments, the scaffold nucleic acid may be hybridized to one, two, or more, including a plurality, of oligonucleotides. Each of the plurality of oligonucleotides may hybridize to the scaffold nucleic acid in a sequence-specific and non-overlapping manner (i.e., each oligonucleotide hybridizes to a distinct sequence in the scaffold). In other embodiments, the plurality of oligonucleotides may hybridize to the scaffold nucleic acid in a sequence-specific and overlapping manner (e.g., so as to allow certain oligonucleotides to peel off). The number of oligonucleotides hybridized to a particular scaffold may vary depending on the application. In various embodiments, there may be about 2 or more oligonucleotides hybridized to the scaffold, including about 3, about 4, about 5, about 6, about 7, about 8, about 9, about 10, about 20, about 30, about 40, about 50, about 60, about 70, about 80, about 90, about 100, about 200, about 300, about 400, about 500, about 600, about 700, about 800, about 900, or about 1000 or more oligonucleotides.

In some embodiments, the one or more oligonucleotides hybridized to the scaffold nucleic acid are unmodified. Unmodified oligonucleotides include oligonucleotides that are not linked to binding partners such as binding partners being tested (e.g., an antibody or an antigen). In other embodiments, the one or more oligonucleotides hybridized to the scaffold are modified. Modified oligonucleotides include those that are linked to binding partners being tested (e.g., a receptor and/or its ligand, an antibody and/or its antigen, etc.). Modified oligonucleotides may also include those that are modified and thus used to immobilize the nanoswitch to a solid support such as but not limited to a bead. Such modified oligonucleotides include, for example, biotinylated oligonucleotides or oligonucleotides modified with any of the tags described herein. Modified oligonucleotides may be referred to herein as "variable" or "functionalized" oligonucleotides since these oligonucleotides may be modified by linking to a variety of binding partners depending on the method of use.

Regions comprising scaffold hybridized to modified oligonucleotides may be referred to herein as "variable" regions and the remaining scaffold regions may be referred to as "fixed" regions.

The scaffold-binding partner construct may be made in a number of ways including through nicking of a double stranded nucleic acid to which binding partners are conjugated (to one strand), or by hybridization of one or more oligonucleotides to the scaffold, as described herein. In some embodiments, the binding partners may be conjugated to the scaffold nucleic acid itself rather than to an oligonucleotide that is hybridized to the scaffold.

The spacing of binding partners, and thus in some instances of the modified (or variable) oligonucleotides, along the length of the scaffold nucleic acid may vary. In some embodiments, the nanoswitch may comprise about 2, 3, or 4, or more binding partners. In some embodiments, the nanoswitch may comprise about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 250, about 300, about 350, about 400, about 450, or about 500, or more binding partners. As an example, a nucleic acid nanoswitch may comprise two internal modified oligonucleotides. The modified oligonucleotides internal to the nanoswitch may be linked individually to members of a binding pair (i.e., each of the two oligonucleotides is linked to a member of the binding pair such that the nanoswitch comprises the binding pair, with each member of the pair on a different oligonucleotide). The internal modified oligonucleotides may be symmetrically or quasi-symmetrically located around the center of the scaffold. In other words, they may be positioned equi-distant from the center of the scaffold. In some embodiments, the distance between the binding pair members may be about 100 to about 200,000 base pairs in length. For example, the distance between the binding pair members may be about 100, about 200, about 300, about 400, about 500, about 600, about 700, about 800, about 900, about 1,000, about 2,000, about 3,000, about 4,000, about 5,000, about 6,000, about 7,000, about 8,000, about 9,000, about 10,000, about 11,000, about 12,000, about 13,000, about 14,000, about 15,000, about 16,000, about 17,000, about 18,000, about 19,000, about 20,000, about 30,000, about 40,000, about 50,000, about 60,000, about 70,000, about 80,000, about 90,000, about 100,000, about 125,000, about 150,000, about 175,000, or about 200,000 base pairs in length.

In various embodiments, the distance between the binding partners is used to distinguish association and dissociation between binding partners linked to the nanoswitches. This is because when the binding partners are associated with each other, a loop will be formed comprising the nucleic acid sequence that exists between the binding partners. When the binding partners are not associated to each other (i.e., unbound), then the loop does not form and the complex length is different (e.g., longer). In some embodiments, the invention described herein comprises multiple binding partners as described herein, and a loop is formed when at least one pair of binding partners bind to a single analyte. The nanoswitch configuration can be determined by analyzing the migration of the nanoswitch through a matrix such as a gel in a gel electrophoretic system. The unbound, linear form travels more rapidly than does the bound, looped form. Thus, in various embodiments, presence of an analyte of interest, to which the binding partners on a single nanoswitch bind, will trigger the formation of a bound and looped nanoswitch. In various embodiments, the bound, looped nanoswitch will be distinguished from its unbound, linear counterpart based on the difference in their migration distances through a gel or other pore-containing matrix. The invention described herein contemplates different variations on the nucleic acid nanoswitches described herein. In various embodiments, these variations commonly comprise a nucleic acid nanoswitch having two or more binding partners. The binding partners typically have binding specificity for a common analyte. Methods described herein rely on the association and/or dissociation of binding partners. A change in conformation of the nanoswitch (e.g., from an open to a closed conformation) provides information about the presence of the analyte. The binding partners may be non-covalently or covalently bound to the scaffold.

In some embodiments, the nucleic acid complex comprises two binding partners having binding specificity for a common analyte. The binding partners are physically separate and thus spaced apart from each other (when not bound to the common analyte). When bound to the common analyte, the nucleic acid nanoswitch assumes a looped (or closed or bound) conformation having a different conformation and thus a different "apparent" length (as for example measured using migration through a gel electrophoresis system), compared to the nucleic acid nanoswitch in an open (or unbound) conformation.

In other embodiments, the invention further contemplates a nucleic nanoswitch comprising more than two conjugated binding partners. The number of binding partners may be about 2, about 3, about 4, or more. In some embodiments, pairs of binding partners are provided, with each pair having binding specificity for a particular analyte. A single nanoswitch may comprise a binding pair for a first analyte, which may be a test analyte, and a second binding pair for a second analyte, which may be a control analyte. In this way, the nanoswitch may have a control reading as well as a test reading. For example, a first binding pair may bind to a marker of interest and a second binding pair may bind to a control protein or other moiety that will always be present in the sample being tested (e.g., the urine) in order to establish to the end user that a sufficient quantity of sample was applied to the system. The location or arrangement of the binding partners may vary and may include serially positioned binding pairs or nested binding pairs, or combinations thereof. Alternatively, the test and control analytes may be assayed using different nanoswitches that are nevertheless still run through the same gel system.

In various embodiments, the nanoswitches comprise binding partners such as, for example, an antibody or an antigen. The linkage between the nucleic acid and the binding partner may be covalent or noncovalent depending on the strength of binding required for a particular application. They may be generated by first incorporating a reactive group (or moiety) into the nucleic acid (or into an oligonucleotide hybridized to the nucleic acid), and then reacting this group (or moiety) with the binding partner of interest which may or may not be modified itself. Suitable reactive groups are known in the art. Examples of reactive groups that can covalently conjugate to other reactive groups (leading to an irreversible conjugation) include but are not limited to amine groups (which react to, for example, esters to produce amides), carboxylic acids, amides, carbonyls (such as aldehydes, ketones, acyl chlorides, carboxylic acids, esters and amides) and alcohols. Those of ordinary skill in the art will be familiar with other "covalent" reactive groups. Examples of reactive groups that non-covalently conjugate to other molecules (leading to a reversible conjugation) include biotin and avidin or streptavidin reactive groups (which react with each other), antibody (or antibody fragment) reactive groups and antigens, receptors and receptor ligands, aptamers and aptamer ligands, nucleic acids and their complements, and the like. Virtually any reactive group is amenable to the methods described herein, provided it participates in an interaction of sufficient affinity to prevent dissociation of the binding partner from the nucleic acid nanoswitch.

In various embodiments, multiple binding partners may be used including multiple antibodies (see Example 6 provided herein). In some embodiments, the methods described herein utilizes at least about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 250, about 300, about 350, about 400, about 450, or about 500 antibodies. In embodiments, the methods described herein utilizes at least about 2, about 3, about 4, about 5, about 6, about 7, about 8, about 9, about 10, about 11, about 12, about 13, about 14, about 15, about 16, about 17, about 18, about 19, about 20, about 25, about 30, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, or about 250 antibody pairs. In some embodiments, the antibodies are located in clusters of close groups so that all loop combinations run to a similar location in a gel. In other embodiments, the antibodies are not clustered in close groups. In such embodiments, a decrease of bands in a gel corresponding to linear conformations may be monitored instead of an increase of bands corresponding to looped conformations.

In some embodiments, methods described herein may involve coupling of multivalent antibodies. For example, the methods may involve coupling of bi-valent or trivalent single-chain variable fragment antibodies (e.g., each of which can contain about 4 or about 6 analyte, or more, binding sites, respectively). In other embodiments, methods described herein may involve chemically forming aggregates of multiple antibodies which can be coupled to a single oligonucleotide. This could be performed with a variety of multifunctional linkers.

It is contemplated that use of multiple binding partners allows for improvements in the speed and sensitivity of analyte detection. For example, in some embodiments, methods described herein significantly reduce incubation time (e.g., during low analyte detection assays). In some embodiments, methods described herein allow for incubation times of about 1 minute to about 60 minutes, e.g., about 10 minutes, about 15 minutes, about 20 minutes, about 25 minutes, or about 30 minutes. In some embodiments, use of multiple binding partners increase loop yields including maximum loop yields (e.g., so as to achieve a maximum loop yield of about 20%, about 30%, about 40%, about 50%, about 60%, about 70%, about 80%, about 90%, about 91%, about 92%, about 93%, about 94%, about 95%, about 96%, about 97%, about 98%, about 99%, or about 100%).

The production of DNA nanoswitches with multiple antibodies is one method for increasing detection limits of DNA nanoswitches. However, the purification of multiple antibodies in parallel can be time-consuming and expensive. In various embodiments, the invention described herein provides a pooling method for ensuring an equal-molar ratio of material as well as the separation of cross-reacting antibodies. In an embodiment, the method involves pooling of antibody-oligonucleotide as described in Example 7.

When using DNA nanoswitches that are functionalized with antibodies, a common problem that can occur is the formation of a DNA loop in the absence of the antigen. This is commonly referred to as a false positive signal. In various embodiments, methods described herein minimize such false positive signals. In some embodiments, the methods reduce signals by controlling solution pH. In some embodiments, the solution pH is controlled by the use of appropriate buffers, which can be specific for the antibodies used. In some embodiments, Tris/Borate/EDTA buffer and/or buffers with EDTA are utilized. Various buffers may be utilized in the invention described herein. Exemplary buffers that may be utilized for running gels in the invention described herein include, but are not limited to, single buffers systems such as Sodium Borate, Sodium Acetate, Sodium Citrate, Lithium Borate, Tris/Acetic Acid/EDTA, Tris/Acetic Acid, Tris-Acetate, Tris Acetate EDTA, Tris/TAPS/EDTA Buffer, Bis- Tris/HCl buffer, Tris-Acetate SDS, MOPS, MOPS/Tris/ SDS/EDTA, MOPS/Tris/EDTA, MOPS/Tris/SDS, MOPS/ Tris, MES, MES/Tris/SDS/EDTA, MES/Tris/EDTA, MES/ Tris/SDS, MES/Tris, Tris-glycine, or dual buffer systems such as Tris EDTA on one side and Boric Acid on the other side of the gel. Additional exemplary buffers that may be utilized for stabilizing pH include, but are not limited to, Sodium Borate, Sodium Acetate, Sodium Citrate, Lithium Borate, Tris-HCl, TAPS, Tris/Acetic Acid/EDTA, Tris-Acetate, Tris Acetate EDTA, Tris/TAPS/EDTA Buffer, Ammonium Bicarbonate, Sodium Bicarbonate, Phosphate buffer, Guanidine Hydrochloride, Guanidine Thiocyanate, Bis-Tris/ HCl buffer, Tris-Acetate SDS, MOPS, MOPS/Tris/EDTA, MOPS/Tris/SDS, MOPS/Tris, MES, MES/Tris/SDS/EDTA, MES/Tris/SDS, MES/Tris, and Tris-glycine.

In some embodiments, passivating agents such as Tween, BSA, poly ethylene glycol, or casein are used. Additional exemplary passivating agents that may be utilized in the invention described herein include, but are not limited to, Glycerol, Sucrose, Glucose, TritonX, SDS, LDS, Sigmacoat, DNA oligos, Fish Gelatin, Whole sera, Polyvinyl alcohol, polyvinylpyrrolidone, salmon-sperm DNA, Silanes, and Silica.

In various embodiments, the methods involve detecting low concentration of analyte. In such embodiments, the methods may involve use of increased concentrations of the nanoswitch in solution (thereby resulting in, for example, increased sensitivity and decrease in incubation time). In some embodiments, the methods may involve decreasing the loop size, and/or increasing the number of antibodies on the construct.

Figure 19:
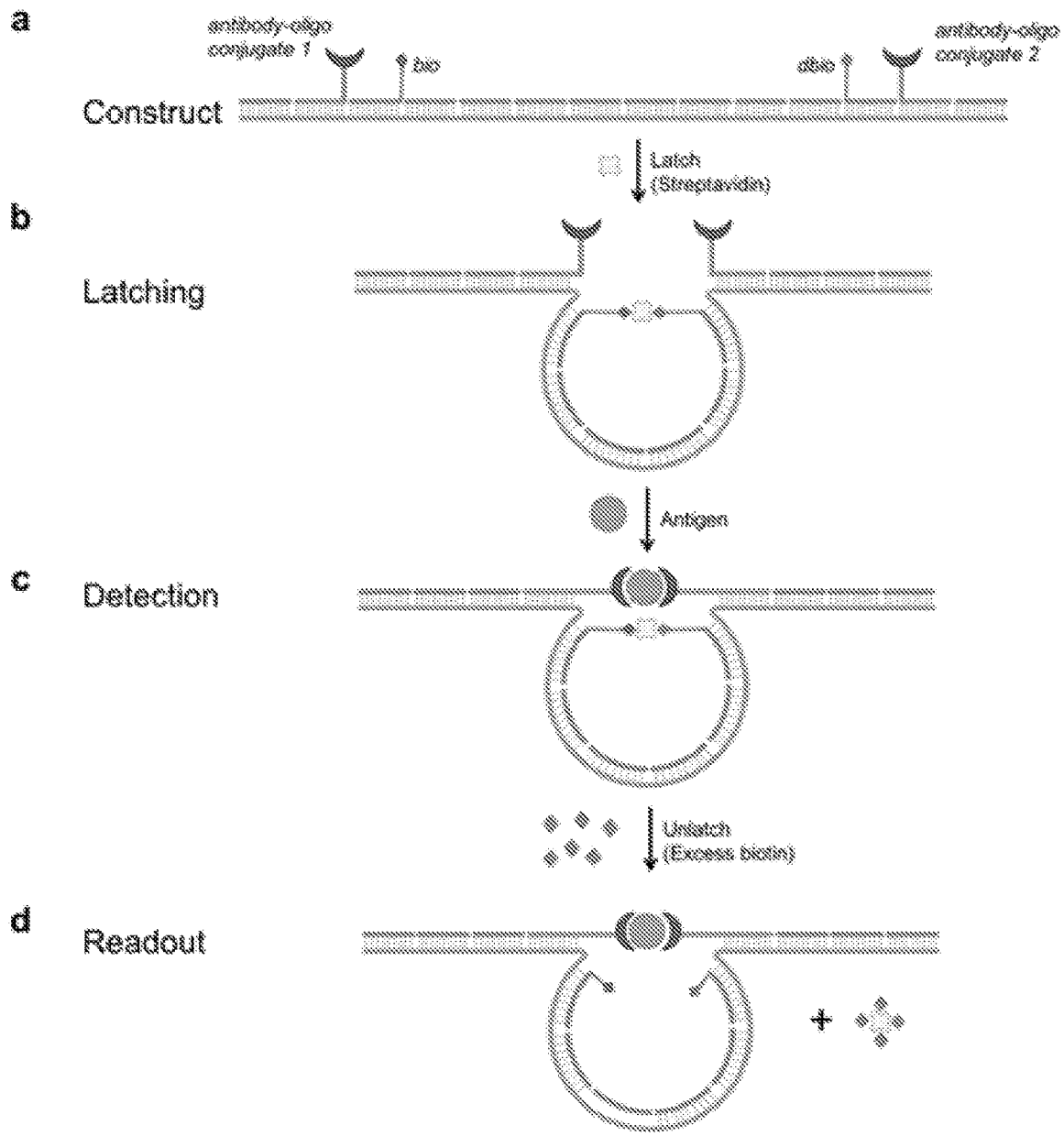
FIG. 19, panels A-D provide schematics of the megaloop design described in Example 6. Panel E shows the construction and testing of the latch. The gel shows loop formation tests at different concentrations of streptavidin. Panel F shows characterization of the off-rate for the biotin-SA-desthiobiotin latch. Panel G shows the design of megaloop using key and bridge oligonucleotides. Panel H shows a characterization of the megaloop using key and bridge oligonucleotides. Panel I shows a characterization of the megaloop with antigen-antibody interaction.
Figure 19:
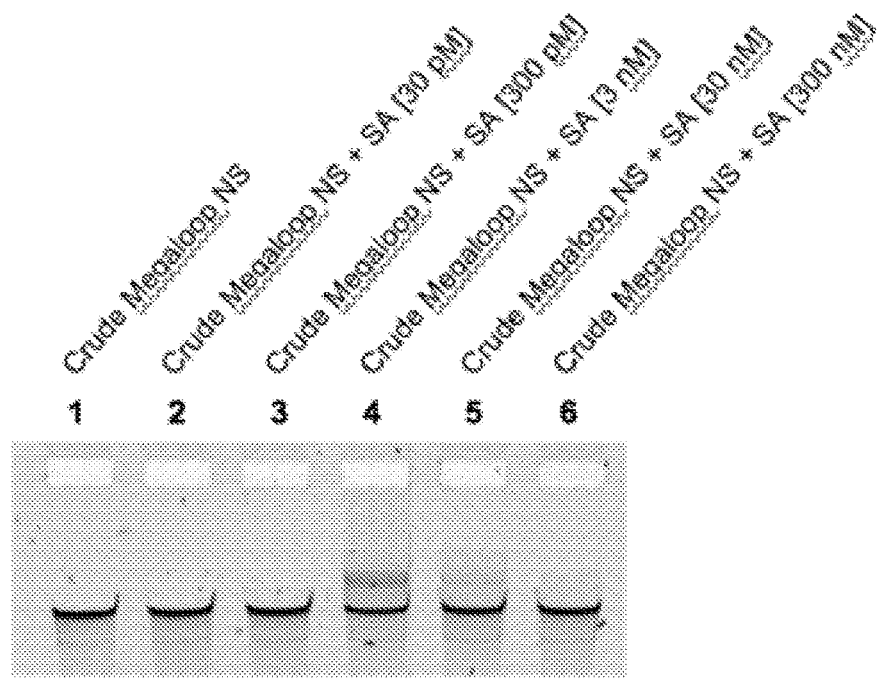
Figure 19:
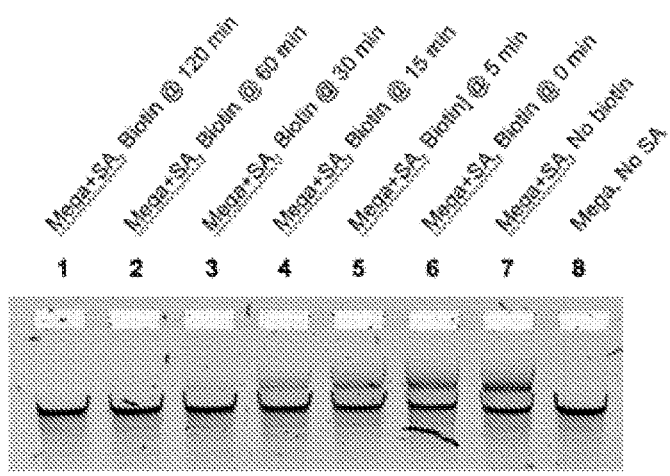
Figure 19:
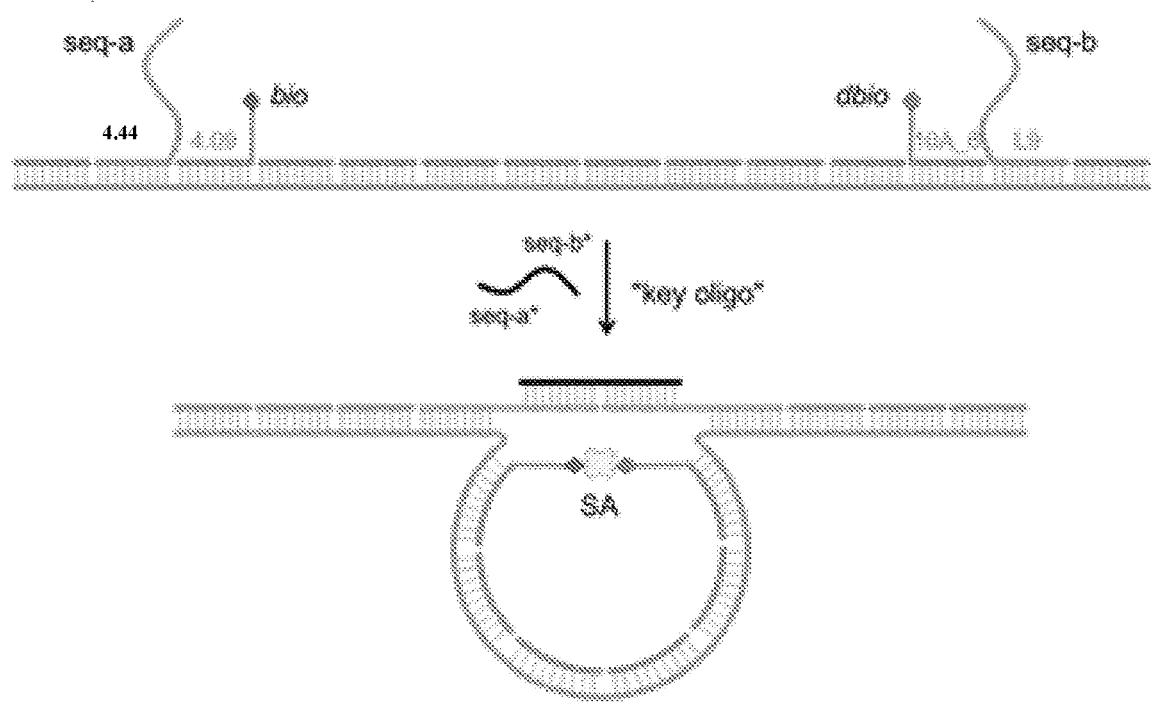
Figure 19:
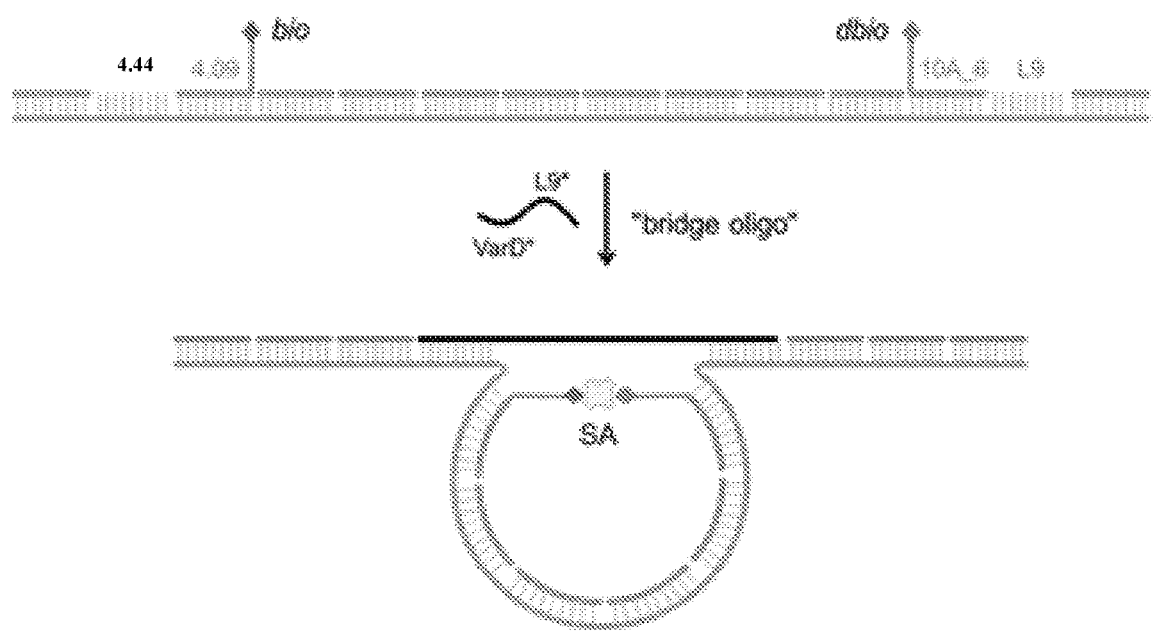
Figure 19:
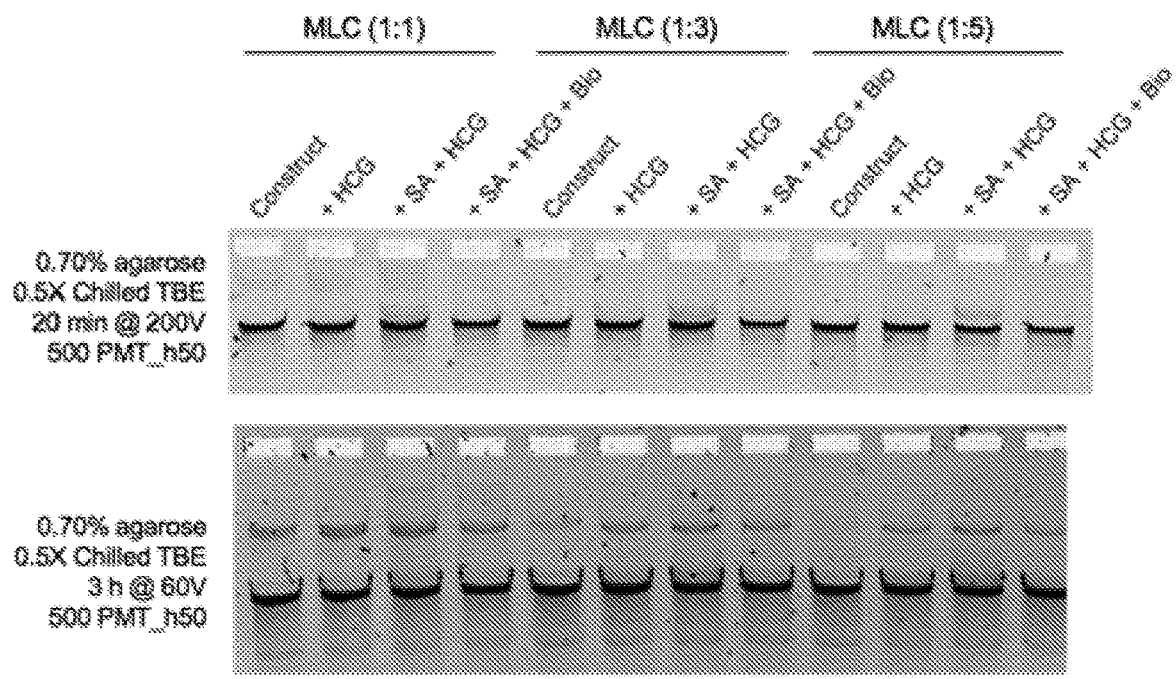

In various embodiments, the methods utilize a megaloop design (i.e., a loop with a latch as described in Example 6 and depicted in FIG. 19, panels A-D). Without wishing to be bound by any one theory of the invention, it is believed that the megaloop provides a larger loop size thus allowing for better separation between looped and linear bands. Additionally, use of megaloop involves formation of a latch that can increase local concentration of antibodies on the construct thereby increasing the amount of analyte bound in the looped geometry. The high local concentration also decreases the amount of DNA nanoswitches which have two analytes bound (capped). This is important for solutions which have very high concentrations of analyte. If the concentration of analyte is too high, the majority of DNA nanoswitches will be capped and unable to loop. Megaloop ensures the closest possible distance between functionalized oligos and thus significantly increases the highest concentration of detectable analyte. This strategy leads to improved sensitivity of detection and incubation times required for the read out. In some embodiments, the latch is made using streptavidin-desthiobiotin, streptavidin-biotin, DNA overhangs, or any other binding partner (e.g., one with revisable binding). In some embodiments, the megaloop is generated using "key" and bridge" oligonucleotides (as described in Example 6 and depicted in FIG. 19, panel G). In such embodiments, hybridization of either a "key" or a "bridge" oligonucleotide results in loop formation. Hybridization using a "key" oligonucleotide involves a megaloop construct with single-stranded extensions at locations where the antibody-oligo conjugate would be placed. Loop formation is achieved by the addition of a DNA strand ("key") whose sequence is partially complementary to the single-stranded extensions. Specifically, hybridization of this "key" oligonucleotide leads to loop formation. In some embodiments, the "key" oligonucleotide may be from about 1 to about 500 nucleotides in length. For example, the "key" oligonucleotide may be about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, about 100, about 125, about 150, about 175, about 200, about 225, about 250, about 275, about 300, about 325, about 350, about 375, about 400, about 425, about 450, about 475, or about 500 nucleotides in length. Hybridization using a "bridge" oligonucleotide involves a megaloop construct with single-stranded regions on the scaffold nucleic acid (e.g., M13) at locations where the antibody-oligo conjugate will be placed. In some embodiments, this is achieved by omitting specific backbone oligonucleotides that bind to those regions on the scaffold. Loop formation is induced by the addition of a DNA strand ("bridge") whose sequence is partially complementary to the single-stranded regions on the scaffold. Hybridization of this "bridge" oligonucleotide leads to loop formation. In some embodiments, the "bridge" oligonucleotide may be from about 1 to about 200 nucleotides in length. For example, the "bridge" oligonucleotide may be about 1, about 2, about 3, about 4, about 5, about 6, about 7, about 8, about 9, about 10, about 11, about 12, about 13, about 14, about 15, about 16, about 17, about 18, about 19, about 20, about 25, about 30, about 35, about 40, about 45, about 50, about 55, about 60, about 65, about 70, about 75, about 80, about 85, about 90, about 95, about 100, about 125, about 150, about 175, or about 200 nucleotides in length.

All phases of DNA nanoswitch construction require effective purification techniques. For example, purification techniques are particularly useful for the antibody conjugation step and/or the DNA nanoswitch hybridization step.

The purification of antibody conjugates from unconjugated oligonucleotides is important in DNA nanoswitch construction. Uncoupled oligonucleotides (also referred to as "oligos") can compete with the antibody-oligos when hybridizing onto the DNA scaffold. For example, unconjugated oligonucleotides can hybridize to a nanoswitch resulting in un-loopable nanoswitches. This leads to a drop in nanoswitch functionality.

In some embodiments, methods described herein utilize gel purification. In various embodiments, gel purification is utilized to extract and purify antibody-oligonucleotides conjugates and/or to remove uncoupled oligonucleotides. The purified antibody conjugate can then be used for hybridization to a DNA nanoswitch.

In some embodiments, the invention described herein provides methods for purifying conjugated oligonucleotides using protein G and/or protein A beads. Without wishing to be bound by theory, it is believed that the Protein G and Protein A bind to the Fc region of an antibody, allowing for removal of any oligonucleotides that lacks and antibody thus enriching the conjugated oligonucleotides. In other embodiments, beads coated with antigens (which would also bind to the antibody) may be used. In further embodiments, a small molecule or protein tag may be added to the antibody which could be bound by the beads.

Purification is also important for the DNA nanoswitch hybridization step. In order to improve (e.g. maximize) the hybridization efficiency of the antibody-oligo conjugate, in some embodiments, the antibody-oligo conjugate is added in vast excess to the DNA nanoswitch. This leaves unhybridized antibody in the solution which can compete with the DNA nanoswitch for analyte binding. In various embodiments, the ratio of antibody-oligo conjugates to DNA nanoswitch used for hybridization may be at least about 1, about 2, about 3, about 4, about 5, about 10, about 11, about 12, about 13, about 14, about 15, about 16, about 17, about 18, about 19, about 20, about 25, about 30, about 40, about 50, about 60, about 70, about 80, about 90, or about 100 antibody-oligo conjugates per DNA nanoswitch. Removal of these excess oligos is especially important when detecting analyte at low concentrations because high concentrations of DNA nanoswitch are needed.

In some embodiments, gel purification is used to purify excess antibody (e.g., unhybridized antibody) which runs lower than the DNA nanoswitch. In some embodiments, gel purification is also used to remove un-hybridized backbone oligos which fill in the single stranded DNA scaffold to make it fully double stranded. Without wishing to be bound by theory, it is believed that this has the additional benefit of leading to sharper DNA bands, and improved quality. This is because when running DNA nanoswitch in a pre-stained gel the presence of excess oligo can alter the run conditions leading to poor band quality.

In some embodiments, antibodies with many conjugated or attached oligonucleotides are also removed prior to hybridization to the DNA scaffold.

During the production of DNA nanoswitches, it is also important to be able to purify away excess oligonucleotides as excess functional oligonucleotides can bind to antigen thus blocking their ability to close a nanoswitch. Accordingly, in various embodiments, the invention described herein provides methods for purifying the nanoswitches of the invention from excess oligonucleotides. In some embodiments, this is achieved by adding a tag to the nanoswitch that can be bound by a functionalized bead. In some embodiments, the nanoswitch can be modified with a protein tag, small molecule tag, or a string of additional bases in the form of a single stranded region (e.g., this can be an overhang at the 5' or 3' end of the nanoswitch, or an unhybridized region anywhere along the Nanoswitch). In such embodiments, the nanoswitch with the protein or small molecule tag can be run through a purification resin with the complementary binder to the tag on the resin. For example, a biotinylated oligo can be bound to the nanoswitch. The Nanoswitch could then be purified with a resin made up of streptavidin beads. In another example, an end oligo can also be modified to have additional bases to include a polyA tail. The polyA tail would allow for purification using dT oligo beads. In various embodiments, the nanoswitch can be eluted by the addition of either binding partner excess biotin, excess streptavidin, excess polyA, or excess polyT. Additional protein, small molecule or nucleotide modifications may also be used which include, but are not limited to Biotin, digoxigenin, amines, sulfhydryls, click reagents (alkynes, azides), snap tags, antigens, antibodies, protein G, protein a, Streptavidin, sugars, lipids, alkyl-halides, aldehydes, and sulphates.

In some embodiments, purification of nanoswitches is achieved by temporal elutions to purify fully functional nanoswitches. When assembling DNA nanoswitches with two antibodies on them, 3 species can form: 1) a species with two antibodies on it (the desired product "Loopables"); 2) a species with only one antibody on it (undesired products "Halfers"); 3) a species with no antibodies on it (undesired products "Unfunctionalized"). In various embodiments, the invention described herein provides methods to drive the production of loopables over the halfers and/or the unfunctionalized products. In various embodiments, the invention described herein provides methods for selectively enriching and purifying the loopables. In some embodiments, methods described herein involve sequential affinity purification of the loopables as described in Example 7. In other embodiments, methods described herein involve temporal affinity purification of the loopables as described in Example 7.

Antibody conjugates and DNA nanoswitches can be stored in solution at 4° C. for up to 1 month. However, if stored at room temperature, the stability of the nanoswitch degrades much faster. Without wishing to be bound by theory, it is believed that storage of the antibody conjugate or the DNA nanoswitch in a dry form can increase the shelf life and allow significant improvement of the final nanoswitch concentration in the bodily fluid (which helps with the kinetics and fraction of analyte bound). Additionally, the concentration of the antibodies is very important to the nanoswitch hybridization, where the reaction efficiency depends directly on how dilute or concentrated the antibodies are. In various embodiments, drying of the nanoswitches is achieved using a Speed Vac or a lyophilizer. The various embodiments, drying of the nanoswitches does not denature the antibodies or the nanoswitches or reduce the functionality of the antibodies or the nanoswitches.

When hybridizing oligonucleotides to the nanoswitch scaffold, they usually need to be heated to remove secondary structure. However, antibody/protein/peptide oligo conjugates are often not tolerant of heating, as heating can denature proteins. This can lead to loss of functionality leading to decreased sensitivity, a complete lack of functionality, or aggregation which can cause false positive readings. Additionally, heating can lead to hydrolysis of the linker especially in the case of hydrazone linkages. Accordingly, in various embodiments, the methods use oligonucleotides which lack secondary structure so that they can be hybridized at room temperature. An exemplary protocol for low temperature hybridization is provided in Example 7. In various embodiments, methods described herein enable efficient hybridization of oligonucleotides without the risk of denaturing the proteins on the functionalized oligos.

Improvements Related to Polymers

In various embodiments, the invention described herein contemplates the use of polymers that change configuration upon binding to an analyte. Exemplary polymers include naturally occurring polymers or non-naturally occurring polymers. In various embodiments, the polymer may include nucleic acids, peptides, proteins, polysaccharides, lipids, nylon, PEG, PE, PET, neoprene, polyvinyl chloride (PVC or vinyl), polystyrene, polyethylene, polypropylene, polyacrylonitrile, PVB, silicone or combinations thereof.

In some embodiments, the polymers comprise nucleic acids. In some embodiments, the polymers comprise naturally occurring nucleotides and/or non-naturally occurring nucleotides. In some embodiments, the polymer comprises DNA, RNA, DNA analogs, RNA analogs, PNA, LNA and combinations thereof, provided it is able to hybridize in a sequence-specific manner to oligonucleotides and/or to be conjugated to a binding partner.

In some embodiments, the polymers are single-stranded nucleic acids. Such nucleic acids may be modified to include one or more binding partners at particular positions. The polymers may be single stranded nucleic acids hybridized to one or more modified oligonucleotides that are conjugated to one or more binding partners. Such nucleic acids may be referred to herein as scaffold nucleic acids. They may also be referred to as "single-stranded" and it is to be understood that this refers to their state prior to hybridization to the one or more oligonucleotides. In various embodiments, the scaffold nucleic acid may be hybridized to one or more including about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 250, about 300, about 350, about 400, about 450, or about 500, or more oligonucleotides. Each oligonucleotide may comprise one or more binding partners, depending on their length.

In some embodiments, the polymer may be a single-stranded nucleic acid, a partially double-stranded nucleic acid, or a completely double-stranded nucleic acid.

In some embodiments, the nucleic acid may be a naturally occurring nucleic acid (e.g., M13 DNA such as M13mp18). Use of M13 DNA as a scaffold nucleic acid is disclosed by Rothemund (2006) Nature 440:297-302, the entire contents are hereby incorporated by reference. In some embodiments, either the full length M13 DNA or fragments of M13 DNA are used. In some embodiments, nucleic acids to be used as polymers may be naturally occurring and thus harvested from a naturally occurring source. Alternatively, they may be non-naturally occurring nucleic acids such as polymerase chain reaction (PCR)-generated nucleic acids, rolling circle amplification (RCA)-generated nucleic acids, etc. Without wishing to be bound by theory, it is believed that larger ssDNA scaffolds yield greater signal/molecule as the number of dye molecules is directly proportional to the length of the DNA. A larger scaffold also allows for larger loop sizes, increased separation, and more options for multiplexing interactions. In some embodiments, the nucleic acid used is p8064 single strand DNA (ssDNA) by Tilibit.

In various embodiments, the nucleic acid may also comprise a plurality of nicks that are typically located between bound oligonucleotides. The length and the number of oligonucleotides used may vary. In some instances, the length and sequence of the oligonucleotides is chosen so that each oligonucleotide is bound to the scaffold nucleic acid at a similar strength. In some embodiments, the oligonucleotides are designed to be of approximately equal length. The oligonucleotides may be about 10, about 15, about 20, about 30, about 40, about 50, about 60, about 70, about 80, about 90 or about 100 nucleotides in length. In various embodiments, a plurality of nucleotides may be used, which include about 1, about 2, about 3, about 4, about 5, about 6, about 7, about 8, about 9, about 10, about 15, about 20, about 30, about 40, about 50, about 60, about 70, about 80, about 90, about 100, without limitation. The number of oligonucleotides hybridized to a particular scaffold may vary depending on the application.

In various embodiments, methods described herein involve the use of various enzymes for linearizing circular DNA such as circular single stranded DNA. In some embodiments, methods described herein utilize various restriction enzymes including, but not limited to, BtscI, EcoR1, and HindIII. Additional restriction enzymes that may be utilized include, but are not limited to, Type I enzymes (EC 3.1.21.3), Type II enzymes (EC 3.1.21.4), Type III enzymes (EC 3.1.21.5), and Type IV enzymes. Illustrative restriction enzymes include AcII, HindIII, SspI, MluCI, Tsp509I, PciI, AgeI, BspMI BfuAI, SexAI, MluI, BceAI, HpyCH4IV, HpyCH4III, BaeI, BsaXI, AflIII, SpeI, BsrI, BmrI, BglII, AfeI, AluI, StuI, ScaI, ClaI BspDI, PI-SceI, NsiI, AseI, SwaI, CspCI, MfeI, BssSI BssSaI, Nb.BssSI, BmgBI, PmlI, DraIII, AleI, EcoP15I, PvuII, AlwNI, BtsIMutI, TspRI, NdeI, NlaIII, CviAII, FatI, MslI, FspEI, XcmI, BstXI, PflMI, BccI, NcoI, BseYI, FauI, SmaI, XmaI TspMI, Nt.CviPII, LpnPI, AciI, SacII, BsrBI, MspI HpaII, ScrFI, BssKI StyD4I, BsaJI, BslI, BtgI, NciI, AvrII, MnlI, BbvCI, Nb.BbvCI, Nt.BbvCI, SbfI, Bpu10I, Bsu36I, EcoNI, HpyAV, BstNI, PspGI, StyI, BcgI, PvuI, BstUI, EagI, RsrII, BsiEI, BsiWI, BsmBI, Hpy99I, MspA1I, MspJI, SgrAI, BfaI, BspCNI, XhoI PaeR7I TliI, EarI, AcuI, PstI, BpmI, DdeI, SfcI, AflII, BpuEI, SmlI, AvaI, BsoBI, MboII, BbsI, XmnI, BsmI, Nb.BsmI, EcoRI, HgaI, AatII, ZraI, Tth111I, PflFI, PshAI, AhdI, DrdI, Eco53kI, SacI, BseRI, PleI, Nt.BstNBI, MlyI, HinfI, EcoRV, MboI Sau3AI DpnII BfuCI, DpnI, BsaBI, TfiI, BsrDI, Nb.BsrDI, BbvI, BtsI BtsaI, Nb.BtsI, BstAPI, SfaNI, SphI, SrfI, NmeAIII, NaeI, NgoMIV, BglI, AsiSI, BtgZI, HinP1I, HhaI, BssHII, NotI, Fnu4HI, Cac8I, MwoI, NheI, BmtI, SapI BspQI, Nt.BspQI, BlpI, TseI ApeKI, Bsp1286I, AlwI, Nt.AlwI, BamHI, FokI, BtsCI, HaeIII PhoI, FseI, SfiI, NarI, KasI, SfoI, PluTI, AscI, EciI, BsmFI, ApaI, PspOMI, Sau96I, NlaIV, KpnI, Acc65I, BsaI, HphI, BstEII, AvaII, BanI, BaeGI, BsaHI, BanII, RsaI, CviQI, BstZ17I, BciVI, SalI, Nt.BsmAI, BsmAI BcoDI, ApaLI, BsgI, AccI, Hpy166II, Tsp45I, HpaI, PmeI, HincII, BsiHKAI, ApoI ApoI-HF, NspI, BsrFI BsrFaI, BstYI, HaeII, CviKI-1, EcoO109I, PpuMI, I-CeuI, SnaBI, I-SceI, BspHI, BspEI, MmeI, TaqaI, NruI, Hpy188I, Hpy188III, XbaI, BclI, HpyCH4V, FspI, PI-PspI, MscI, BsrGI, MseI, PacI, PsiI, BstBI, DraI, PspXI, BsaWI, BsaAI, and EaeI. Illustrative restriction enzymes include EcoRI, EcoRII, BtscI, BamHI, HindIII, TaqI, NotI, HinFI, Sau3AI, PvuII, SmaI, HaeIII, HgaI, AluI, EcoRV, EcoP15I, KpnI, PstI, SacI, SalI, ScaI, SpeI, SphI, StuI, and XbaI.

In some embodiments, one or more restriction enzymes may be used for linearization. In an embodiment, the single stranded DNA is first subjected to BtscI treatment followed by EcoRI treatment.

For DNA nanoswitches that use circular plasmids, the successful linearization of the plasmid prior to hybridizing the functionalized oligos is important for nanoswitch performance. Inefficient linearization can lead to a reduction in DNA nanoswitch yield. Additionally, the circular DNA runs close to the looped DNA nanoswitch providing false signal which can contaminate true signal. This is especially important when trying to detect analyte at low concentrations. In various embodiments, the methods described herein provide an improved linearization process to ensure linear DNA purity by adding in excess of restriction enzyme (see, e.g., Example 7).

For DNA nanoswitches that use circular ssDNA as scaffold sources, the circular purity of the source is important for functional nanoswitch yield and band quality. Circular DNA is usually converted to linear DNA through the addition of a cut-site oligo and digestion enzyme. Any DNA which is already linear will be further cut. This leads to a continuous distribution of shorter DNA fragments. This distribution manifests as a leading smear that runs below the linear DNA band. Fragments which have been cut between the two antibodies sites will lead to pieces of DNA which have only 1 antibody. These can bind up antigen in solution, but will not adopt a loop geometry, leading to a loss in analyte detection sensitivity. Other cuts result in loopable DNA nanoswitches which run to other locations thus diluting signals. In various embodiments, the invention described herein contemplates the use of ssDNA source with high circular purity. In some embodiments, the circular purity is at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or 100%. In an embodiment, the invention described herein uses M13 DNA from Tilibit which is at least 99% circular.

Improvements Related to Samples and Analytes

In various embodiments, the sample being tested for the presence of the one or more analytes may be a biological sample. Exemplary biological samples include, but are not limited to bodily fluids such as a blood sample, a urine sample, a sputum sample, a saliva sample, a stool sample, a biopsy, and the like. For example, the biological samples may include, but are not limited to, serum, cerebrospinal fluid (CSF), lymph, mucus, cervical mucus, vaginal discharge, semen, menstrual blood, tears, sweat, ear wax, skin oil, skin cells, cheek swab samples, and throat swab samples. The sample may be complex. As used herein, a complex sample refers to a sample comprising a plurality of known and unknown components.

In an embodiment, the biological sample is urine. Human urine inherently contains DNA fragments, which can cause darkened backgrounds and unwanted bands to appear when run on a DNA staining gel. For example, running a urine sample through a gel may cause vertical streaking. In some embodiments, an urine sample is purified prior to analysis. In an embodiment, a urine sample is purified using hydroxyapatite, which can bind to DNA and remove DNA contaminates from the sample. For example, a urine sample can be initially spiked with phosphate and then purified using hydroxyapatite packed columns prior to analysis.

Bodily fluids often contain DNA degrading enzymes that can degrade the DNA nanoswitches of the invention. Such DNA degrading enzymes often require divalent ions (such as, without limitation magnesium, iron, calcium) to function. Accordingly, in various embodiments, methods described herein involve the use of metal chelators for reducing the degradation of DNA nanoswitches in samples that are bodily fluids. Exemplary metal chelators that may be used include, but are not limited to, EDTA, NTA, EGTA, DCTA, DTPA, BAPTA, ethylenediamine, porphine, heme, dimercaprol, DMPS, DMSA, DTPA, DEG, EDG, Dow Chemical VERSENE CSI, Dow Chemical VERSENE, DAPTA, Glycolic Acid, CyDTA, EDTA-OH, GEDTA, DHEG, IDA, DTPA-OH, NTP, Me-EDTA, HIDA, EDDP, EDTPO, NTPO, and the like.

In various embodiments, the analyte to be detected may be virtually any analyte provided that binding partners specific for the analyte are available. In various embodiments, the analyte can be bound by at least two binding partners simultaneously. In various embodiments, the analyte is bound by the binding partners at the same epitope or at different epitopes. In various embodiments, the analytes may be or may comprise nucleic acids, peptides or proteins, carbohydrates, lipids, or any combination thereof.

In various embodiments, the invention described herein contemplates the detection of Human chorionic gonadotropin (hCG), for example, as part of a pregnancy test. Fully intact hCG includes a dimer formed between two hCG subunits, alpha-hCG and beta-hCG. In some embodiments, the hCG is detected using antibodies, for example, a pair of antibodies that recognize one or more epitopes on alpha-hCG and beta-hCG. In an embodiment, the hCG is detected using antibodies that recognize beta-hCG. In various embodiments, any of the antibodies provided in Example 2 below may be utilized as a binding partner to detect hCG. In various embodiments, any known antibodies directed against alpha-hCG or beta-hCG may be utilized in the invention described herein. In some embodiments, the antibodies include INN-hCG-2, INN-hCG-2, 5008-SP5, 5008-SP5, and 5011 SPRN-1, or functional variants thereof. In some embodiments, the methods described herein can detect hCG earlier and with greater accuracy than conventional pregnancy tests on the market such as those pregnancy tests developed by First Response.

In various embodiments, the invention described herein contemplates the detection of luteinizing hormone (LH)/Lutropin, for example, as part of a test for identifying ovulation. Exemplary antibodies that recognize LH that may be used in methods described herein include, but are not limited to, Fitzgerald 10-L15A and 10-L15B, or functional variants thereof. In some embodiments, the invention described herein further contemplates the detection of estrone-3-glucoronide (E3G) as another biomarker for identifying ovulation. In some embodiments, the methods described herein can detect LH or E3G earlier and with greater accuracy than conventional ovulation tests on the market such as the ClearBlue Digital Ovulation Test or other ovulation tests developed by ClearBlue. In some embodiments, the methods described herein are particularly suited for predicting ovulation in women with polycystic ovary syndrome (PCOS) who cannot use the ovulation tests currently on the market due to their high LH baseline.

In various embodiments, the invention described herein contemplates the detection of Prostate Specific Antigen (PSA). Exemplary antibodies that recognize LH that may be used in methods described herein include, but are not limited to, anti-PSA 5001 (Medix), anti-PsA 5012 (Medix), or functional variants thereof.

In various embodiments, the invention described herein contemplates the detection of Herpes Simplex Virus (HSV) or antibodies against HSV present in the blood or serum. In some embodiments, the methods described herein relate to the detection of HSV-1 (oral herpes) or antibodies against HSV-1 present in the blood or serum. In other embodiments, the methods described herein relate to the detection of HSV-2 (genital herpes) or antibodies against HSV-2. For example, an HSV-1 or HSV-2 antigen may be used as binding partners to detect the presence of antibodies against HSV-1 or HSV-2 in the blood or serum.

In various embodiments, the invention described herein contemplates the detection of *Streptococcus pyogenes* (referred to herein as Strep-A). Exemplary antibodies that may be utilized for the detection of Strep-A include, but are not limited to, polyclonal antibodies targeting the Strep-A antigen or monoclonal Strep-A 2601 SPTN-5 or 2603 SPTN-5 antibodies, or functional variants thereof manufactured by Biospacific. In some embodiments, the methods described herein can detect Strep-A antigen earlier and with greater accuracy than conventional tests such as the QuickVue Dipstick Strep-A test. In an embodiment, the methods described herein are at least about 10 times, about 20 times, about 30 times, about 40 times, about 50 times, about 60 times, about 70 times, about 80 times, about 90 times, or at least about 100 times more sensitive than other rapid tests currently on the market e.g., the QuickVue Dipstic Strep-A test. In various embodiments, the methods described herein have enhanced specificity to Strep-A compared to other *Streptococcus* bacteria such as Strep-B, Strep-C or Strep-G.

In various embodiments, the invention described herein contemplates the detection of various infections, including gonorrhea and chlamydia. Exemplary antigens that may be detected using methods described herein include, but are not limited to, chlamydial LPS KDO-trisaccharide, chlamydial major outer membrane protein, all antigens of *Neisseria gonorrhea* including any major outer membrane protein.

In various embodiments, the invention described herein contemplates the detection of various diseases or conditions including diabetes and inflammation. Exemplary antigens that may be detected using methods described herein include, but are not limited to, Hemoglobin A1C and C-reactive protein. Additional antigens that may be detected by methods described herein include any known antigen that may be detected by ELISA or sandwich ELISA immunoassays currently on the market.

In some embodiments, the antigen described herein may be any biomarker for a biological event. In some embodiments, the biological events may include a disease event (i.e., disease biomarker), an inflammation event (i.e., an inflammation biomarker), a reproduction event (i.e., a reproduction biomarker), and/or an aging event (i.e., an aging biomarker).

Disease antigens/biomarkers may include one or more disease biomarkers related to or associated with the onset of disease, the offset of disease, and/or the presence of a disease state in a patient. Disease antigens/biomarkers may include one or more of a viral biomarker, a bacterial biomarker, a cancer biomarker, or a symptom biomarker. Viral antigens/biomarkers may include, but are not limited to biomarkers for common cold (e.g. rhinovirus), influenza, herpes, Zika, and/or HIV. In some embodiments, viral antigens/biomarkers may include one or more rhinovirus proteins, one or more influenza A/B/C proteins, one or more HSF-1/2 proteins, and/or one or more HIV virus proteins. Bacterial antigens/biomarkers may include, but are not limited to, biomarkers for strep throat, biomarkers for chlamydia, and/or biomarkers for gonorrhea. In some embodiments, bacterial antigens/biomarkers may include, but are not limited to, one or more *Streptococcus* proteins, one or more *Chlamydia trachomatis* proteins, and/or one or more *Neisseria gonorrhoeae* proteins. Symptom antigens/biomarkers may include, but are not limited to, biomarkers for coughing, wheezing, runny nose, nausea, cramps, tightness of the chest, light-headedness, sore throat, and/or chest pain. Disease antigens/biomarkers may also include, but are not limited to, biomarkers for cardiac distress and/or diabetes. In some embodiments, disease biomarkers may include troponin, CRP, and/or ha1c.

Cancer antigens/biomarkers may include biomarkers for breast cancer, colorectal cancer, gastric cancer, GIST, leukemia/lymphoma, lung cancer, melanoma, and or pancreatic cancer. In some embodiments, breast cancer biomarkers may include one or more of ER/PR and HER-2/neu. In some embodiments, colorectal cancer biomarkers may include one or more of EGFR, KRAS, and UGT1A1. In some embodiments, gastric cancer biomarkers may include HER-2/neu. In some embodiments GIST biomarkers may include c-KIT. In some embodiments, leukemia/lymphoma biomarkers may include one or more of CD20 antigen, CD30, FIP1L1-PDGRFalpha, PDGFR, PML/RAR alpha, TPMT, and UGT1A1. In some embodiments, lung cancer biomarkers may include one or more of ALK, EGFR, and KRAS. In some embodiments melanoma biomarkers may include BRAF.

Inflammatory antigens/biomarkers, which may include anti-inflammatory biomarkers, may include one or more inflammatory biomarkers described in U.S. Patent Application Publication No. 2010/0275282, the entirety of which is incorporated herein by reference.

Reproduction antigens/biomarkers may include biomarkers for ovulation, fertilization, implantation, and/or embryo development. In some embodiments, ovulation biomarkers may include leutinizing hormone. In some embodiments, fertilization biomarkers may include early pregnancy factor (EPF) and/or pre implantation factor. In some embodiments, implantation biomarkers may include beta HCG and/or hyperglycosylated HCG. In some embodiments, embryo development biomarkers may include beta HCG.

Aging antigens/biomarkers or age-related antigens/biomarkers include one or more biomarkers described in U.S. Patent Application Publication No. 2008/0124752, the entirety of which is incorporated herein by reference.

Additional antigens/biomarkers of interest include, but are not limited to, any known antigens/biomarkers associated with SARS, Hand foot and mouth disease, cardiac biomarkers, thyroid hormone, obesity biomarkers, biomarkers relating to bleeding disorders such as vWF, Factor 8, Factor 10, fifths disease, cold, flu, Ebola, *E coli, Listeria*, and *Salmonella*.

Improvements Related to Binding Partners

In various embodiments, the binding partners described herein may include, without limitation, antibodies including but not limited to single chain antibodies, antigen-binding antibody fragments, antigens (to be used to bind to their antibodies, for example), receptors, ligands, aptamers, aptamer receptors, nucleic acids, small molecules, and the like.

In various embodiments, the linkage between the polymer (e.g., nucleic acid) and the binding partner may be covalent or non-covalent depending on the strength of binding required for a particular application.

Methods for covalently linking and/or conjugating a polymer (e.g., nucleic acid) to a binding partner are known in the art. For example, commercial kits including the Solulink antibody-oligonucleotide conjugation kit, Thunder-link, Thunder-Link Plus may be utilized.

Methods for non-covalently linking and/or conjugating a polymer (e.g., nucleic acid) to a binding partner are known in the art. In some embodiments, a biotin-streptavidin system may be used to non-covalently link the polymer to the binding partner. For example, a streptavidin molecule may be attached to a binding partner, using, for example, the Lightning-Link Streptavidin kit. The streptavidin attached binding partner may subsequently be mixed with a biotin-functionalized polymer (e.g., oligonucleotide).

In some embodiments, the invention described herein contemplates the use of a coupling method utilizing copper-free click chemistry to functionalize antibodies, peptides, or proteins to a polymer (e.g., oligonucleotide). Exemplary methods are described in Example 3 below. In brief, the antibody, peptide, or protein can be activated with a ring-strained alkyne such as Dibenzocyclooctyne (DBCO) utilizing a NHS-DBCO linker to target free amines. DBCO can then be used to react with an azide-functionalized oligonucleotide.

In some embodiments, the invention described herein involves the use of a DNA nanoswitch that is functionalized with a pair of antibodies that can simultaneously bind to an antigen. In other embodiments, the detection of an antibody (e.g., antibody against HSV-1 or HSV-2) is required. In such embodiments, the DNA nanoswitch should be functionalized with two antigens (typically proteins) that can bind to a single antibody. This can be problematic if the protein contains few/no surface exposed lysines. One solution to this issue is to synthesize a short peptide of the antibody binding region on the protein. During peptide synthesis a functional residue can be added to the peptide. This ensures that each peptide can be coupled to an oligo. Another advantage of the use of peptides is that they can be suspended at extremely high molar concentration as compared to larger protein resulting in better reaction kinetics and yields. Accordingly, in various embodiments, methods described herein involve the creation of a peptide oligo conjugate where the peptide has been synthesized with a terminal azide. This can be couple to a DBCO-modified oligo via copper free click chemistry. An exemplary method for coupling azide-modified peptide to DBCO-functionalize oligonucleotides is described in Example 3.

In various embodiments, an N-hydroxysuccinimide (NHS)-based coupling strategy for hydrazone linkage of antibodies to a polymer (e.g., an oligonucleotide) is utilized. These methods rely on NHS coupling of reactive linkers. As NHS coupling can react with any exposed lysine residue, this method has the risk of chemically modifying the binding pocket of the antibody resulting in steric hindrance that may reduce or abolish the antibodies ability to bind to its antigen. However, by targeting antibody-glycosylation sites in the CH2 heavy-chain region of an IgG, one can be sure that the binding pocket remains free of chemical modification. Accordingly, in some embodiments, the invention described herein utilizes a coupling strategy that employs the oxidation of sugar residues, including terminal sialic acid and internal mannose residues. As described in Example 3, in such embodiments, the method involves the activation of hydrizide-oligonucleotides, followed by oxidation of IgG glycosylation sites, to achieve hydrazone linkage of oxidized IgG to hydrizide-oligonucleotides.

In various embodiments, the sample being tested is combined with a polymer pair or with a polymer (conjugated to analyte-specific binding partners), such as a nanoswitch, under conditions that allow binding of analyte-specific binding partners to their respective analytes if present in the sample. Those conditions may vary depending on the nature of the analyte and the binding partner. Those conditions may also take into consideration the stability of the polymer, binding partner and/or analyte. In some embodiments, the conditions may comprise inhibitors such as DNase inhibitors, RNase inhibitors, or protease inhibitors.

Improvements Related to Products Including Kits

In various embodiments, the invention described herein relate, in part, to kits comprising nanoswitches, polymers or polymer pairs along with specific reagents for analyte detection. The polymers may be conjugated to binding partners of interest or they may be provided with binding partners of interest with or without the reagents required to conjugate the two. Thus, for example, in some embodiments, a polymer conjugated to two binding partners which bind to the same analyte is provided. In some embodiments, two polymers each conjugated to a binding partner, wherein both binding partners bind specifically to the same analyte. In still other embodiments, provided are oligonucleotides that are bound to binding partners of interest and scaffold nucleic acids to which such oligonucleotides hybridize to form one version of the polymers of this disclosure. Similarly, nanoswitches may be provided fully assembled or scaffolds and oligonucleotides with or without conjugated binding partners may be provided.

In various embodiments, instructions for conjugation of binding partners to polymers such as nucleic acids may also be provided. In some embodiments, instructions for incubating nanoswitches or polymers with samples including complex samples may also be provided.

In some embodiments, the invention described herein provides a pregnancy detection kit which involve the detection of hCG (e.g., (β-hCG).

In some embodiments, the invention described herein provides an ovulation detection kit which involves the detection of LH.

In some embodiments, the invention described herein provides a kit that can provide ovulation and pregnancy testing in one test stick, as described, for example in Example 4.

In some embodiments, the invention described herein provides a kit for detecting PSA.

In some embodiments, the invention described herein provides a kit for detecting HSV (e.g., HSV-1 and/or HSV-2). In an embodiment, the kits described herein are specific for HSV-2 over HSV-1.

In some embodiments, the invention described herein provides a kit for detecting Strep-A.

In other embodiments, the invention described herein provides a kit for detecting infection by, for example, gonorrhea and chlamydia.

In other embodiments, the invention described herein provides a kit for detecting a disease or condition, such as, but not limited to, inflammation and diabetes.

In various embodiments, methods and kits described herein allows for personal baselining for a biomarker of interest (e.g., as described in Example 4). In such embodiments, the methods described herein allow for a determination of a normal range for each individual user. In some embodiments, the user is alerted if there is any deviation from the individual's personal normal range.

Improvements Related to Gel Running, Gel Processing, Gel Analysis and Band Quantification To determine the presence and/or concentration of the analyte in a sample, the methods described herein are performed and the intensity of the looped band after gel electrophoresis is determined. The invention described herein contemplates various improvements in gel analysis and band quantification.

In various embodiments, the methods described herein provide gels with reduced backgrounds. In some embodiments, the gels are pre-stained gels such as those pre-stained with SYBR Gold or GELRed. Additional non-limiting examples of pre-stained gels include those gels pre-stained with, ethidium bromide, actinomycin D, psoralen, 4'-aminomethyl-4,5',8-trimethylpsoralen (AMT), Hoechst 33258, EvaGreen dye, GelRed, GelGreen, SYBR Green I, SYBR Green II, OliGreen, RiboGreen SYBR GreenEr, SYBR Gold, SYBR Safe, gel red, LC Green, LC Green Plus, BOXTO, BEBO, SYBR DX, SYTO9, SYTOX Blue, SYTOX Green, SYTOX Orange, SYTO dyes, POPO-1, POPO-3, BOBO-1, BOBO-3, YOYO-1, YOYO-3, TOTO-1, TOTO-3, PO-PRO-1, BO-PRO-1, YO-PRO-1, TO-PRO-1, JO-PRO-1, PO-PRO-3, LO-PRO-1, BO-PRO-3, YO-PRO-3, TO-PRO-3, TO-PRO-5, Ethidium Homodimer-1, Ethidium Homodimer-2, Ethidium Homodimer-3, propidium iodide, various Hoechst dyes, DAPI, ResoLight, Chromofy, and acridine homodimer, or combinations or mixtures thereof.

In some embodiments, methods described herein involve a slicing technology (see Example 5) that provides the benefit of reducing gel background and/or increasing running distance within the gel by reducing the resistance along the electron pathway. In some embodiments, such methods involve reducing the size of the gel that is used.

In some embodiments, gels of the sizes less than about 7 cm, about 3.5 cm, about 2 cm, or about 1.5 cm are used. In an embodiment, gels of about 2 cm are used. In some embodiments, fluorescent DNA binding dyes are run out of the gel prior to gel analysis.

When running gels that have been pre-stained with fluorescent DNA binding dyes, the residual dye left in the gel can sometimes make gel analysis problematic. Accordingly, in some embodiments, methods described herein utilize a Flip technology (see Example 5) involving running the dye out of the gel in a direction orthogonal to the run direction. In such embodiments, the gel can be rotated or separate sets of electrodes may be used.

In various embodiments, methods described herein utilize agarose gels for gel electrophoresis. In some embodiments, additives may be added to the agarose gel to change the running conditions. In an embodiment, the additive is a polymer such as hydroxyethyl cellulose (HEC). Without wishing to be bound by theory, it is believed that adding HEC to agarose gels improves the separation between the linear and looped NS bands compared to agarose alone. This allows gels to be run for less time but maintain good separation for later analysis. In various embodiments, the amount of HEC in the gel range from about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, to about 1%. In various embodiments, other additives such as polyethylene oxide (PEO) or locust bean gum (LBG) may be utilized.

In various embodiments, buffer levels are improved to enhance resolution of bands, to provide sharper bands, and/or to better distinguish looped confirmation from the linear conformation. In some embodiments, buffer level refers to the height of electrophoresis buffer that sits above the gel. When there are increased amounts of buffer above the gel, current can travel through the buffer rather than through the gel. Accordingly, in various embodiments, the buffer level is about 1 inch, about ⅞ inch, about ⅝ inch, about ⅝ inch, about ⅘ inch, about ⅜ inch, about ⅔ inch, or about ⅛ inch above the gel. In an embodiment, the buffer level may be about ⅝ inches above the gel. In another embodiment, the buffer level may be about ⅔ inches above the gel. In some embodiments, the buffer level may be below the gel. In such embodiments, the buffer level may be about 1 inch, about ⅞ inch, about ⅝ inch, about ⅝ inch, about ⅘ inch, about ⅜ inch, about ⅔ inch, or about ⅛ inch below the gel.

In various embodiments, the methods described herein involve running a gel using a constant voltage. Without wishing to be bound by theory, it is believed that a constant voltage does reduce the amount of heat generated as it runs, and the current does reduce over time. This makes for a safer running environment for long gel runs.

In other embodiments, methods described herein involve running a gel using constant current. This is applicable to, for example, methods involving quick gel runs where heat generation is more manageable. Without wishing to be bound by theory, it is believed that running a gel using constant current provides improved sharpness of the bands, e.g., looped bands. In various embodiments, methods described herein involve running a gel under a constant current of about 1 mA to about 500 mA. For example, the current may be about 1 mA, about 2 mA, about 3 mA, about 4 mA, about 5 mA, about 6 mA, about 7 mA, about 8 mA, about 9 mA, about 10 mA, about 20 mA, about 30 mA, about 40 mA, about 50 mA, about 60 mA, about 70 mA, about 80 mA, about 90 mA, about 100 mA, about 150 mA, about 200 mA, about 250 mA, about 300 mA, about 350 mA, about 400 mA, about 450 mA, or about 500 mA.

In various embodiments, methods described herein involve running a gel under increased electric field as measured in volts/centimeter. Without wishing to be bound by theory, it is believed that such methods result in better separation of looped DNA from unlooped DNA. Further, it is also believed that such methods result in shorter test run time for the end user. In such embodiments, the method may involve running a gel using high voltage. In various embodiments, the gels are run using a voltage of about 1V to about 500V. For example, the gels may be running using a voltage of about 1V, about 2V, about 3V, about 4V, about 5V, about 6V, about 7V, about 8V, about 9V, about 10V, about 15V, about 20V, about 30V, about 40V, about 50V, about 60V, about 70V, about 80V, about 90V, about 100V, about 110V, about 120V, about 130V, about 140V, about 150V, about 160V, about 170V, about 180V, about 190V, about 200V, about 210V, about 220V, about 230V, about 240V, about 250V, about 260V, about 270V, about 280V, about 290V, about 300V, about 310V, about 320V, about 330V, about 340V, about 350V, about 360V, about 370V, about 380V, or about 390V, about 400V, about 450V, or about 500V. In other embodiments, the method may involve the use of small gels. In various embodiments, the gels involve using gel boxes with a size of about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 25 cm, or about 30 cm.

In various embodiments, methods described herein involve pre-staining a gel. Without wishing to be bound by theory, it is believed that pre-staining a gel increases the separation of looped and linear DNA and/or allows shorter gel running time. Further still, pre-staining a gel allows for a gel to be analyzed immediately after running. In various embodiments, the gels may be pre-stained using SYBR Gold or GELRed. Additional non-limiting examples of pre-stained gels include those gels pre-stained with, ethidium bromide, actinomycin D, psoralen, 4'-aminomethyl-4,5',8-trimethylpsoralen (AMT), Hoechst 33258, EvaGreen dye, GelRed, GelGreen, SYBR Green I, SYBR Green II, OliGreen, RiboGreen SYBR GreenEr, SYBR Gold, SYBR Safe, gel red, LC Green, LC Green Plus, BOXTO, BEBO, SYBR DX, SYTO9, SYTOX Blue, SYTOX Green, SYTOX Orange, SYTO dyes, POPO-1, POPO-3, BOBO-1, BOBO-3, YOYO-1, YOYO-3, TOTO-1, TOTO-3, PO-PRO-1, BO-PRO-1, YO-PRO-1, TO-PRO-1, JO-PRO-1, PO-PRO-3, LO-PRO-1, BO-PRO-3, YO-PRO-3, TO-PRO-3, TO-PRO-5, Ethidium Homodimer-1, Ethidium Homodimer-2, Ethidium Homodimer-3, propidium iodide, various Hoechst dyes, DAPI, ResoLight, Chromofy, and acridine homodimer, or combinations or mixtures thereof.

In various embodiments, methods described herein involve strict regulation of the gel running buffer composition to ensure running results. In some embodiments, the running buffers described herein are produced using precision graduated cylinders and/or volumetric flasks.

In various embodiments, methods described herein involve adding a florescent DNA stain to the gel sample prior to gel loading. Without wishing to be bound by theory, it is believed that adding a DNA stain to the sample prior to gel loading improves the clarity of the linear and looped DNA bands and/or make the bands sharper.

Methods described herein also contemplate improvements in gel image processing. In some embodiments, methods described herein may involve non-homogenous backgrounds. In such embodiments, the background is corrected as described in Example 8 to ensure accuracy of the gel analysis. In some embodiments, methods described herein involve analysis of each individual column in a gel lane as described, for example, in Example 8. For example, rather than analyzing a gel lane by taking the mean/median or some other ranked filter of each row to form a 1D intensity profile, each individual column in a gel lane can be analyzed, and the area of the looped band measured. Without wishing to be bound by theory, it is believed that using this as a population of measurements rather than a single measurement, one can fit the population and estimate the error in analyte detection measurement.

Exemplary Oligonucleotide Sequences

The following tables provide various oligonucleotides that may be used in the methods disclosed herein. In various embodiments, these sequences have been identified to have low secondary structures thus allowing nanoswitch assembly at room temperature.

| Identifier | SEQ ID NO: | Sequence |
|---|---|---|
| 4.44 | 1 | CTCAAATATCAAACCCTCAATCAATATCTGGTCAGTTGGC |
| 4.44_29 | 4 | CTCAAATATCAAACCCTCAATCAATATCT |
| 4.13 | 5 | TTGGCAAATCAACAGTTGAAAGGAATTG |
| 4.08 F20 | 8 | CACCTTGCTGAACCTCAAAT |
| 4.08 M20 | 9 | ATCAAACCCTCAATCAATAT |
| 4.08 L20 | 10 | CTGGTCAGTTGGCAAATCAA |
| 4.09 F20 | 11 | CACCTTGCTGAACCTCAAAT |
| 4.09 M20 | 12 | CAGTTGAAAGGAATTGAGGA |
| 4.09 L20 | 13 | AGGTTATCTAAAATATCTTT |
| 5.09_10 | 14 | GAGAAGAGTCAATAGTGAAT |
| 5.10_1 | 15 | TTATCAAAATCATAGGTCTG |
| 5.10_2 | 16 | AGAGACTACCTTTTTAACC |
| 5.10_3 | 17 | AGAGACTACCTTTTTAACC |
| 5.10_4 | 18 | TCCGGCTTAGGTTGGGTTAT |
| L3 | 20 | CAATATATGTGAGTGAATAACCTTGCTTCTGTAAATCGTCGCTATTAATTAATTTTCCCT |
| 4.19 M48 | 21 | ATAACTATATGTAAATGCTGATGCAAATCCAATCGCAAGACAAAGAAC |
| 4.19_1 | 6 | ATAACTATATGTAAATGCTGATGC |
| 4.19_3 | 7 | AAATCCAATCGCAAGACAAAGAAC |
| L4 | 22 | CTGAACAAGAAAAATAATATCCCATCCTAATTTACGAGCATGTAGAAACCAATCAATAAT |
| L5 | 23 | TTGTTTAACGTCAAAAATGAAAATAGCAGCCTTTACAGAGAGAATAACATAAAAACAGGG |
| EcoR1 cut oligo | 24 | TACCGAGCTCGAATTCGTAATCATG |
| HindIII 8064 Tilibit M13 cut | 25 | GGCCAGTGCCAAGCTTTCAGAGGTG |
| HindIII 7249 NEB M13 cut | 26 | GGCCAGTGCCAAGCTTGCATGCCTG |

| Type | Identifier # | SEQ ID NO | Sequence | Sequence Length |
|---|---|---|---|---|
| V1.01-V1.09 | | | | |
| BB | 1.01 | 27 | AGAGCATAAAGCTAAATCGGTTGTACCAAAAACATTATGACCCTGTAATACTTTTGCGGG | 60 |
| BB | 1.02 | 28 | AGAAGCCTTTATTTCAACGCAAGGATAAAAATTTTTAGAACCCTCATATATTTTAAATGC | 60 |
| BB | 1.03 | 29 | AATGCCTGAGTAATGTGTAGGTAAAGATTCAAAAGGGTGAGAAAGGCCGGAGACAGTCAA | 60 |
| BB | 1.04 | 30 | ATCACCATCAATATGATATTCAACCGTTCTAGCTGATAAATTAATGCCGGAGAGGGTAGC | 60 |
| BB | 1.05 | 31 | TATTTTTGAGAGATCTACAAAGGCTATCAGGTCATTGCCTGAGAGTCTGGAGCAAACAAG | 60 |
| BB | 1.06 | 32 | AGAATCGATGAACGGTAATCGTAAAACTAGCATGTCAATCATATGTACCCCGGTTGATAA | 60 |
| BB | 1.07 | 33 | TCAGAAAAGCCCCAAAAACAGGAAGATTGTATAAGCAAATATTTAAATTGTAAACGTTAA | 60 |
| BB | 1.08 | 34 | TATTTTGTTAAAATTCGCATTAAATTTTTGTTAAATCAGCTCATTTTTTAACCAATAGGA | 60 |
| BB | 1.09 | 35 | ACGCCATCAAAAATAATTCGCGTCTGGCCTTCCTGTAGCCAGCTTTCATCAACATTAAAT | 60 |
| V2.01-V2.10 | | | | |
| BB | 2.01 | 36 | GGATAGGTCACGTTGGTGTAGATGGGCGCATCGTAACCGTGCATCTGCCAGTTTGAGGGG | 60 |
| BB | 2.02 | 37 | ACGACGACAGTATCGGCCTCAGGAAGATCGCACTCCAGCCAGCTTTCCGGCACCGCTTCT | 60 |
| BB | 2.03 | 38 | GGTGCCGGAAACCAGGCAAAGCGCCATTCGCCATTCAGGCTGCGCAACTGTTGGGAAGGG | 60 |
| BB | 2.04 | 39 | CGATCGGTGCGGGCCTCTTCGCTATTACGCCAGCTGGCGAAAGGGGGATGTGCTGCAAGG | 60 |
| BB | 2.05 | 40 | CGATTAAGTTGGGTAACGCCAGGGTTTTCCCAGTCACGACGTTGTAAAACGACGGCAGT | 60 |

| Type | Identifier # | SEQ ID NO | Sequence | Sequence Length |
|---|---|---|---|---|
| BB | 2.06 | 41 | GCCAAGCTTGCATGCCTGCAGGTCGACTCTAGAGGATCCCCGGGTACCGAGCTCGAATTC | 60 |
| BB | 2.07 | 42 | GTAATCATGGTCATAGCTGTTTCCTGTGTGAAATTGTTATCCGCTCACAATTCCACACAA | 60 |
| BB | 2.08 | 43 | CATACGAGCCGGAAGCATAAAGTGTAAAGCCTGGGGTGCCTAATGAGTGAGCTAACTCAC | 60 |
| BB | 2.09 | 44 | ATTAATTGCGTTGCGCTCACTGCCCGCTTTCCAGTCGGGAAACCTGTCGTGCCAGCTGCA | 60 |
| BB | 2.10 | 45 | TTAATGAATCGGCCAACGCGCGGGGAGAGGCGGTTTGCGTATTGGGCGCCAGGGTGGTTT | 60 |

V3.01-V3.10

| Type | Identifier # | SEQ ID NO | Sequence | Sequence Length |
|---|---|---|---|---|
| BB | 3.01 | 46 | GTTGCAGCAAGCGGTCCACGCTGGTTTGCCCCAGCAGGCGAAAATCCTGTTTGATGGTGG | 60 |
| BB | 3.02 | 47 | TTCCGAAATCGGCAAAATCCCTTATAAATCAAAAGAATAGCCCGAGATAGGGTTGAGTGT | 60 |
| BB | 3.03 | 48 | TGTTCCAGTTTGGAACAAGAGTCCACTATTAAAGAACGTGGACTCCAACGTCAAAGGGCG | 60 |
| BB | 3.04 | 49 | AAAAACCGTCTATCAGGGCGATGGCCCACTACGTGAACCATCACCCAAATCAAGTTTTTT | 60 |
| BB | 3.05 | 50 | GGGGTCGAGGTGCCGTAAAGCACTAAATCGGAAACCCTAAAGGGAGCCCCCGATTTAGAGC | 60 |
| BB | 3.06 | 51 | TTGACGGGGAAAGCCGGCGAACGTGGCGAGAAAGGAAGGGAAGAAAGCGAAAGGAGCGGG | 60 |
| BB | 3.07 | 52 | CGCTAGGGCGCTGGCAAGTGTAGCGGTCACGCTGCGCGTAACCACCACACCCGCCGCGCT | 60 |
| BB | 3.08 | 53 | TAATGCGCCGCTACAGGGCGCGTACTATGGTTGCTTTGACGAGCACGTATAACGTGCTTT | 60 |
| BB | 3.09 | 54 | CCTCGTTAGAATCAGAGCGGGAGCTAAACAGGAGGCCGATTAAAGGGATTTTAGACAGGA | 60 |
| BB | 3.10 | 55 | ACGGTACGCCAGAATCCTGAGAAGTGTTTTTATAATCAGTGAGGCCACCGAGTAAAAGAG | 60 |

V4.01-V4.10

| Type | Identifier # | SEQ ID NO | Sequence | Sequence Length |
|---|---|---|---|---|
| BB | 4.01 | 56 | TTGCCTGAGTAGAAGAACTCAAACTATCGGCCTTGCTGGTAATATCCAGAACAATATTAC | 60 |
| BB | 4.02 | 57 | CGCCAGCCATTGCAACAGGAAAAACGCTCATGGAAATACCTACATTTTGACGCTCAATCG | 60 |
| BB | 4.03 | 58 | TCTGAAATGGATTATTTACATTGGCAGATTCACCAGTCACACGACCAGTAATAAAAGGGA | 60 |
| BB | 4.04 | 59 | CATTCTGGCCAACAGAGATAGAACCCTTCTGACCTGAAAGCGTAAGAATACGTGGCACAG | 60 |
| BB | 4.05 | 60 | ACAATATTTTTGAATGGCTATTAGTCTTTAATGCGCGAACTGATAGCCCTAAAACATCGC | 60 |
| BB | 4.06 | 61 | CATTAAAAATACCGAACGAACCACCAGCAGAAGATAAAACAGAGGTGAGGCGGTCAGTAT | 60 |
| BB | 4.07 | 62 | TAACACCGCCTGCAACAGTGCCACGCTGAGAGCCAGCAGCAAATGAAAAATCTAAAGCAT | 60 |
| BB | 4.08 | 63 | CACCTTGCTGAACCTCAAATATCAAACCCTCAATCAATATCTGGTCAGTTGGCAAATCAA | 60 |
| BB | 4.09 | 64 | CAGTTGAAAGGAATTGAGGAAGGTTATCTAAAATATCTTTAGGAGCACTAACAACTAATA | 60 |
| BB | 4.10 | 65 | GATTAGAGCCGTCAATAGATAATACATTTGAGGATTTAGAAGTATTAGACTTTACAAACA | 60 |

V5.01-V5.10

| Type | Identifier # | SEQ ID NO | Sequence | Sequence Length |
|---|---|---|---|---|
| BB | 5.01 | 66 | CATTATCATTTTGCGGAACAAAGAAACCACCAGAAGGGAGCGGAATTATCATCATATTCCT | 60 |
| BB | 5.02 | 67 | GATTATCAGATGATGGCAATTCATCAATATAATCCTGATTGTTTGGATTATACTTCTGAA | 60 |
| BB | 5.03 | 68 | TAATGGAAGGGTTAGAACCTACCATATCAAAATTATTTGCACGTAAAACAGAAATAAAGA | 60 |
| BB | 5.04 | 69 | AATTGCGTAGATTTTCAGGTTTAACGTCAGATGAATATACAGTAACAGTACCTTTTACAT | 60 |
| BB | 5.05 | 70 | CGGGAGAAACAATAACGGATTCGCCTGATTGCTTTGAATACCAAGTTACAAAATCGCGCA | 60 |
| BB | 5.06 | 71 | GAGGCGAATTATTCATTTCAATTACCTGAGCAAAAGAAGATGATGAAACAAACATCAAGA | 60 |
| BB | 5.07 | 72 | AAACAAAATTAATTACATTTAACAATTTCATTTGAATTACCTTTTTTAATGGAAACAGTA | 60 |
| BB | 5.08 | 73 | CATAAATCAATATATGTGAGTGAATAACCTTGCTTCTGTAAATCGTCGCTATTAATTAAT | 60 |
| BB | 5.09 | 74 | TTTCCCTTAGAATCCTTGAAAACATAGCGATAGCTTAGATTAAGACGCTGAGAAGAGTCA | 60 |
| BB | 5.10 | 75 | ATAGTGAATTTATCAAAATCATAGGTCTGAGAGACTACCTTTTTAACCTCCGGCTTAGGT | 60 |

V6.01-V6.10

| Type | Identifier # | SEQ ID NO | Sequence | Sequence Length |
|---|---|---|---|---|
| BB | 6.01 | 76 | GAAAACTTTTTCAAATATATTTTAGTTAATTTCATCTTCTGACCTAAATTTAATGGTTTG | 60 |
| BB | 6.02 | 77 | AAATACCGACCGTGTGATAAATAAGGCGTTAAATAAGAATAAACACCGGAATCATAATTA | 60 |
| BB | 6.03 | 78 | CTAGAAAAAGCCTGTTTAGTATCATATGCGTTATACAAATTCTTACCAGTATAAAGCCAA | 60 |
| BB | 6.04 | 79 | CGCTCAACAGTAGGGCTTAATTGAGAATCGCCATATTTAACAACGCCAACATGTAATTTA | 60 |
| BB | 6.05 | 80 | GGCAGAGGCATTTTCGAGCCAGTAATAAGAGAATATAAAGTACCGACAAAAGGTAAAGTA | 60 |
| BB | 6.06 | 81 | ATTCTGTCCAGACGACGACAATAAACAACATGTTCAGCTAATGCAGAACGCGCCTGTTTA | 60 |
| BB | 6.07 | 82 | TCAACAATAGATAAGTCCTGAACAAGAAAAATAATATCCCATCCTAATTTACGAGCATGT | 60 |
| BB | 6.08 | 83 | AGAAACCAATCAATAATCGGCTGTCTTTCCTTATCATTCCAAGAACGGGTATTAAACCAA | 60 |
| BB | 6.09 | 84 | GTACCGCACTCATCGAGAACAAGCAAGCCGTTTTTATTTTCATCGTAGGAATCATTACCG | 60 |
| BB | 6.10 | 85 | CGCCCAATAGCAAGCAAATCAGATATAGAAGGCTTATCCGGTATTCTAAGAACGCGAGGC | 60 |

V7.01-V7.10

| Type | Identifier # | SEQ ID NO | Sequence | Sequence Length |
|---|---|---|---|---|
| BB | 7.01 | 86 | ATTTTGCACCCAGCTACAATTTTATCCTGAATCTTACCAACGCTAACGAGCGTCTTTCCA | 60 |
| BB | 7.02 | 87 | GAGCCTAATTTGCCAGTTACAAAATAAACAGCCATATTATTTATCCCAATCCAAATAAGA | 60 |
| BB | 7.03 | 88 | AACGATTTTTGTTTAACGTCAAAAATGAAAATAGCAGCCTTTACAGAGAGAATAACATA | 60 |
| BB | 7.04 | 89 | AAAACAGGGAAGCGCATTAGACGGGAGAATTAACTGAACACCCTGAACAAAGTCAGAGGG | 60 |
| BB | 7.05 | 90 | TAATTGAGCGCTAATATCAGAGAGATAACCCACAAGAATTGAGTTAAGCCCAATAATAAG | 60 |
| BB | 7.06 | 91 | AGCAAGAAACAATGAAATAGCAATAGCTATCTTACCGAAGCCCTTTTTAAGAAAAGTAAG | 60 |
| BB | 7.07 | 92 | CAGATAGCCGAACAAAGTTACCAGAAGGAAACCGAGGAAACGCAATAATAACGGAATACC | 60 |
| BB | 7.08 | 93 | CAAAAGAACTGGCATGATTAAGACTCCTTATTACGCAGTATGTTAGCAAACGTAGAAAAT | 60 |
| BB | 7.09 | 94 | ACATACATAAAGGTGGCAACATATAAAAGAAACGCAAAGACACCACGGAATAAGTTTATT | 60 |
| BB | 7.10 | 95 | TTGTCACAATCAATAGAAAATTCATATGGTTTACCAGCGCCAAAGACAAAAGGGCGACAT | 60 |

V8.01-V8.10

| Type | Identifier # | SEQ ID NO | Sequence | Sequence Length |
|---|---|---|---|---|
| BB | 8.01 | 96 | TCACCGTCACCGACTTGAGCCATTTGGGAATTAGAGCCAGCAAAATCACCAGTAGCACCA | 60 |
| BB | 8.02 | 97 | TTACCATTAGCAAGGCCGGAAACGTCACCAATGAAACCATCGATAGCAGCACCGTAATCA | 60 |

-continued

| Type | Identifier # | SEQ ID NO | Sequence | Sequence Length |
|------|--------------|-----------|----------|-----------------|
| BB | 8.03 | 98 | GTAGCGACAGAATCAAGTTTGCCTTTAGCGTCAGACTGTAGCGCGTTTTCATCGGCATTT | 60 |
| BB | 8.04 | 99 | TCGGTCATAGCCCCCTTATTAGCGTTTGCCATCTTTTCATAATCAAAATCACCGGAACCA | 60 |
| BB | 8.05 | 100 | GAGCCACCACCGGAACCGCCTCCCTCAGAGCCGCCACCCTCAGAACCGCCACCCTCAGAG | 60 |
| BB | 8.06 | 101 | CCACCACCCTCAGAGCCGCCACCAGAACCACCACCAGAGCCGCCGCCAGCATTGACAGGA | 60 |
| BB | 8.07 | 102 | GGTTGAGGCAGGTCAGACGATTGGCCTTGATATTCACAAACAAATAAATCCTCATTAAAG | 60 |
| BB | 8.08 | 103 | CCAGAATGGAAAGCGCAGTCTCTGAATTTACCGTTCCAGTAAGCGTCATACATGGCTTTT | 60 |
| BB | 8.09 | 104 | GATGATACAGGAGTGTACTGGTAATAAGTTTTAACGGGGTCAGTGCCTTGAGTAACAGTG | 60 |
| BB | 8.10 | 105 | CCCGTATAAACAGTTAATGCCCCCTGCCTATTTCGGAACCTATTATTCTGAAACATGAAA | 60 |

V9.01-V9.10

| BB | 9.01 | 106 | CCAGGCGGATAAGTGCCGTCGAGAGGGTTGATATAAGTATAGCCCGGAATAGGTGTATCA | 60 |
| BB | 9.02 | 107 | CCGTACTCAGGAGGTTTAGTACCGCCACCCTCAGAACCGCCACCCTCAGAACCGCCACCC | 60 |
| BB | 9.03 | 108 | TCAGAGCCACCACCCTCATTTTCAGGGATAGCAAGCCCAATAGGAACCCATGTACCGTAA | 60 |
| BB | 9.04 | 109 | CACTGAGTTTCGTCACCAGTACAAACTACAACGCCTGTAGCATTCCACAGACAGCCCTCA | 60 |
| BB | 9.05 | 110 | TAGTTAGCGTAACGATCTAAAGTTTTGTCGTCTTTCCAGACGTTAGTAAATGAATTTTCT | 60 |
| BB | 9.06 | 111 | GTATGGGATTTTGCTAAACAACTTTCAACAGTTTCAGCGGAGTGAGAATAGAAAGGAACA | 60 |
| BB | 9.07 | 112 | ACTAAAGGAATTGCGAATAATAATTTTTTCACGTTGAAAATCTCCAAAAAAAAGGCTCCA | 60 |
| BB | 9.08 | 113 | AAAGGAGCCTTTAATTGTATCGGTTTATCAGCTTGCTTTCGAGGTGAATTTCTTAAACAG | 60 |
| BB | 9.09 | 114 | CTTGATACCGATAGTTGCGCCGACAATGACAACAACCATCGCCCACGCATAACCGATATA | 60 |
| BB | 9.10 | 115 | TTCGGTCGCTGAGGCTTGCAGGGAGTTAAAGGCCGCTTTTGCGGGATCGTCACCCTCAGC | 60 |

V10.01-V10.10

| BB | 10.01 | 116 | CTTTTTCATGAGGAAGTTTCCATTAAACGGGTAAAATACGTAATGCCACTACGAAGGCAC | 60 |
| BB | 10.02 | 117 | CAACCTAAAACGAAAGAGGCAAAAGAATACACTAAAACACTCATCTTTGACCCCCAGCGA | 60 |
| BB | 10.03 | 118 | TTATACCAAGCGCGAAACAAAGTACAACGGAGATTTGTATCATCGCCTGATAAATTGTGT | 60 |
| BB | 10.04 | 119 | CGAAATCCGCGACCCTGCTCCATGTTACTTAGCCGGAACGAGGCGCAGACGGTCAATCATA | 60 |
| BB | 10.05 | 120 | AGGGAACCGAACTGACCAACTTTGAAAGAGGACAGATGAACGGTGTACAGACCAGGCGCA | 60 |
| BB | 10.06 | 121 | TAGGCTGGCTGACCTTCATCAAGAGTAATCTTGACAAGAACCGGATATTCATTACCCAAA | 60 |
| BB | 10.07 | 122 | TCAACGTAACAAAGCTGCTCATTCAGTGAATAAGGCTTGCCCTGACGAGAACACCAGAA | 60 |
| BB | 10.08 | 123 | CGAGTAGTAAATTGGGCTTGAGATGGTTTAATTTCAACTTTAATCATTGTGAATTACCTT | 60 |
| BB | 10.09 | 124 | ATGCGATTTTAAGAACTGGCTCATTATACCAGTCAGGACGTTGGGAAGAAAAATCTACGT | 60 |
| BB | 10.10 | 125 | TAATAAAACGAACTAACGGAACAACATTATTACAGGTAGAAAGATTCATCAGTTGAGATT | 60 |

V11.01-11.10

| BB | 11.01 | 126 | TAAGAGCAACACTATCATAACCCTCGTTTACCAGACGACGATAAAAACCAAAATAGCGAG | 60 |
| BB | 11.02 | 127 | AGGCTTTTGCAAAAGAAGTTTTGCCAGAGGGGTAATAGTAAAATGTTTAGACTGGATAG | 60 |
| BB | 11.03 | 128 | CGTCCAATACTGCGGAATCGTCATAATATTCATTGAATCCCCCTCAAATGCTTTAAACA | 60 |
| BB | 11.04 | 129 | GTTCAGAAAACGAGAATGACCATAAATCAAAAATCAGGTCTTTACCCTGACTATTATAGT | 60 |
| BB | 11.05 | 130 | CAGAAGCAAAGCGGATTGCATCAAAAAGATTAAGAGGAAGCCCGAAAGACTTCAAATATC | 60 |
| BB | 11.06 | 131 | GCGTTTTAATTCGAGCTTCAAAGCGAACCAGACCGGAAGCAAACTCCAACAGGTCAGGAT | 60 |
| BB | 11.07 | 132 | TAGAGAGTACCTTTAATTGCTCCTTTTGATAAGAGGTCATTTTTGCGGATGGCTTAGAGC | 60 |
| BB | 11.08 | 133 | TTAATTGCTGAATATAATGCTGTAGCTCAACATGTTTTAAATATGCAACTAAAGTACGGT | 60 |
| BB | 11.09 | 134 | GTCTGGAAGTTTCATTCCATATAACAGTTGATTCCCAATTCTGCGAACGAGTAGATTTAG | 60 |
| BB | 11.10 | 135 | TTTGACCATTAGATACATTTCGCAAATGGTCAATAACCTGTTTAGCTAT | 49 |
| BB | 4.01 | 56 | TTGCCTGAGTAGAAGAACTCAAACTATCGGCCTTGCTGGTAATATCCAGAACAATATTAC | 60 |
| BB | 4.02 | 57 | CGCCAGCCATTGCAACAGGAAAAACGCTCATGGAAATACCTACATTTTGACGCTCAATCG | 60 |
| BB | 4.03 | 58 | TCTGAAATGGATTATTTACATTGGCAGATTCACCAGTCACACGACCAGTAATAAAAGGGA | 60 |
| BB | 4.04 | 59 | CATTCTGGCCAACAGAGATAGAACCCTTCTGACCTGAAAGCGTAAGAATACGTGGCACAG | 60 |
| BB | 4.05 | 60 | ACAATATTTTTGAATGGCTATTAGTCTTTAATGCGCGAACTGATAGCCCTAAAACATCGC | 60 |
| BB | 4.06 | 61 | CATTAAAAATACCGAACGAACCACCAGCAGAAGATAAAACAGAGGTGAGGCGGTCAGTAT | 60 |
| BB | 4.07 | 62 | TAACACCGCCTGCAACAGTGCCACGCTGAGAGCCAGCAGCAAATGAAAAATCTAAAGCAT | 60 |
| BB | 4.08 | 63 | CACCTTGCTGAACCTCAAATATCAAACCCTCAATCAATATCTGGTCAGTTGGCAAATCAA | 60 |
| BB | 4.09 | 64 | CAGTTGAAAGGAATTGAGGAAGGTTATCTAAAATATCTTTAGGAGCACTAACAACTAATA | 60 |
| BB | 4.10 | 65 | GATTAGAGCCGTCAATAGATAATACATTTGAGGATTTAGAAGTATTAGACTTTACAAACA | 60 |
| BB | 5.01 | 66 | CATTATCATTTTGCGGAACAAAGAAACCACCAGAAGGAGCGGAATTATCATCATATTCCT | 60 |
| BB | 5.02 | 67 | GATTATCAGATGATGGCAATTCATCAATATAATCCTGATTGTTTGGATTATACTTCTGAA | 60 |
| BB | 5.03 | 68 | TAATGAAGGGTTAGAACCTACCATATCAAAATTATTTGCACGTAAAACAGAAATAAAGA | 60 |
| BB | 5.04 | 69 | AATTGCGTAGATTTTCAGGTTTAACGTCAGATGAATATACAGTAACAGTACCTTTTACAT | 60 |
| BB | 5.05 | 70 | CGGGAGAAACAATAACGGATTCGCCTGATTGCTTTGAATACCAAGTTACAAAATCGCGCA | 60 |
| BB | 5.06 | 71 | GAGGCGAATTATTCATTTCAATTACCTGAGCAAAAGAAGATGATGAAACAAACATCAAGA | 60 |
| BB | 5.07 | 72 | AAACAAAATTAATTACATTTAACAATTTCATTTGAATTACCTTTTTTAATGGAAACAGTA | 60 |
| BB | 5.08 | 73 | CATAAATCAATATATGTGAGTGAATAACCTTGCTTCTGTAAATCGTCGCTATTAATTAAT | 60 |
| BB | 5.09 | 74 | TTTCCCTTAGAATCCTTGAAAACATAGCGATAGCTTAGATTAAGACGCTGAGAAGAGTCA | 60 |
| BB | 5.10 | 75 | ATAGTGAATTTATCAAAATCATAGGTCTGAGAGACTACCTTTTTAACCTCCGGCTTAGGT | 60 |
| BB | 6.01 | 76 | GAAAACTTTTTCAAATATATTTTAGTTAATTTCATCTTCTGACCTAAATTTAATGGTTTG | 60 |
| BB | 6.02 | 77 | AAATACCGACCGTGTGATAAATAAGGCGTTAAATAAGAATAAACACCGGAATCATAATTA | 60 |
| BB | 6.03 | 78 | CTAGAAAAAGCCTGTTTAGTATCATATGCGTTATACAAATTCTTACCAGTATAAAGCCAA | 60 |
| BB | 6.04 | 79 | CGCTCAACAGTAGGGCTTAATTGAGAATCGCCATATTTAACAACGCCAACATGTAATTTA | 60 |
| BB | 6.05 | 80 | GGCAGAGGCATTTTCGAGCCAGTAATAAGAGAATATAAAGTACCGACAAAAGGTAAAGTA | 60 |
| BB | 6.06 | 81 | ATTCTGTCCAGACGACGACAATAAACAACATGTTCAGCTAATGCAGAACGCGCCTGTTTA | 60 |
| BB | 6.07 | 82 | TCAACAATAGATAAGTCCTGAACAAGAAAAATAATATCCCATCCTAATTTACGAGCATGT | 60 |
| BB | 6.08 | 83 | AGAAACCAATCAATAATCGGCTGTCTTTCCTTATCATTCCAAGAACGGGTATTAAACCAA | 60 |

| Type | Identifier # | SEQ ID NO | Sequence | Sequence Length |
|---|---|---|---|---|
| BB | 6.09 | 84 | GTACCGCACTCATCGAGAACAAGCAAGCCGTTTTTATTTTCATCGTAGGAATCATTACCG | 60 |
| BB | 6.10 | 85 | CGCCCAATAGCAAGCAAATCAGATATAGAAGGCTTATCCGGTATTCTAAGAACGCGAGGC | 60 |
| Var | 1 | 136 | AACATCCAATAAATCATACAGGCAAGGCAAAGAATTAGCAAAATTAAGCAATAAAGCCTC | 60 |
| Var | 2 | 137 | GTGAGCGAGTAACAACCCGTCGGATTCTCCGTGGGAACAAACGGCGGATTGACCGTAATG | 60 |
| Var | 3 | 138 | TTCTTTTCACCAGTGAGACGGGCAACAGCTGATTGCCCTTCACCGCCTGGCCCTGAGAGA | 60 |
| Var | 4 | 139 | TCTGTCCATCACGCAAATTAACCGTTGTAGCAATACTTCTTTGATTAGTAATAACATCAC | 60 |
| Var | 5 | 140 | ATTCGACAACTCGTATTAAATCCTTTGCCCGAACGTTATTAATTTTAAAAGTTTGAGTAA | 60 |
| Var | 6 | 141 | TGGGTTATATAACTATATGTAAATGCTGATGCAAATCCAATCGCAAGACAAAGAACGCGA | 60 |
| Var | 7 | 142 | GTTTTAGCGAACCTCCCGACTTGCGGGAGGTTTTGAAGCCTTAAATCAAGATTAGTTGCT | 60 |
| Var | 8 | 143 | TCAACCGATTGAGGGAGGGAAGGTAAATATTGACGGAAATTATTCATTAAAGGTGAATTA | 60 |
| Var | 9 | 144 | GTATTAAGAGGCTGAGACTCCTCAAGAGAAGGATTAGGATTAGCGGGGTTTTGCTCAGTA | 60 |
| Var | 10 | 145 | AGCGAAAGACAGCATCGGAACGAGGGTAGCAACGGCTACAGAGGCTTTGAGGACTAAAGA | 60 |
| Var | 11 | 146 | TAGGAATACCACATTCAACTAATGCAGATACATAACGCCAAAAGGAATTACGAGGCATAG | 60 |
| Var | 12 | 147 | ATTTTCATTTGGGGCGCGAGCTGAAAAGGTGGCATCAATTCTACTAATAGTAGTAGCATT | 60 |

EXAMPLES

Example 1. Preparation of Biological Fluids

A. Hydroxyapatite (HA) Urine Purification

Human urine inherently contains DNA fragments, which can cause darkened backgrounds and unwanted bands to appear when run on a DNA staining gel. This effect is most noticeable in the vertical streaking that can be seen when urine samples are run. Hydroxyapatite packed columns can be used to purify DNA since it can loosely bind to DNA, the strength of this interaction can be adjusted by altering the phosphate concentration or pH levels in the eluting solutions. By running urine spiked with phosphate through these columns the problematic DNA fragments can removed with only minor losses of protein.

The following protocol was developed to prepare and purify urine samples prior to electrophoresis:

Column Prep: Add 1 mL of Sigmacote to clean and dry column. (water reacts with Sigmacote to form HCl). Spin and shake column to make sure it is evenly coated. Open stopcock and allow remaining Sigmacote to flow out. Let sit at least 15 minutes to allow the column to dry completely. Rinse the column 2× with a column full of DI-H2O. Add 1 mL of 10% w/v hydroxyapatite slurry gently to the bottom of the column using a P-1000 pipette. Let hydroxyapatite settle to the bottom with the stopcock closed. (approximately 5 minutes) There should be a clear distinction between the packed hydroxyapatite and the water above. Run a column-full of DI-H2O through the column 2× and let the column clear slowly by gravity, make sure the run off is clear (wash again if the run off is still cloudy).

Urine Purification: Add appropriate amount of 4M potassium phosphate (pH=7) solution to bring the final phosphate concentration in the urine to 0.1M. Add the urine to the column (200 μL minimum to keep the HA wet), with the stopcock closed. Open stopcock and apply a gentle pressure to the column to start flow. Collect in a protein low bind tube. (More pressure may be needed to collect the last of the solution in the column, and at low volumes pressure will likely be needed for the entire elution process). Clean column with bleach once done and hang upside down to dry completely before next use. An exemplary gel of urine samples purified using methods described herein is provided in FIG. 1, panel A.

B. Use of Metal Chelators

DNA nanoswitches can degrade in bodily fluids due to the presence of DNA degrading enzymes. Many of these enzymes require divalent ions such as $Mg^{2+}$ to function. Chelating metal ions (specifically magnesium) can thus help reduce the degradation of DNA nanoswitches in bodily fluids (e.g. blood, saliva, and urine). EDTA is a commonly used chelator in most biological contexts. Metal chelators such as EDTA, however, are highly pH dependent, as the chelators can only complex with metal ions when they are fully deprotonated. As seen in Equation 1 below, the chelating capacity of EDTA is dependent on both the formation constant of the specific metal ion and the fraction of EDTA in the fully deprotonated form, where $\alpha_Y 4-$refers to the fraction in the fully deprotonated form and $K_f$ is the formation constant of a chelator to a specific metal ion, $M^{n+}$. Each protonation state is referred to as a micro species.

$$\alpha_{Y4-} K_f = \frac{[MY^{n-4}]}{[M^{n+}][EDTA]}$$

Figure 1:
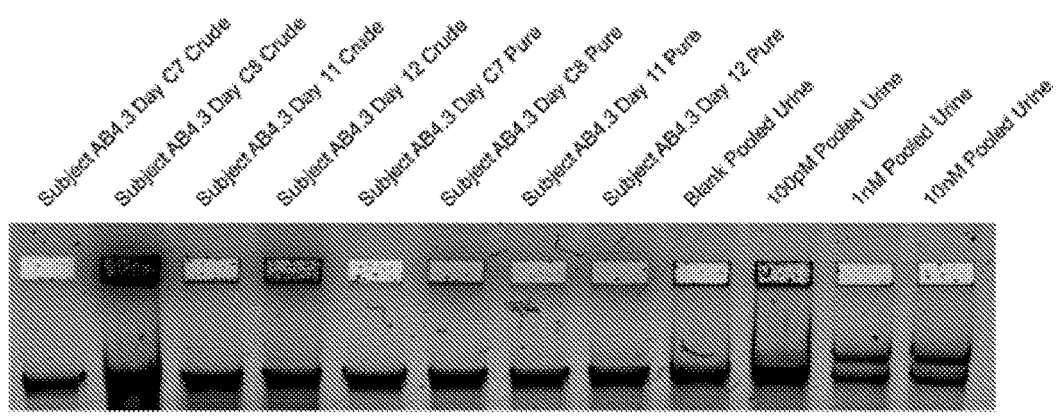
FIG. 1, panel A depicts results from a gel electrophoresis of crude and purified urine using methods described herein. Panel B provides various plots of the distribution of various micro-species and fully deprotonated species in the presence of different chelators.
Figure 1:
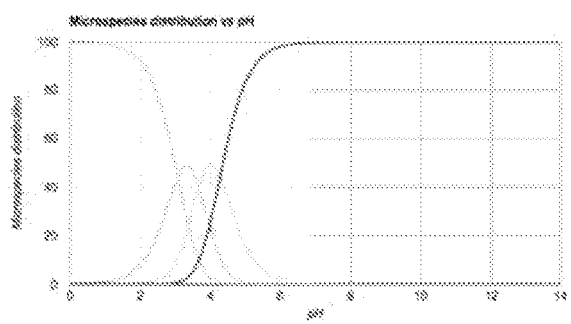
Figure 1:
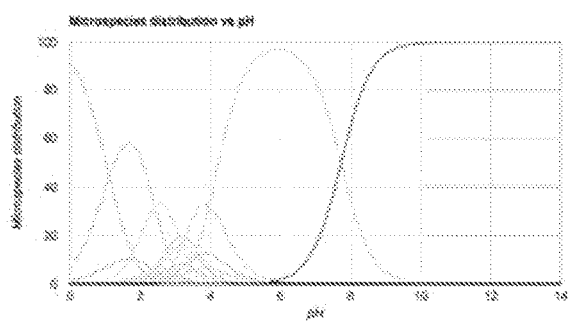
Figure 1:
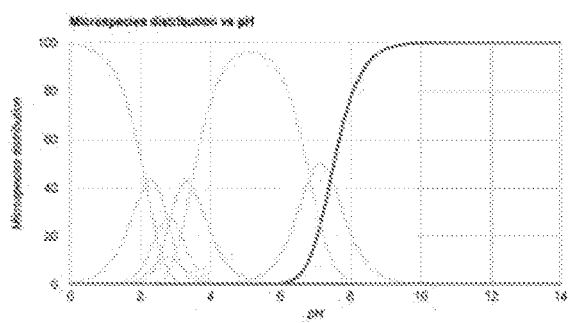
Figure 1:
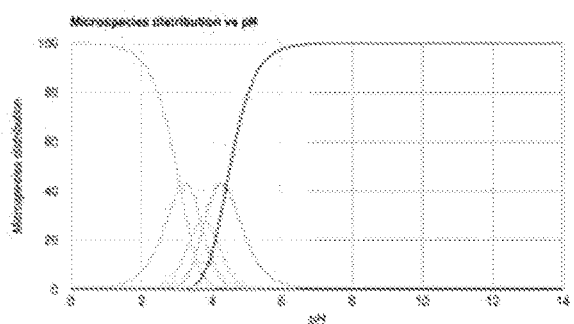

The fraction of fully deprotonated chelator is directly dependent on the pH of the solution and the pKa's of the chelator in question. This results in different distributions of micro species of each chelator as a function of pH. In FIG. 1, panel B, the various micro species and the fully deprotonated species are plotted.

While EDTA has proven very effective in urine and serum, different chelators can be used to chelate in solutions of lower pH when the fully deprotonated fraction of EDTA approaches zero. These micro species distributions of various chelators as well as their formation constants with Ca2+ and Mg2+ (two of the more prominent ions in urine and blood) are used to decide what chelators to be used in the context of different tests and test conditions in which pH may vary.

Example 2. Characterization of Different Biological Markers

A. Detection of Human Chorionic Gonadotropin (hCG) as a Pregnancy Test hCG is produced by the placenta following implantation, and is a widely known biomarker for the indication of pregnancy. Fully intact hCG consists of a dimer formed between two hCG subunits, beta-hCG and alpha-hCG. A DNA Nanoswitch (DNA NS) was developed to detect the presence of endogenous hCG in human urine using an antibody sandwich motif. A pair of antibodies which can simultaneously bind to hCG are functionalized to oligos which are hybridized onto the DNA NS scaffold. When hCG is present in solution, both antibodies can bind to an hCG molecule forming looped DNA NS's. This signal is detected using gel electrophoresis.

Listed below are exemplary antibody pairs that can be used to detect hCG (e.g. selecting one or two of the following to make a pair):

| ISOBMii Ab Codes | Owner | Owner Codes |
|---|---|---|
| 382 | Stenman | F16-6G5 |
| 383 | Medix | 5501 SP-1 |
| 384 | Stenman | F52-3F8 |
| 385 | Medix | 5503 SPI |
| 386 | Stenman | F94-8F8 |
| 387 | Medix | 5009 SP-5 |
| 388 | Medix | 5006 SP-5 |
| 389 | Stenman | F140-11C5 |
| 390 | Medix | 5008 SP-5 |
| 391 | Medix | 6601 SPR-5 |
| 392 | Stenman | F20-6E11 |
| 393 | Stenman | F52-3C11 |
| 394 | Medix | 5014 SPTN-5 |
| 395 | Abbott | 71752 |
| 396 | Stenman | F132-3C10 |
| 397 | Stenman | F142-7F3 |
| 398 | Stenman | F26-2G11 |
| 399 | Stenman | F95-5C4 |
| 400 | Abbott | 95658 |
| 401 | Stenman | F95-1E8 |
| 402 | Medix | 5004 SP-1 |
| 403 | Roche | M-INN2 |
| 404 | Stenman | F26-7E10 |
| 405 | Stenman | F95-1B2 |
| 406 | Medix | 5011 SPRN-1 |
| 407 | Stenman | F19-9C11 |
| 408 | Medix | 5016 SPRN-5 |
| 409 | Medix | 5012 SPRN-1 |
| 410 | Roche | M-BCG005 |
| 411 | Roche | M-1F7.9 |
| 412 | Siemens | 34/25.2.2 |
| 413 | Mologic | D101 |
| 414 | Paus | E26 |
| 415 | Siemens | 3A11 |
| 416 | Paus | E30 |
| 417 | Roche | M-INN22 |
| 418 | Siemens | 2F11 |
| 419 | Paus | E27 |
| 420 | Roche | M-94.139 |
| 421 | Siemens | 411/100.1.1.200.4.2 |
| 422 | Paus | E28 |
| 423 | Mologic | D102 |
| 424 | Siemens | 1G4 |
| 425 | Siemens | 5.00E+05 |
| 426 | Siemens | 16 E 2 |
| 427 | Siemens | 34A8.1.1 |
| 432 | Medix | 41-3-9 |
| 433 | Medix | 45A10 |
| 428 sheep | Mologic | 8F11 sheep |
| 429 sheep | Mologic | 9F10 sheep |
| 430 sheep | Mologic | 8G5 sheep |
| 431 sheep | Mologic | 618 sheep poly |
| 434a | INN | hCG111 |
| 435a | INN | hCG2 |
| 436a | INN | hCG40 |
| 437a | INN | hCG64 |
| 438a | INN | hCG53 |
| 439a | INN | hCG68 |
| 440a | INN | hCG26 |
| 441a | INN | bLH1 |
| 442a | INN | hCG58 |
| 443a | INN | hCG112 |
| 444a | INN | hCG106 |
| 445a | INN | hCG24 |
| 446a | INN | hCG45 |
| 447a | INN | hCG10 |
| 448a | INN | hCG103 |
| 449a | INN | hCG22 |
| 450a | Stahli | h54 |

Several important factors have been identified for choosing antibodies pairs which work successfully in urine. For example, the ability to simultaneously bind is a prerequisite. In addition, the antibodies should be able to bind to fully intact hCG as well as the beta subunit. Antibodies which have high affinities, but low on-rates, work but require long incubations. The following antibodies have been successfully used to detect endogenous hCG in human urine: INN-hCG-2, INN-hCG-22, 5008-SP5, 5014-SPTN5, and 5011 SPRN-1. Accordingly, an embodiment of the invention pertains to the use or one, or two of INN-hCG-2, INN-hCG-22, 5008-SP5, 5014-SPTN5, and 5011 SPRN-1, or functional fragments thereof.

B. Detection of Luteinizing Hormone for Identification of Ovulation

One of the biomarkers for the nanoswitch design is Luteinizing Hormone(LH)/Lutropin. LH is the primary biomarker used for identifying ovulation. This is due in large part to the surge that occurs approximately 1-3 days before ovulation. This LH Surge increases the baseline LH levels ten-fold and is the primary indicator for ovulation throughout industry.

The Luteinizing Hormone Nanoswitch is comprised of anti-LH antibodies (Fitzgerald 10-L15A and 10-L15B) conjugated to the 4.19M48 (L15B) and 4.44M40 (L15A) oligonucleotides through the Solulink process. The antibody-oligo conjugates are purified using the mag-bead process, and added to linear DNA to form the LH nanoswitch. This nanoswitch can be further purified using the Improved Recovery 5 k-9 k process on the SageScience BluePippin. The purified nanoswitch detected the LH Surge earlier than ClearBlue's Digital Ovulation Test according the following protocol:

1. Thaw one urine aliquot per test day
2. Invert multiple times and spin for 10 mins at 1,000×G
3. Pipet 30 μL of each sample into new tubes without disturbing pellet
4. Mix 1.77 μL BPIR NS+1 μL 5.4×TBE with EDTA+6 μL sample (500 pM NS)
5. 30 min incubation
6. 2.5 μL SYBR Load (2 μL Promega Loading Dye+0.5 μL 100× diluted SYBR Gold in TBE)
7. Load 10.6 μL into 0.7% agarose in 0.5×TBE with 1×SYBR Gold pre-stain
8. Run 30 mins at 200V in 0.5×TBE buffer
9. Image at 450 and 600 PMT.

Figure 2:
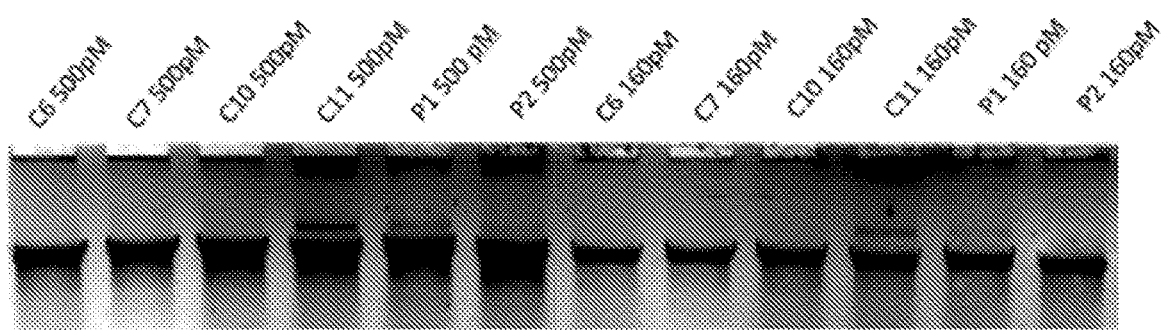
FIG. 2 depicts results of an LH detection using the nanoswitch described herein. C6 and C7 were the baseline days, C11 was the detected surge day prior to collection, and the concentrations refer to the final concentration of the nanoswitch.

An exemplary result of LH detection using the nanoswitch described herein is provided in FIG. 2.

It is contemplated that E3G (estrone-3-glucoronide) can also be used as a biomarker alongside LH. This could be used alongside or in place of the LH nanoswitch either on the same nanoswitch, mixed in the same lane, or run in a completely different lane.

C. Detection of Prostate Specific Antigen (PSA)

A PSA detector was synthesized by creating a standard antibody-oligo DNA Nanoswitch in which the DNA is functionalized with two antibodies that bind to two epitopes of a single antigen. The two antibodies used in this construct were: Anti-PSA 5001 (Medix) and Anti-PSA 5012 (Medix).

PSA antibodies were linked to oligos using the following protocol: Anti-PSA 5001 and Anti-PSA 5012 were conjugated to the following oligonucleotides: CTCAAATAT-CAAACCCTCAATCAATATCTGGTCAGTTGG (4.44; SEQ ID NO:1) and ACTATATGTAAATGCT-GATGCAAATCCAATCGCAAGACAAAGAAC (4.19; SEQ ID NO:2) using the Solulink™ Antibody-oligonucleotide conjugation kit (store.solulink.com/collections/antibody-oligonucleotide-products).

Anti-PSA-Oligo conjugates were purified with Protein A beads. A volume of Protein A beads equal to the volume of Antibody-oligo conjugate were washed 4 times with 10× volume of PBS (e.g., If processing 50 µL of Antibody-oligo conjugate 50 µL of Protein A beads would be washed 4 times with 500 µL of PBS). The antibody-oligo was applied to the beads and allowed to incubate for 40 minutes at room temperature. The beads were mixed every 10 minutes during the 40 minute incubation to prevent settling. The protein A beads were then washed three times with a 10× volume of PBS. An equal volume of Gentle Elution buffer was added to the Protein A beads and mixed every 5 minutes for 15 minutes. This elution step was then repeated again, and the fractions were combined and buffer exchanged into 10 mM sodium phosphate, 150 mM sodium chloride, 1 mM EDTA, 0.05% sodium azide, pH 7.2 buffer. Magnetic beads were used for faster processing as they can be easily pulled down with a magnet. However, this protocol could also be applied to centrifuged beads, or a flow column.

In order to hybridize anti-PSA 4.44 4.19 construct, 1.19 µL of 119 backbone mix (−4.44−4.19) was added to 5 µL of 20 nM linearized M13. The reaction mixture was heated to 95° C. for 2 minutes and brought down to 35° C. at 1° C./min. 5 µL of each PSA-Oligo conjugate was added and the mix was incubated at 35° C. for 10 mins and then 25° C. for 1 Hr 30 Mins and then held at 4° C. until use.

Purification of anti-PSA 4.44 4.19 construct was achieved by the following: 15 µL of KBB electrophoresis buffer and 10 µL of BluePippin™ loading solution were added to 15 µL of Anti-PSA 4.44 4.19 nanoswitch. The resulting mixture was BluePippin™ purified with the 0.75% Agarose S1 Improved Recovery with a Cut-off range of 5000-9000 bp.

Figure 3:
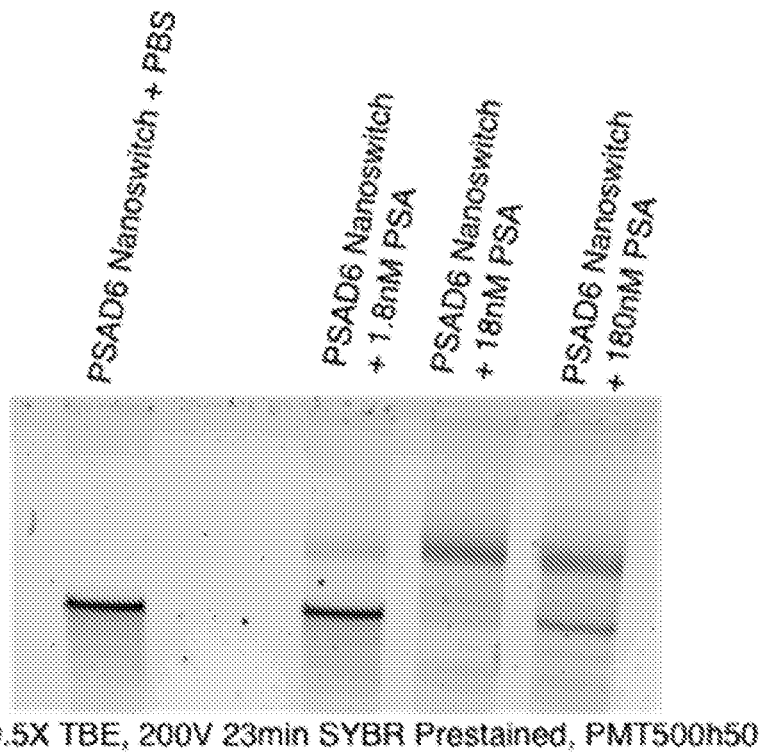
FIG. 3, panel A, shows PSA detection using crude PSA nanoswitch standard characterization. Panel B shows post-purified PSA nanoswitch with low PSA detection testing.
Figure 3:
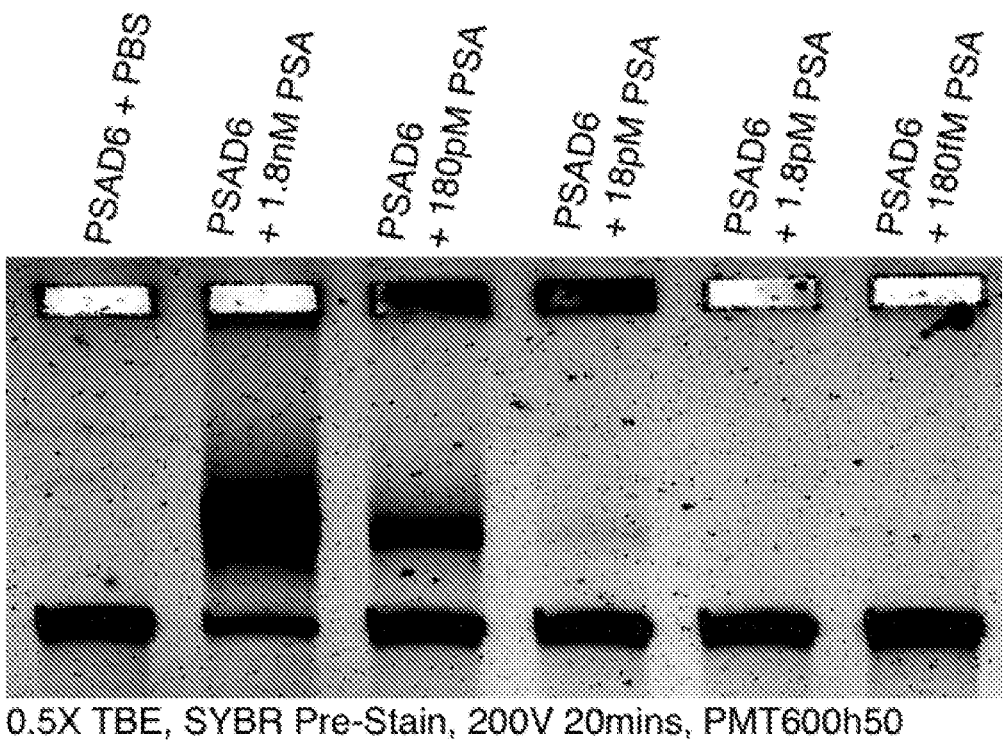

Exemplary results from PSA detection using methods described herein is provided in FIG. 3, panels A and B.

D. Detection of Herpes Simplex Virus (HSV)

A coupling strategy was developed for coupling small peptides where ordering a custom azide-modified peptide is possible. Specifically, the ring-strained alkyne, DBCO is functionalized onto oligonucleotides to enable copper-free click chemistry with an azide-functionalized peptide. This is particularly useful when making DNA nanoswitches for the detection of antibodies with known peptide antigens. Antibody detection is often done for serology testing in which one is looking to detect whether a person has ever been exposed to a certain pathogen (as the body creates antibodies against the pathogen resulting in a permeant record of the exposure).

In this example a nanoswitch was developed to detect the presence of antibodies against Herpes Simplex Virus 2 (HSV-2) (genital herpes) selectively over antibodies against Herpes Simplex Virus 1 (HSV-1) (oral herpes). The method of detection of Herpes Simplex Virus can be done by the detection of anti-HSV antibodies in blood or serum. By coupling 2 copies of an HSV antigen to the DNA nanoswitch, a single antibody which has two binding arms, can cause a nanoswitch to loop. See FIG. 4, panel A.

To prepare DBCO-functionalized oligos, 50 µL of 1 mM amine-functionalized oligo was buffer exchanged into 150 mM sodium chloride, 100 mM sodium phosphate (pH 8.0). A 2 mg vial of dry NHS-PEG4-DBCO, pulled from the freezer, was allowed to equilibrate to room temperature (this reduces risk of premature hydration resulting from condensation of ambient moisture on the cold walls of the container). The 2 mg of NHS-PEG4-DBCO was dissolved with 30.7 µL of anhydrous DMF resulting in 100 mM NHS-PEG4-DBCO. 5 µL of the 100 mM NHS-PEG4-DBCO was added to 50 µL of buffer exchanged amine-oligo and allowed to incubate for 1 Hr 30 min at ambient temperature. The resultant reaction mix was buffer exchanged into PBS resulting in ~1 mM DBCO-oligo. This was stored on ice until ready for use. The A309 and A260 were measured from stock and a 1:200 dilution and the molar substitution ratio (MSR) was approximated. A MSR<0.5 should be rejected from use. All buffer exchange steps were performed with Zeba Columns.

To prepare HSV-2 oligo conjugates using click-chemistry, azide-functionalized HSV-2 peptide ((Lys-N3; SEQ ID NO:3) RGTARTPPTDPKTHPHGPADAPPGSPAPPPPEH-RGGPEEFEGAGDGEPPEDDDS) (synthesized by LifeTein) was diluted to a final concentration 13.33 mM in PBS. 5 µL of 13.33 mM Azide-HSV-2 was added to 5 µL of 1 mM DBCO-4.44 and 5 µL of 13.33 mM Azide-HSV-2 was added to 5 µL of 1 mM DBCO-4.19 allowed to incubate overnight at ambient temperature. Purification of the HSV-2 oligo conjugates was next performed. Specifically, 1:100 dilution of HSV-2-Oligo conjugate was prepared. 30 µL each HSV-2-Oligo conjugate was BluePippin™ purified with a collection time range of 00 Hr:00 min:01 sec-01 Hr:40 min:00 sec.

To prepare the HSV-2 4.44 4.19 nanoswitch, 1.19 µL of 119 backbone mix (−4.44−4.19) was added to 5 µL of 20 nM linearized M13. The reaction mixture was heated to 95° C. for 2 minutes and brought down to 35° C. at 1° C./min. 5 µL of each purified HSV-2-Oligo conjugate was added and the mix was incubated at 35° C. for 10 mins and then 25° C. for 1 Hr 30 Mins and held at 4° C. Purification of the nanoswitch was next performed. Specifically, 15 µL of KBB electrophoresis buffer and 10 µL of BluePippin™ loading solution was added to 15 µL of HSV-2 4.44 4.19 nanoswitch. The resulting mixture was BluePippin™ purified with a 0.75% Agarose Dye-Free Marker 51 High-Pass 6-10 kb vs3 with a collection range set from 4,000 bp-50,000 bp.

Figure 4:
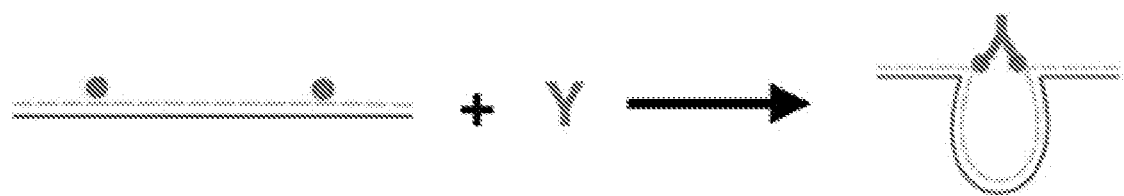
FIG. 4, panel A shows a schematic diagram of HSV-2 detection using the nanoswitch described herein. Panel B shows results using HSV-2 4.44 4.19 crude nanoswitch. Panel C shows results using BluePippin-purified HSV-2 antibody oligonucleotide ("oligo") crude construct. Panel D shows results using BluePippin purified HSV-2 antibody-oligos with BluePippin purified construct.
Figure 4:
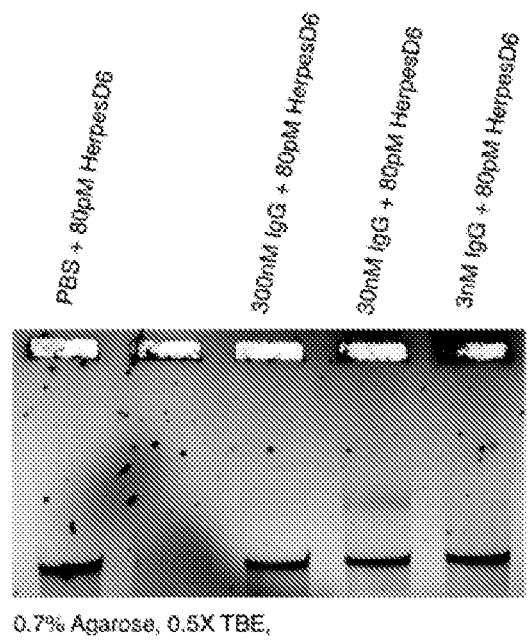
Figure 4:
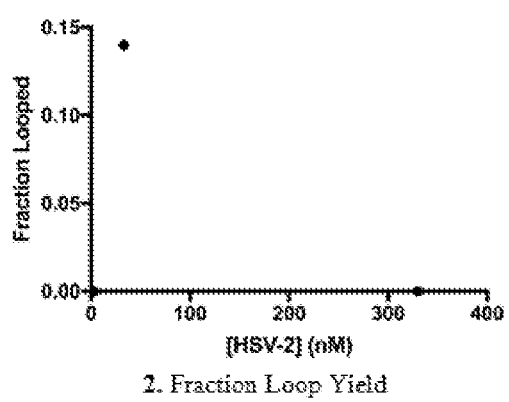
Figure 4:
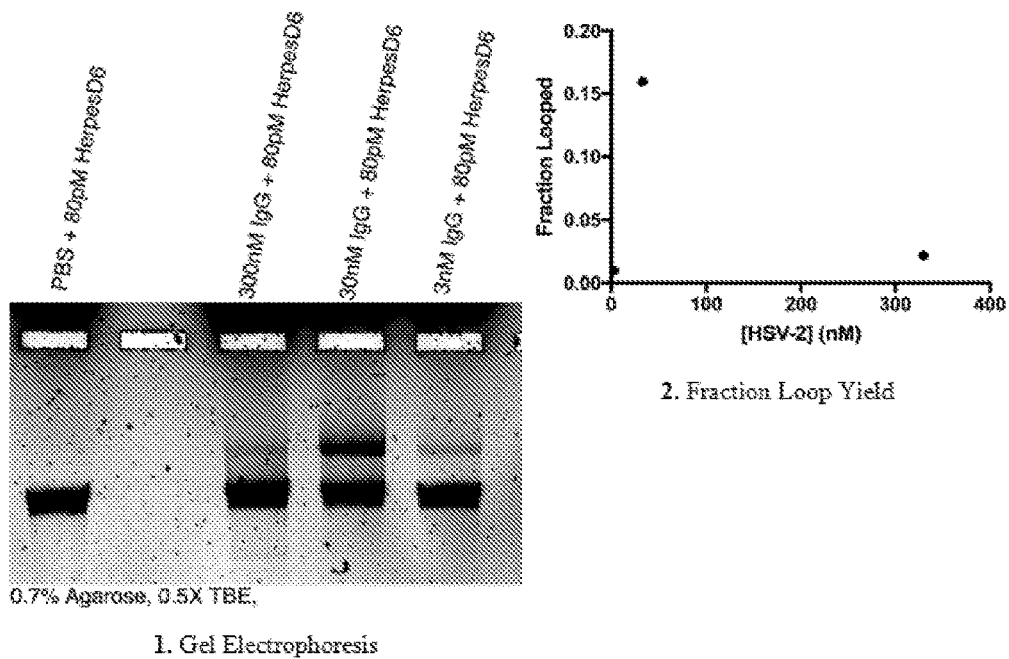
Figure 4:
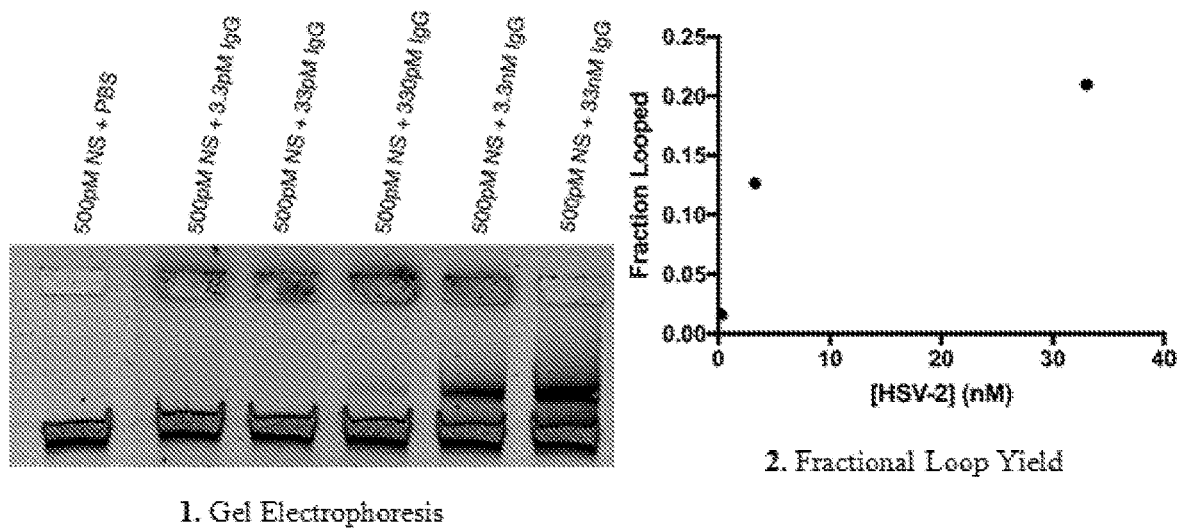

FIG. 4, panels B, C, and D show exemplary results for HSV-2 testing using the nanoswitch described herein.

E. Detection of *Streptococcus pyogenes* (Strep-A)

A nanoswitch against the group A *Streptococcus pyogenes* bacteria (Strep-A) was developed. For antibody-oligonucleotide coupling, rabbit anti-Strep-A, affinity purified polyclonal antibodies targeting the Strep-A antigen was purchased from Biospacific (www.biospacific.com/products/data/G47010.pdf). The antibodies were coupled to specific oligonucleotides (4.44 and 4.19) on the DNA nanoswitch. Monoclonal Anti-StrepA 2601 SPTN-5 (www.biospacific-.com/products/data/2601-100341.pdf) and Anti-StrepA 2603 SPTN-5 (www.biospacific.com/products/data/2603-100343.pdf) were conjugated on to 4.44 and 4.19, respectively. The antibodies are specific to Group A *Streptococcus pyogenes* with specificity to the cell-wall bound Strep-A antigen.

Figure 5:
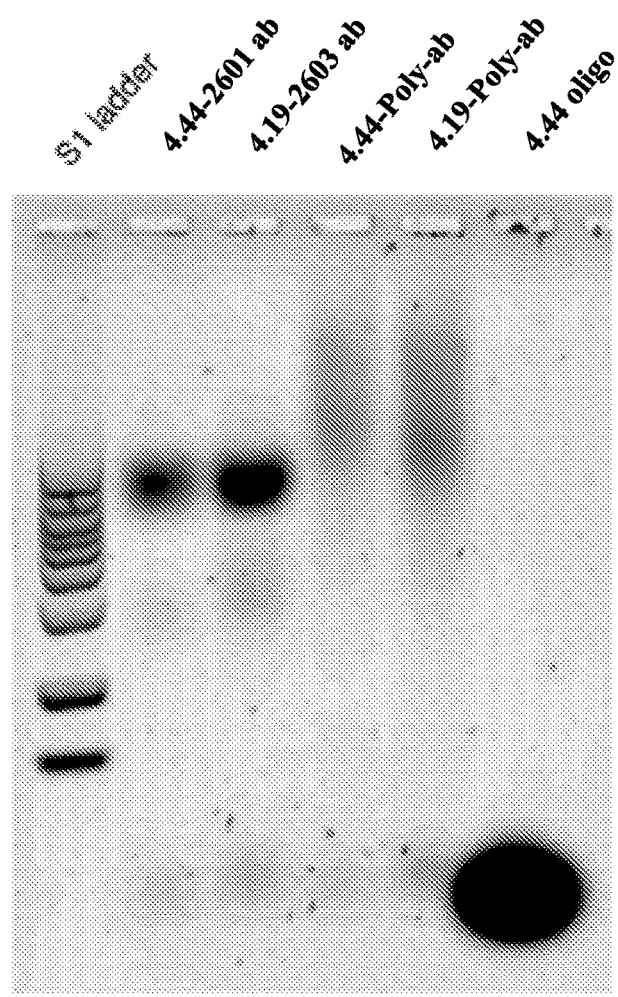
FIG. 5, panel A shows coupling of *Streptococcus Pyogenes* (Strep-A) antibody to oligonucleotides tested in 0.5× KBB electrophoresis buffer. Panel B shows detection of Strep-A antigen using Strep-poly construct. Panels C and D show issues of false positive bands. Panel E shows elimination of the false positive band through use of passivating agents. Panels F and G show detection of Strep-A in the presence of 0.1% BSA or 0.01% Tween20, respectively. Panel H depicts loop yields for the two conditions with different concentrations of the Strep-A antigen. Panel I shows repeatability of Strep-A detection using Strep-poly construct. Specifically, the construct (150 pM final concentration) was incubated with 0.01% Tween followed by incubation with different dilutions of the Strep-A antigen. The detection signal was analyzed for different dilutions of the Strep-A antigen as the intensity of the looped band (panel J) and as the % looped material (panel K). Panel L shows specificity of the nanoswitch in detecting Strep-A derived from the QuickVue Dipstick Strep-A test. Panels M and N shows detection of serially diluted Strep-A derived from the QuickVue Dipstick Strep-A test using the nanoswitch described herein compared to the QuickVue Dipstick. Panel O shows detection of Strep-A derived from the QuickVue Dipstick Strep-A test without any pH adjustment.
Figure 5:
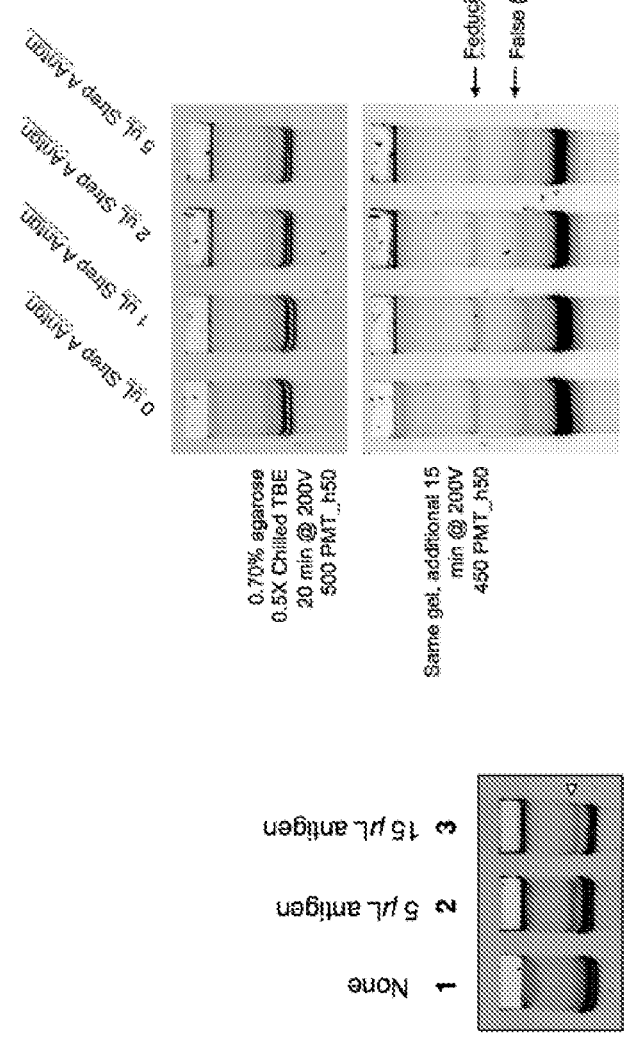
Figure 5:
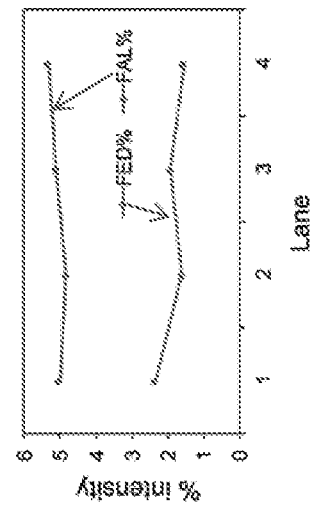
Figure 5:
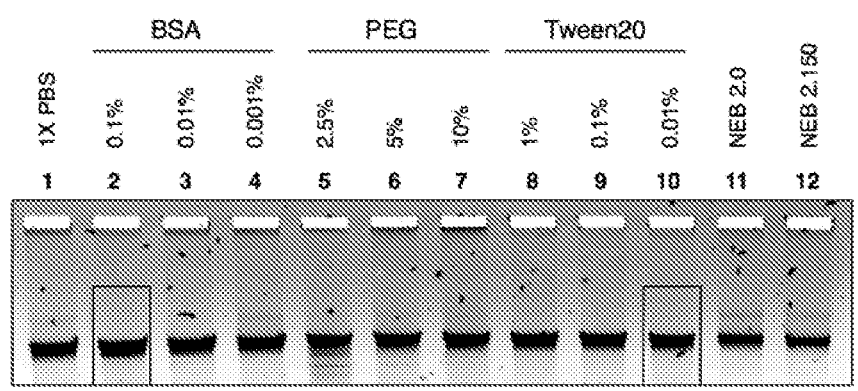
Figure 5:
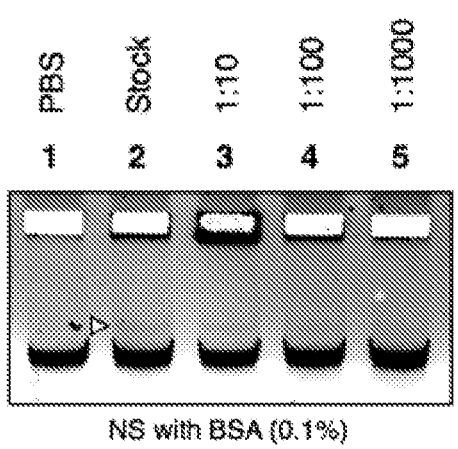
Figure 5:
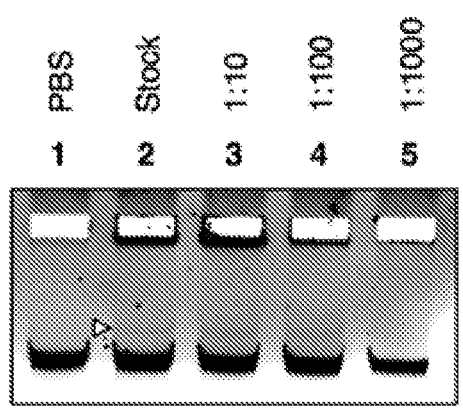
Figure 5:
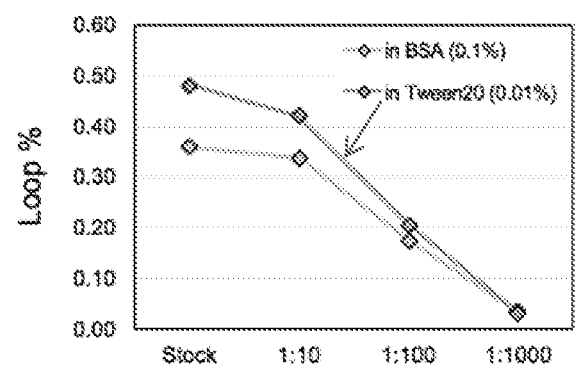
Figure 5:
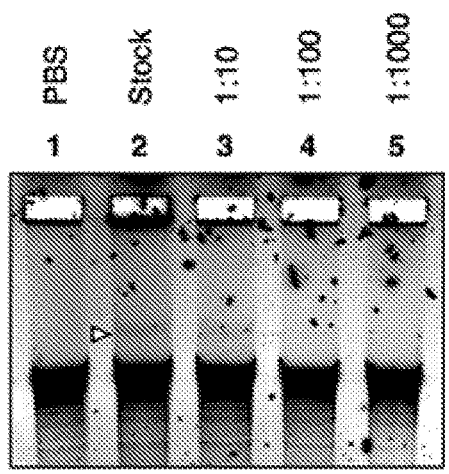
Figure 5:
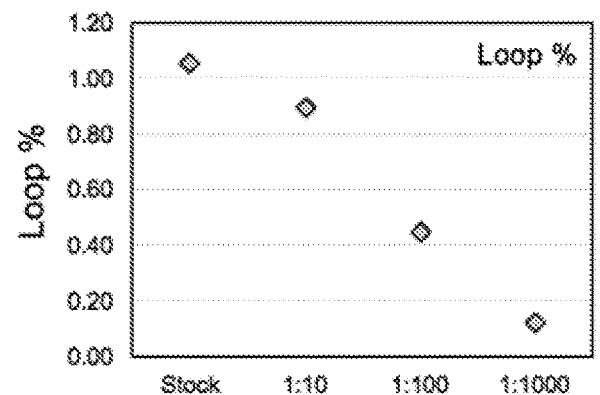
Figure 5:
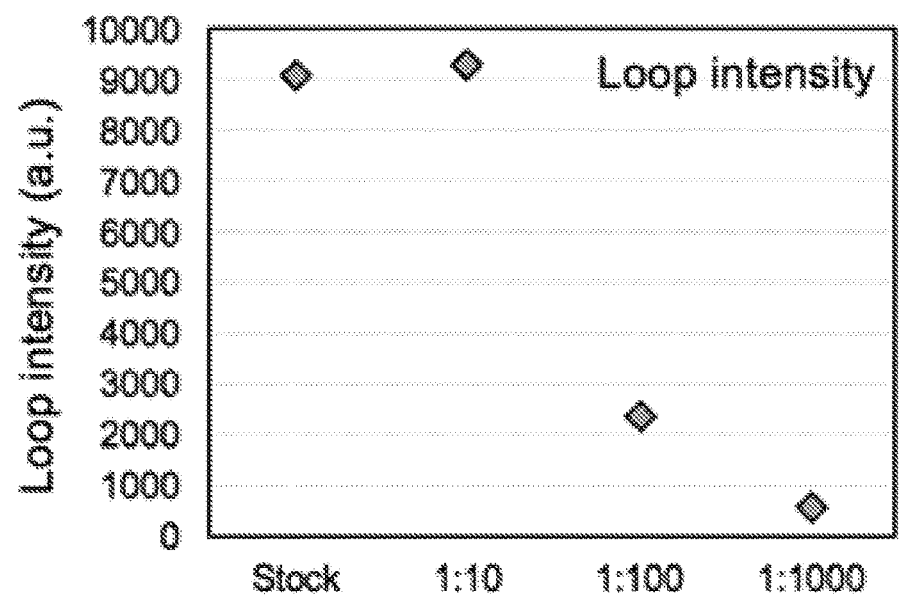
Figure 5:
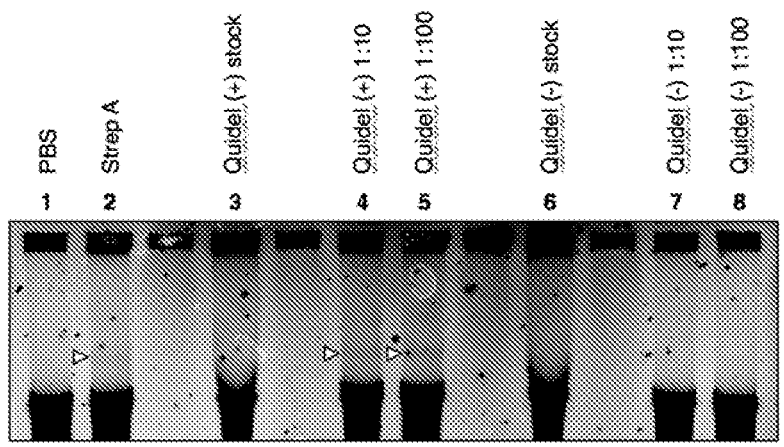
Figure 5:
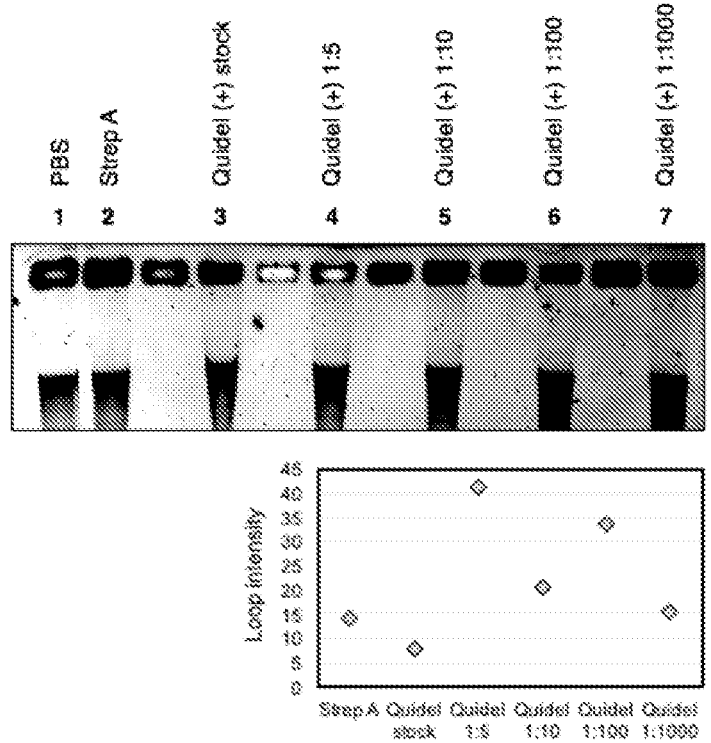
Figure 5:
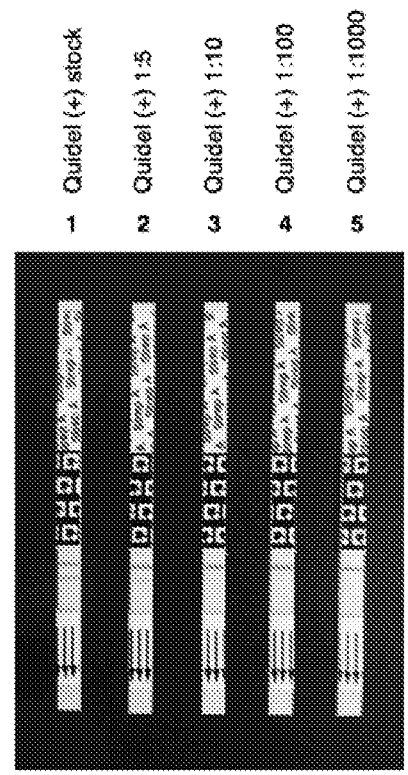
Figure 5:
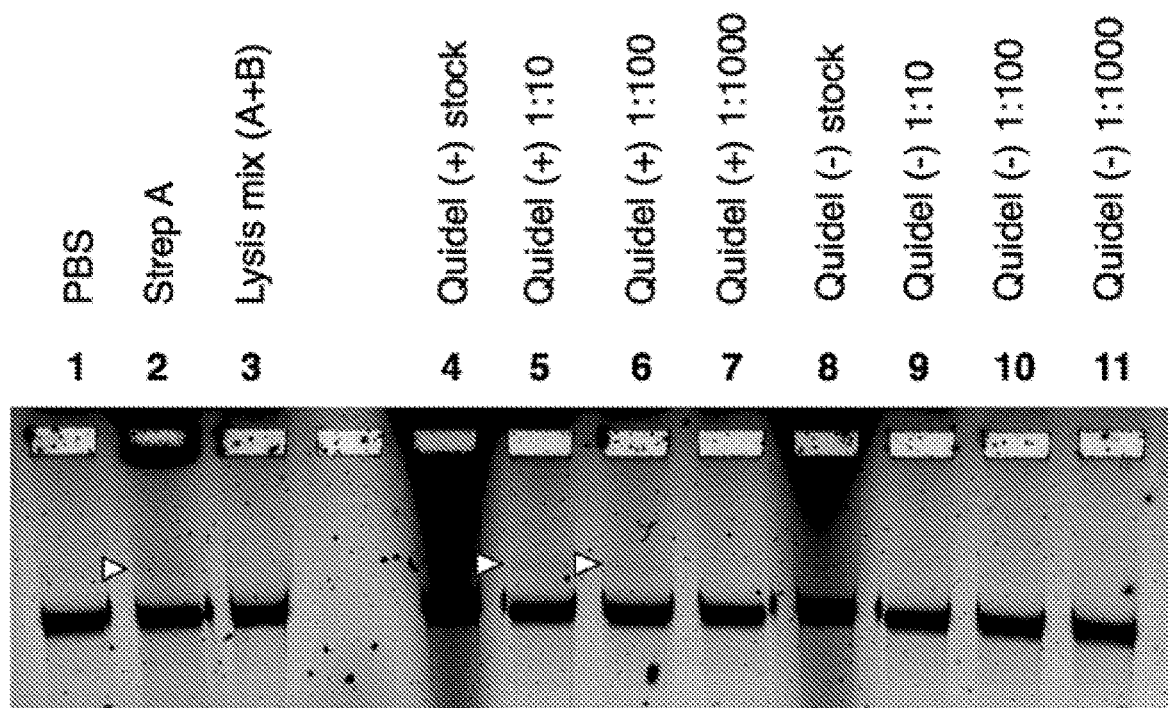

Antibody oligonucleotide conjugates were prepared using the SoluLink Antibody-Oligonucleotide All-in-One Conjugation Kit. In brief, specific amine-modified oligonucleotides were modified using an excess of the Sulfo-S-4FB linker, while the polyclonal antibody (100 µg) was modified using the S-HyNic linker, and the two molecules reacted together. The conjugates were then purified using magnetic-affinity solid phase strategy or using a BluePippin. The conjugates were tested on a 0.5×KBB electrophoresis buffer as indicated in FIG. 5, panel A. For detection of Step-A antigen using the strep-poly construct, the constructs were tested using a commercially available Strep-A antigen (Biospacific, Catalog number: J47000501 containing 2×108 organism/ml). Blue pippin purified constructs were incubated with different amounts of the Strep-A antigen for 2 hours at room temperature (see FIG. 5, panel B).

In some cases, aggregates lead to a "false positive" band (that migrates similar to a looped band) and a "fiducial band" that migrates slower than the looped band, when the constructs were incubated with Strep-A antigen for 2 hours at room temperature (See FIG. 5, panels C and D). To eliminate the false positive band, constructs were incubated with passivating agents to check for elimination of the false positive signal. Different concentrations of Tween, Bovine Serum Albumin (BSA) and poly ethylene glycol (PEG) were used to check for false positive elimination. 5 µL of the passivating agent was first added into protein lo-bind tubes followed by the addition of 5 µL of the construct. The mixture was left to incubate at room temperature for 30 mins. Out of these conditions, 0.1% BSA and 001% Tween20 (indicated in black boxes) resulted in complete elimination of false positives (See FIG. 5, panel E).

The functionality of the nanoswitch in passivating agents was tested. Specifically, the strep-poly construct was used to detect Strep-A antigen in the presence of the best passivating conditions. Detection of Strep-A (as a looped band) occurred in the presence of BSA, 0.1% (FIG. 5, panel F) and Tween20, 0.01% (FIG. 5, panel G). Loop yields for the two conditions with different concentrations of the Strep-A antigen is shown in (FIG. 5, panel H). In each case, 5 µL of the passivating agent was first added into protein lo-bind tubes followed by the addition of 5 µL of the construct. The mixture was left to incubate at room temperature for 30 minutes, followed by the addition of 10 µL of different dilutions of the Strep-A antigen and incubation at room temperature for 1 hour. Construct concentration used was 150 µM. Repeatability of Strep-A detection using Strep-poly construct was also assessed. FIG. 5, panel I, shows the construct (150 pM final concentration) was incubated with 0.01% Tween followed by incubation with different dilutions of the Strep-A antigen. The detection signal was analyzed for different dilutions of the Strep-A antigen as the intensity of the looped band (FIG. 5, panel J) and as the % looped material (FIG. 5, panel K). In each case, 5 µL of the passivating agent was first added into protein lo-bind tubes followed by the addition of 5 µL of the construct. The mixture was left to incubate at room temperature for 30 minutes, followed by the addition of 10 µL of different dilutions of the Strep-A antigen and incubation at room temperature for 1 hour.

A study was conducted to compare the nanoswitch to commercially available Strep detection kit. A commercially available kit, the QuickVue Dipstick Strep-A Test (see website located at www.quidel.com/immunoassays/rapid-strep-tests/quickvue-dipstick-strep-test), was used for detecting Group A streptococcal antigen from throat swabs. The kit contains two extraction reagents (reagent A: 4 M sodium nitrite and reagent B: 0.2 M acetic acid) that are mixed to form the 'lysis mixture'. The kit also contains a positive control (heat inactivated Group A *Streptococcus pyogenes*) and a negative control (heat inactivated Group C *Streptococcus*). Addition of positive or negative controls to the lysis mixture breaks open the cell wall releasing antigens. The strep-poly nanoswitch was used to detect Strep-A antigen from this mixture.

For preparation of the lysis mixture and positive/negative controls, 150 µL reagent A+150 µL reagent B followed by addition of 50 µL positive or negative control solution. The pH was adjusted to be around 7 using 1M NaOH and 25×PBS. In each case, 5 µL of the passivating agent was first added into protein lo-bind tubes followed by the addition of 5 µL of the construct. The mixture was left to incubate at room temperature for 30 mins, followed by the addition of 10 µL of different dilutions of the QuickVue positive/negative controls and incubated at room temperature for 1 hour. Detection was observed (as a looped band) only for the positive control and not the negative control demonstrating the specificity of the nanoswitch as shown in FIG. 5, panel L.

A dilution series for Quickvue controls was analyzed. The positive control from the Quickvue kit was diluted in PBS to test for limit of detection using the nanoswitch. The positive control mixture was prepared as described in FIG. 5 and was diluted to 1/5, 1/10, 1/100 and 1/1000 from the stock mixture. In each case, 5 µL of the passivating agent was first added into protein lo-bind tubes followed by the addition of 5 µL of the construct. The mixture was left to incubate at room temperature for 30 mins, followed by the addition of 10 µL of different dilutions of the QuickVue positive/negative controls and incubated at room temperature for 1 hour. The same dilutions were also tested on the Quickvue Dipstick for comparison. Similar dilutions were used, but a higher volume (40 uL) was placed in a tube and the dipstick was placed into the solution. Appearance of a blue line indicates that the dipstick is functional and appearance of a red line indicates Strep-A detection. The nanoswitch can detect up to 1:100 dilution of the positive control while the dipstick test shows the read out only up to 1:10 dilution. Results are shown in FIG. 5, panels M and N.

Detection of Quickvue controls without pH adjustment was carried out. The positive and negative controls from the Quickvue kit were prepared and buffer exchanged in to a 0.02% Tween solution (in PBS) and used as such without pH adjustment for detection. In each case, 5 µL of the passivating agent was first added into protein lo-bind tubes followed by the addition of 5 µL of the construct. 10 µL of different dilutions of the buffer exchanged QuickVue positive/negative controls were then added and incubated at room temperature for 1 hour. The lysis mixture (reagent A+B) without the positive or negative controls was used to check for any false positives. FIG. 5, panel O.

The DNA nanoswitches described herein (e.g., in an antibody-sandwich configuration—two antibodies on a nanoswitch binding to a single antigen) can be used to detect additional diseases and conditions. Specifically, the following pairs of antibodies are used to detect infection with Gonorrhea and Chlamydia as well as diseases/conditions including diabetes and inflammation:

| Company | Product | Antigen |
|---|---|---|
| Chlamydia: | | |
| Medix | Anti-Chlamydia 6701 SP-5 | Chlamydial LPS KDO-trisaccharide |
| Medix | Anti-Chlamydia 6703 SPRN-5 | Chlamydial LPS KDO-trisaccharide |
| Medix | Anti-Chlamydia 6703 SPRN-5 | Chlamydial LPS KDO-trisaccharide |
| Abcam | Ab20881 | major outer membrane protein |
| Abcam | ab20767 | major outer membrane protein |
| Abcam | ab41193 | major outer membrane protein |
| Gonorrhea: | | |
| Abcam | ab19962 | all antigens of *Neisseria gonorrhoeae* |
| Abcam | ab62964 | major outer membrane protein |
| Abcam | ab40998 | N/A |
| Abcam | ab21096 | N/A |
| Diabetes | | |
| Abcam | ab31152 | Hemoglobin A1C |
| Abcam | ab31151 | Hemoglobin A1C |
| Abcam | ab33847 | Hemoglobin A1C |
| Abcam | ab131229 | Hemoglobin A1C |
| Abcam | (ab130119) | Hemoglobin A1C |
| Abcam | (ab33615) | Hemoglobin A1C |
| Inflammation | | |
| Medix | CRP 6402 SPTN-5 | C-Reactive Protein |
| Medix | CRP 6403 SPTN-5 | C-Reactive Protein |
| Medix | CRP 6404 SP-2 | C-Reactive Protein |
| Medix | CRP 6404 SP-6 | C-Reactive Protein |
| Medix | CRP 6405 SPTN-5 | C-Reactive Protein |
| Medix | CRP 6407 SPTN-5 | C-Reactive Protein |

Example 3. Improvement of Coupling Chemistry

For coupling of various antibodies to oligonucleotides, the Solulink antibody-oligonucleotide conjugation kit (Cat. No. A-9202-001) was used in accordance with manufacturer's instructions. In an embodiment, the purification is performed using BluePippin instead of magnetic beads as recommended by the manufacturer. Specifically, use of this kit involved four mains steps for coupling:
1. An amine-modified, 20 to 60-mer oligonucleotide is modified using an excess of the Sulfo-S-4FB-linker. This reactive NHS-ester incorporates a 4FB (aromatic aldehyde functional group, formylbenzamide) at the desired terminus of the oligonucleotide.
2. Polyclonal or monoclonal antibody (100 µg) is modified using the S-HyNic linker. This NHS-ester reacts with lysine residues, incorporating HyNic functional groups (hydrazino-nicotinamide) onto the antibody.
3. The two modified biomolecules are mixed together in the presence of the TurboLink™ catalyst, aniline, leading to rapid and efficient conversion of the antibody to conjugate through formation of stable bis-arylhydrazone bonds,
4. Magnetic-affinity, solid phase purification.

Alternatively, coupling was carried out using the Innova antibody-oligonucleotide conjugation kit (i.e., Thunder-Link Plus or Thunder-Link) in accordance with manufacturer's instructions. Use of this kit involved four main steps:
1. Oligo Activation
2. Antibody Activation
3. Oligo-Antibody Coupling
4. Purification An alternative to covalently coupling a protein to an oligo is the use of biotin-streptavidin, one of the strongest non-covalent interactions. In this regard, the Innova Lightning-Link Streptavidin kit was used, in accordance with manufacturer's instructions, which can attach a streptavidin molecule to an antibody or protein. The protein can subsequently be mixed with a biotin functionalized oligo, to create a protein/Antibody oligo conjugate. This also allowed for quick and modular assembly as any streptavidinated antibody can be added to any biotinylated oligonucleotide.

In addition to the commercial kits, additional coupling methods were developed for coupling antibodies to oligos.

DBCO-Functionalized IgG Coupling to Azide-Modified Oligo

This coupling method utilizes copper-free click chemistry to functionalize antibodies, peptides, or proteins to oligos. First, the antibody, peptide, or protein can be activated with a ring-strained alkyne such as Dibenzocyclooctyne (DBCO) utilizing a NHS-DBCO linker to target free amines. DBCO can then be used to react with an azide-functionalized oligo.

To prepare DBCO-functionalized IgG, 50 µL of 5 mg/mL antibody were buffer exchanged into Activation Buffer (150 mM sodium chloride, 100 mM sodium phosphate, pH 8.0). A 2 mg vial of dry NHS-PEG4-DBCO, pulled from the freezer, was allowed to equilibrate to room temperature (this reduces risk of premature hydration resulting from condensation of ambient moisture on the cold walls of the container). The 2 mg of NHS-PEG4-DBCO was dissolved with 50 µL of anhydrous DMF. These 50 µL were immediately added to 250 µL Activation Buffer resulting in 300 µL of 10 mM NHS-PEG4-DBCO. 5 µL of the 10 mM NHS-PEG4-DBCO was added to 50 µL of the buffer exchanged IgG (from above), and allowed to incubate for 1 Hr 30 min at room temperature. This results in 30 DBCO molecules for each antibody, for antibodies of at lower concentrations the concentration DBCO can be scaled accordingly. The resultant reaction mix was buffer exchanged into PBS and stored at 4° C. until ready for use. All buffer exchange steps were performed using Zeba 7K MW cutoff columns.

To synthesize IgG-oligo conjugates, azide-modified oligo was diluted to 1 mM in nuclease-free water. 5.5 µL of 1 mM azide oligo was added to 55 µL of DBCO-functionalized IgG. The reaction was allowed to incubate overnight at room temperature. The resultant reaction mixture was buffer-exchanged into 150 mM sodium chloride, 1 mM EDTA, 0.05% sodium azide, 10 mM sodium phosphate (pH 7.2).

Azide-Modified Peptide Coupling to DBCO-Functionalized Oligo

A DNA nanoswitch that is used to detect an antigen is functionalized with of a pair of antibodies that can simultaneously bind to the antigen. However, if the detection of an antibody is required the DNA nanoswitch should be functionalized with two antigens (typically proteins) that can bind to a single antibody. The creation of protein-oligo conjugates typically utilizes NHS-based chemistry to append reactive groups to the protein. In some instances, this can be problematic if the protein contains few/no surface exposed lysines. One solution to this issue is to synthesize a short peptide of the antibody binding region on the protein. During peptide synthesis a functional residue can be added to the peptide. This ensures that each peptide can be coupled to an oligo. Another advantage of the use of peptides is that they can be suspended at extremely high molar concentration as compared to larger protein resulting in better reaction kinetics and yields. A method was developed which resulted in creation of a peptide oligo conjugate where the peptide was synthesized with a terminal azide. This could be coupled to a DBCO-modified oligo via copper free click chemistry.

Specifically, to prepare DBCO-functionalized oligo, 50 μL of 1 mM amine-functionalized oligo was buffer exchanged into 150 mM sodium chloride, 100 mM sodium phosphate (pH 8.0). A 2 mg vial of dry NHS-PEG4-DBCO, pulled from the freezer, was allowed to equilibrate to room temperature (this reduces risk of premature hydration resulting from condensation of ambient moisture on the cold walls of the container). The 2 mg of NHS-PEG4-DBCO was dissolved with 30.7 μL of anhydrous DMF resulting in 100 mM NHS-PEG4-DBCO. 5 μL of the 100 mM NHS-PEG4-DBCO was added to 50 μL of buffer exchanged amine-oligo and allowed to incubate for 1 Hr 30 min at ambient temperature. The resultant reaction mix was buffer exchanged into PBS resulting in ~1 mM DBCO-oligo. This was stored at 4° C. until ready for use. The A309 and A260 of a 1:200 dilution can be used to estimate the fraction of oligo which has a DBCO successfully coupled. All buffer exchange steps were performed with Zeba Columns.

Preparation of peptide-oligo conjugates for click chemistry was performed in which azide-functionalized peptide was diluted to a final concentration 13.33 mM in PBS. 5 μL of 13.33 mM Azide-Peptide was added to 5 μL of 1 mM DBCO-oligo and allowed to incubate overnight at ambient temperature.

Figure 6:
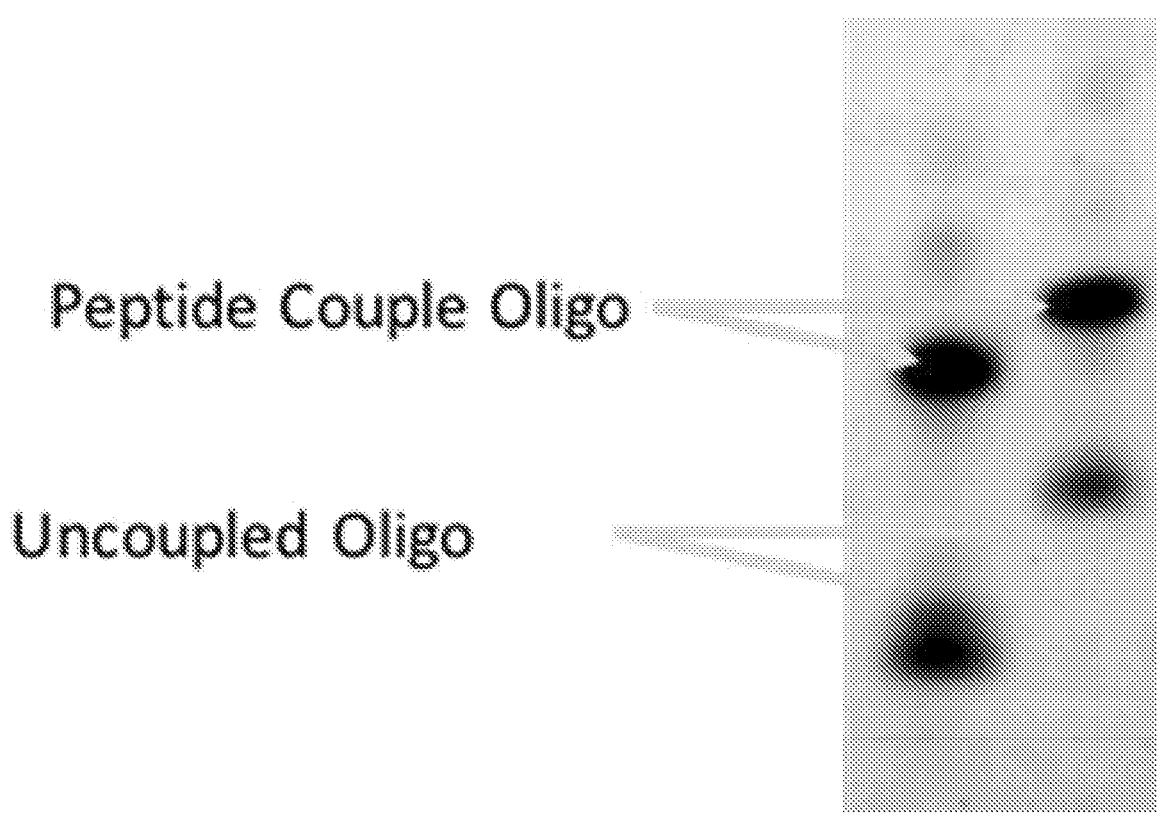
FIG. 6 shows characterization of a peptide coupled to two different oligo sequences as described in Example 3. The peptide conjugated oligonucleotides ran higher in the gel than the unconjugated oligo.

In order to purify the peptide-oligo conjugates, a 1:100 dilution of Peptide-Oligo conjugate was prepared. 30 μL each Peptide-Oligo conjugate was BluePippin™ purified using the 0.75% DF 3-10 kb Marker 51 Improved recovery cassette with a time range of 00 Hr:00 min:01 sec-01 Hr:40 min:00 sec. Conjugates were characterized on a 4-20% polyacrylamide gel as shown in FIG. 6.

Glycosylation-targeting Oligo-IgG Coupling Strategy

Figure 7:
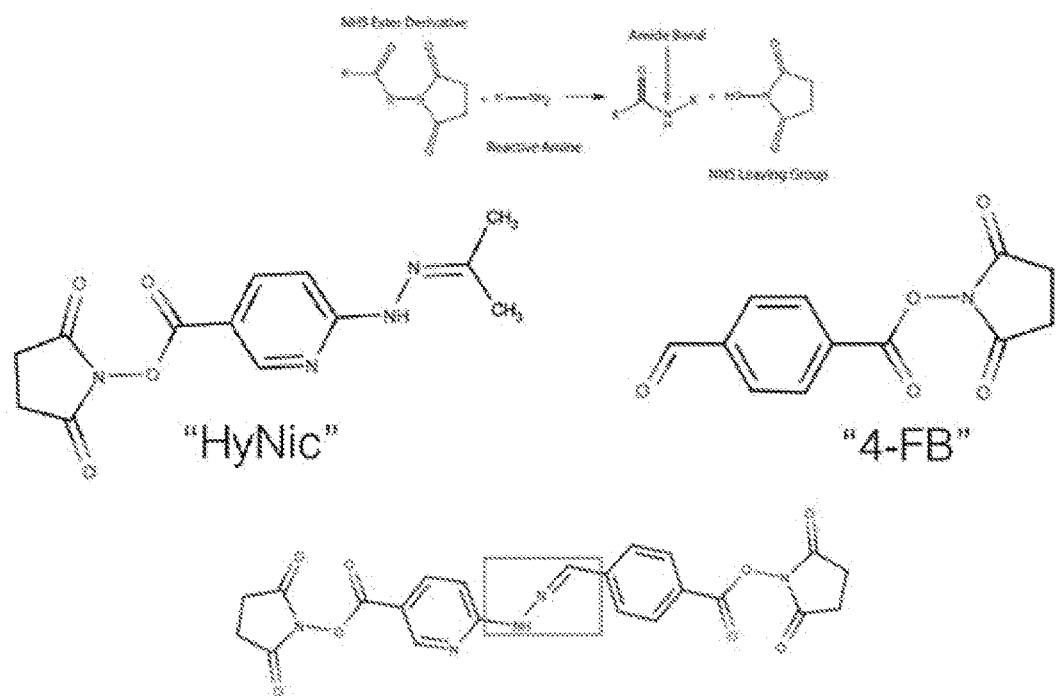
FIG. 7, panel A, depicts a schematic of NHS-based coupling strategy for hydrazone linkage of antibodies to oligonucleotides. Panel B depicts common antibody glycosylation patterns. The glycosylation pattern of the antibody determines which residues can be targeted for activation. Panel C shows activation of reactive aldehydes through the oxidation of glycosylation sites. Panel D shows hydrazone-linkage coupling strategy. Panel E depicts a gel electrophoresis of the hydrizide-oligo formed by methods described herein.
Figure 7:
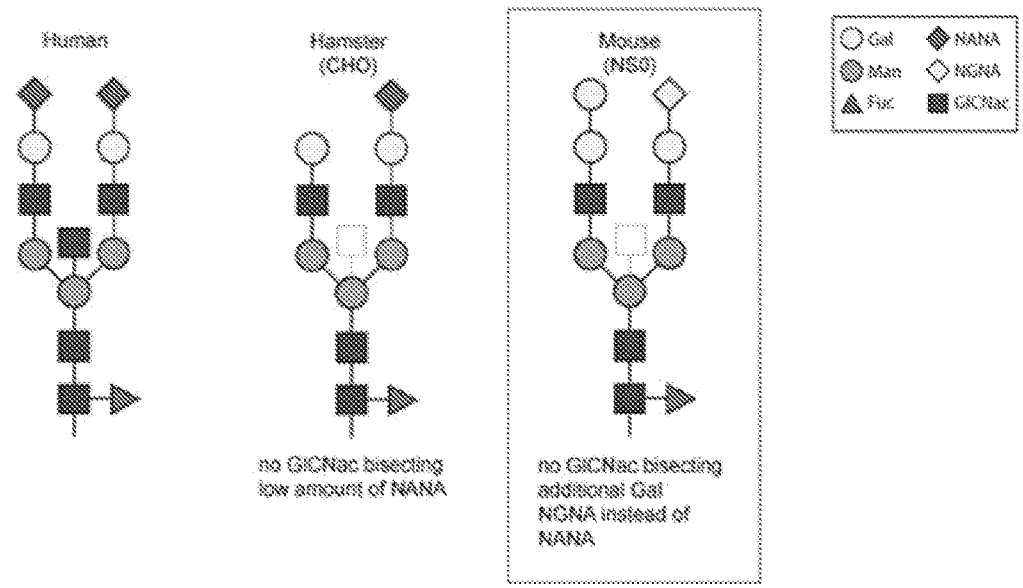
Figure 7:
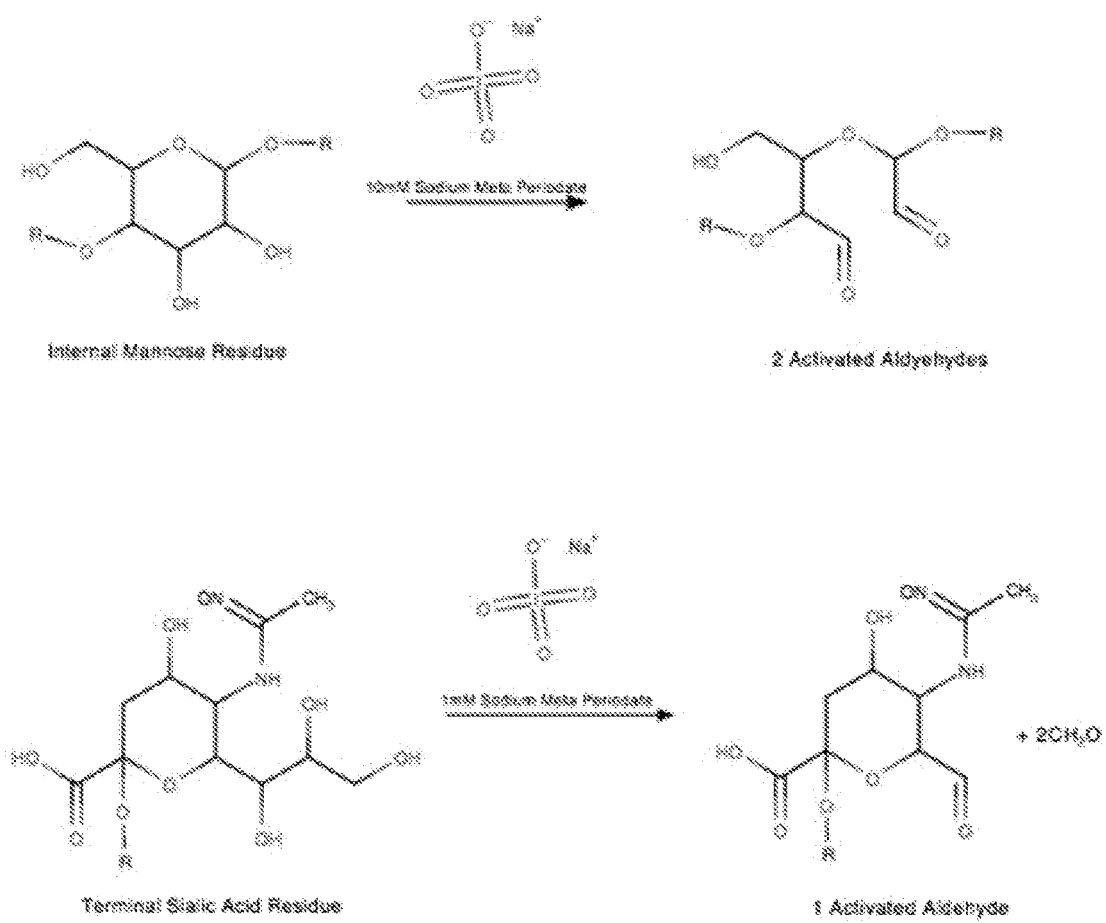
Figure 7:
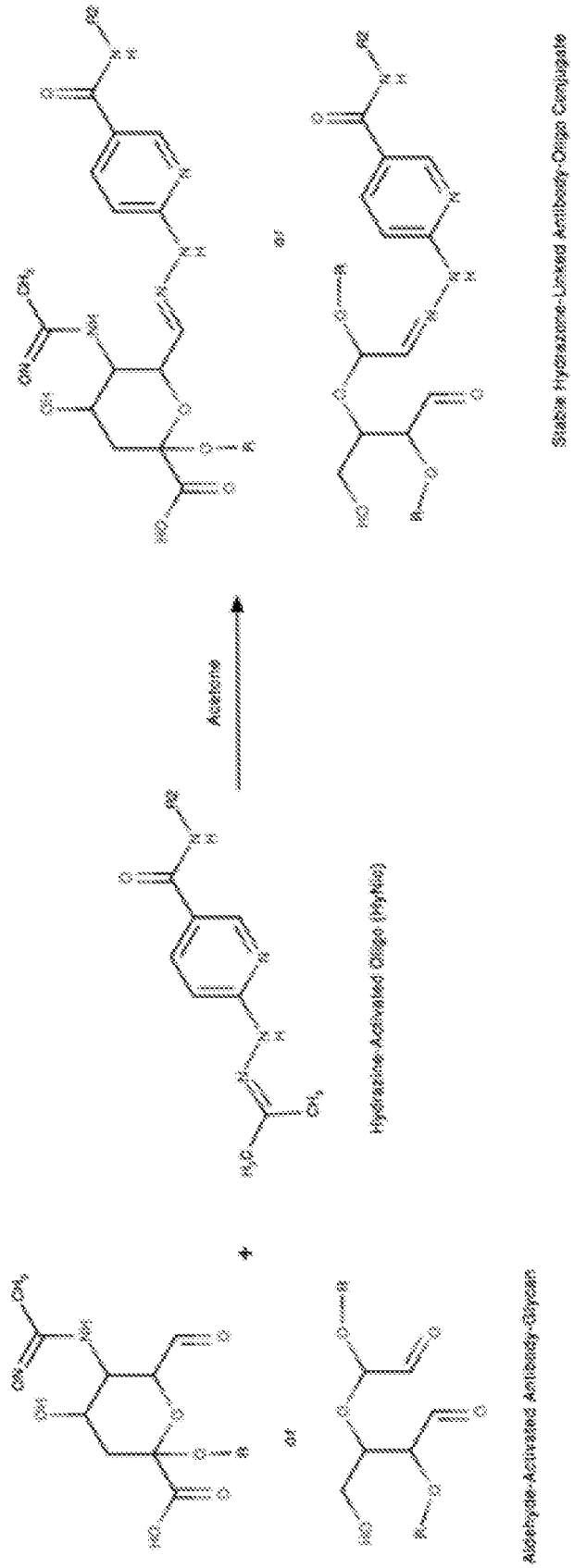
Figure 7:
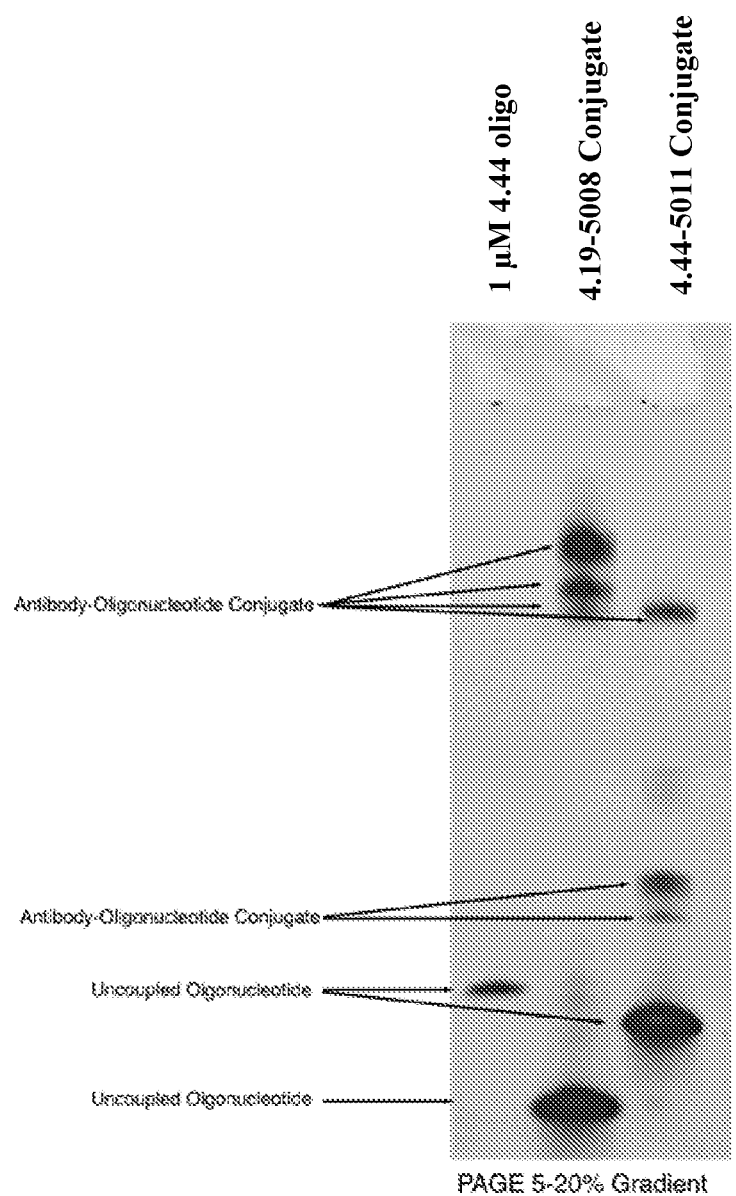

The coupling strategy that was used most for oligo-IgG coupling was a purely amine-based targeting strategy that relies on NHS coupling of reactive linkers as provided in FIG. 7, panel A. As NHS coupling can react with any exposed lysine residue, this method has the risk of chemically modifying the binding pocket of the antibody resulting in steric hindrance that may reduce or abolish the antibodies ability to bind to its antigen. However, by targeting antibody-glycosylation sites in the CH2 heavy-chain region of an IgG, it is believed that the binding pocket may remain free of chemical modification. FIG. 7, panel B provides a schematic of common antibody glycosylation patterns.

A new coupling strategy was developed which employed the oxidation of sugar residues, specifically terminal sialic acid and internal mannose residues. Using a gentle oxidizer (such as sodium meta-periodate) allowed for the conversion of cis-diols to aldehydes groups that can react with hydrizides to create a hydrazine (see FIG. 7, panels C and D).

The first step of the coupling strategy involved activation of the hydrizide-oligo. Specifically, lyophilized oligo was suspended to 1 mM in Oligo Activation Buffer (150 mM sodium chloride, 100 mM sodium phosphate pH 8.0). If the oligo was already suspended it was buffer exchanged into Oligo Activation Buffer. One half volume equivalent of anhydrous DMF was added to the oligo. NHS-Hydrizide (Solulink, S-1002-105) was dissolved in Anhydrous DMF to a concentration of 137 mM (1 mg HyNic (290.27 g/mol) in 25 μL DMF). This was diluted into the oligo solution such that there were 25 mole-equivalents of NHS-Hydrizide per oligo. For example: If using 20 μL of 1 mM oligo (20 nmoles), 10 μl of DMF would be added, followed by 3.65 μL of 137 mM HyNic (500 nmoles). The reaction was allowed to incubate for two hours at ambient temperature. The resulting reaction mixture was buffer-exchanged into Coupling Buffer (150 mM sodium chloride, 30 mM aniline, 100 mM sodium phosphate (pH 6.0) using a Zeba column. This resulted in approximately 600 uM oligo that can be stored for later use at −20° C. for up to 2 weeks.

Oxidation of IgG glycosylation sites was then carried out. Stock IgG (1-5 mg/ml) solution was buffer exchanged into Antibody Oxidation Buffer (0.1M sodium acetate buffer, pH 5.5). Sodium metaperiodate was suspended, in a dark tube, to a concentration of 100 mM in Antibody Oxidation Buffer. The sodium metaperiodate solution was added to the IgG solution to a final concentration of 10 mM sodium metaperiodate (e.g. 1 μl of 100 mM sodium metaperiodate+9 μl of IgG). The reaction was allowed to incubate at room temperature in the dark for 30 minutes. The final reaction mixture was buffer-exchanged into 150 mM sodium chloride, 100 mM sodium phosphate (pH 6.0).

Lastly, hydrazone linkage of oxidized IgG to hydrizide-oligo was performed. 10× volume of oxidized IgG was added to 1× volume of hydrizide oligo (e.g. 10 μl of oxidized IgG (~6-30 μM) could be added to 1 μl of hydrazide oligo (~600 uM)). The reaction was incubated at room temperature for 2 hours. The final reaction was buffer-exchanged into 10 mM sodium phosphate, 150 mM sodium chloride, 1 mM EDTA, 0.05% sodium azide, pH 7.2. FIG. 7, panel E, depicts a gel electrophoresis of the hydrizide-oligo formed by methods described herein.

Example 4. Improvement of End User Tests

Combining Ovulation and Pregnancy Testing Into One Test Stick

Currently people purchase ovulation predictor kits (OPKs) and pregnancy tests (PTs) as separate tests. OPKs measure Luteinizing Hormone (LH) as ovulation follows shortly after spikes in LH. Thus OPKs are used to help time intercourse to maximize chances of conceiving. An example of OPK is ClearBlue made by Swiss Precision Diagnostics. After having intercourse people then purchase PTs to determine if they were successful in having a fertilized embryo implant. PTs measure beta-human Chorionic Gonadotropin (β-hCG) which is produced by the developing embryo. β-hCG levels as much as quadruple daily making it easy to detect 4-5 days prior to a woman's expected missed period. An exemplary PT is First Response which is a very sensitive test (the most sensitive on the market) that can detect β-hCG in urine 6 days prior to a woman's expected missed period.

Figure 8:
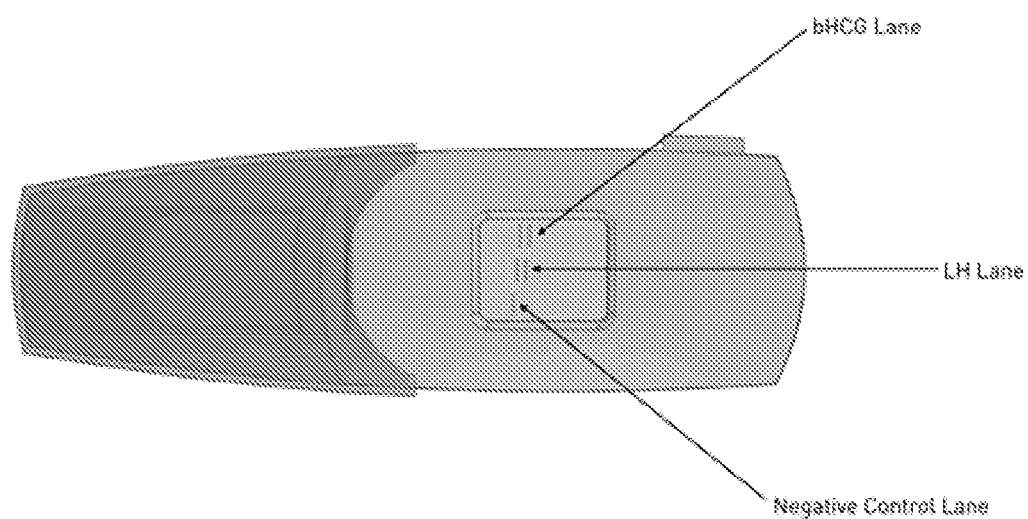
FIG. 8 is a schematic of a test strip that combines both ovulation and pregnancy testing.

A test was developed that is extremely sensitive and enables detection of β-hCG in urine 8 days prior to a woman's expected missed period. When reaching these sensitivities, cross reactivity with LH becomes an issue such that high LH levels can give a signal comparable to very low β-hCG levels. To overcome this, a test strip which tests for both LH and β-hCG at the same time from the same urine sample was developed. With both test results in hand, one can ignore the β-hCG signal when there is high LH thus eliminating false positives resulting from LH cross reactivity. An exemplary test strip is shown in FIG. 8.

The newly developed test has the added benefit of reducing end-user complexity. Users currently may find the process of testing ovulation then pregnancy to be cumbersome and stressful. Part of this stress comes from remembering what test to take when. By combining LH and β-hCG tests in one stick, the confusion and hassle are eliminated. The test results and/or information about menstrual cycle can be used to determine which test to focus on. Additionally, the test results can be used to determine the woman's menstrual cycle without the need for user input.

Other combined testing kits on the market involve separate tests and the user should manually coordinate when to take each and how to interpret the results.

Personal Baselining

The majority of diagnostics today are reported as numerical value. To put that value into context the number is often reported with a population average and a range of values around that average that are considered "normal". Being above or below that population distribution indicates something is different from normal (e.g. presence of a condition (pregnancy, inflammation); infection (strep, herpes); or a disease (diabetes, prostate cancer)). These population means and ranges come from relatively small trials on populations that are notorious for not being representative of the diversity of race and gender.

The system developed and described herewith provides several unique advantages that provides more personalized baselining and range determination. Specifically, the system provides clinical grade diagnostics sensitivity and quantification in a form factor that enables at home use. Additionally, there is a user facing application and a cloud system that log and chronical user data. These things together mean that an individual can test often enough personal baselines for each biomarker can be developed. Accordingly, the "normal range" for each person as an individual can be developed, and the individual can be alerted when there are deviations from their "normal range".

In some embodiments, the system would be smart and make decisions about what data to use. In some embodiments, published clinical guidelines could be used. In some embodiments, aggregated user data (which will eventually be more representative than the studies done by clinicians simply due to the reach) could be used, or data from that individual (personal baseline) could be used.

In some embodiments, when a user is new to the platform, clinical or aggregate distributions are used. However, once the system has enough information to confidently build a personal baseline, it will transition to using the personal baseline to provide better results.

Example 5. Improvement of Gel Electrophoresis

Gel Size Improvement

Figure 9:
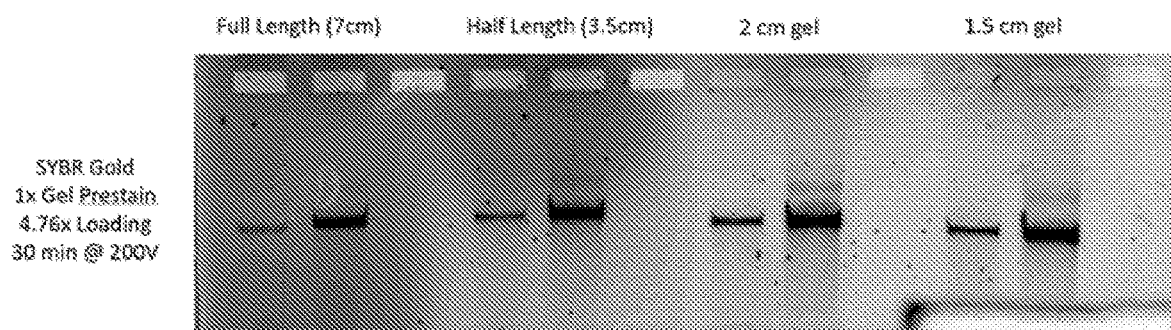
FIG. 9, panels A and B, show improvement of gel size in order to reduce background using SYBR Gold and GELRed pre-stained gels.
Figure 9:
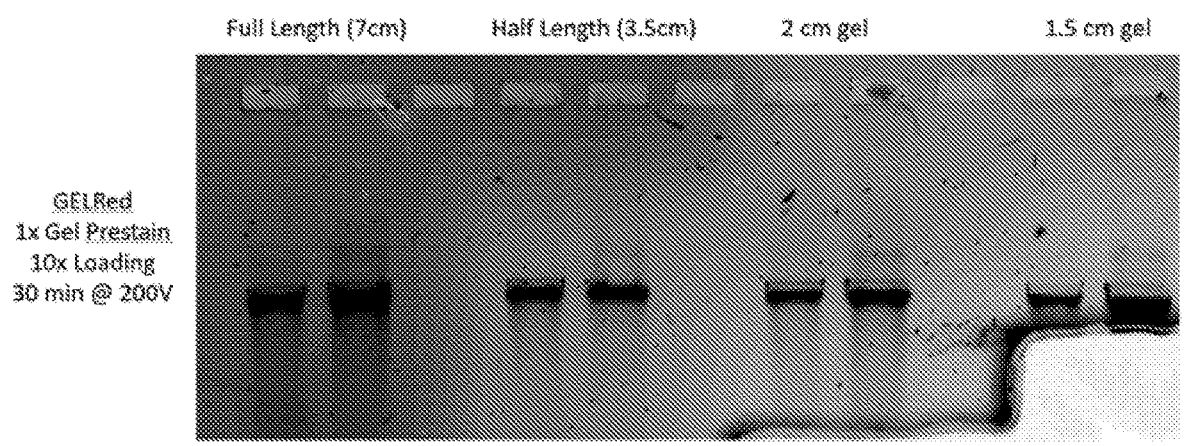

Slice Technology provides the benefit of reducing background within a pre-stained gel as well as the benefit of slightly increasing running distance within the gel by reducing the resistance along the electron pathway. FIG. 9, panels A and B, show the reduction in background with slight increase in running distance/separation within both the SYBR pre-stained gel and the GELRed pre-stained gel as the size of the gel decreases.

In some embodiments, 2 cm gels were used as slightly different running conditions could cause linear DNA to approach the cut and possibly run off the gel (e.g., as seen in the GELRed 1.5 cm show in FIG. 9, panel B). To achieve this, a full-length gel was poured with two sets of wells, one at the top and the other half-way, and that gel was measured and cut to create two 2 cm gels.

For different running conditions, the length of the gels could be adjusted and changed to reduce the total distance between the end of the gel and the linear DNA band.

FLIP Technology

When running gels that have been pre-stained with fluorescent DNA binding dyes, the residual dye left in the gel can sometimes make gel analysis problematic. One solution to this problem is to cut the gel so that the dye runs out of the gel during the running process (see above). This method works because the dye is positively charged and moves more quickly through the gel towards the negative electrode than does the DNA towards the positive electrode.

Figure 10:
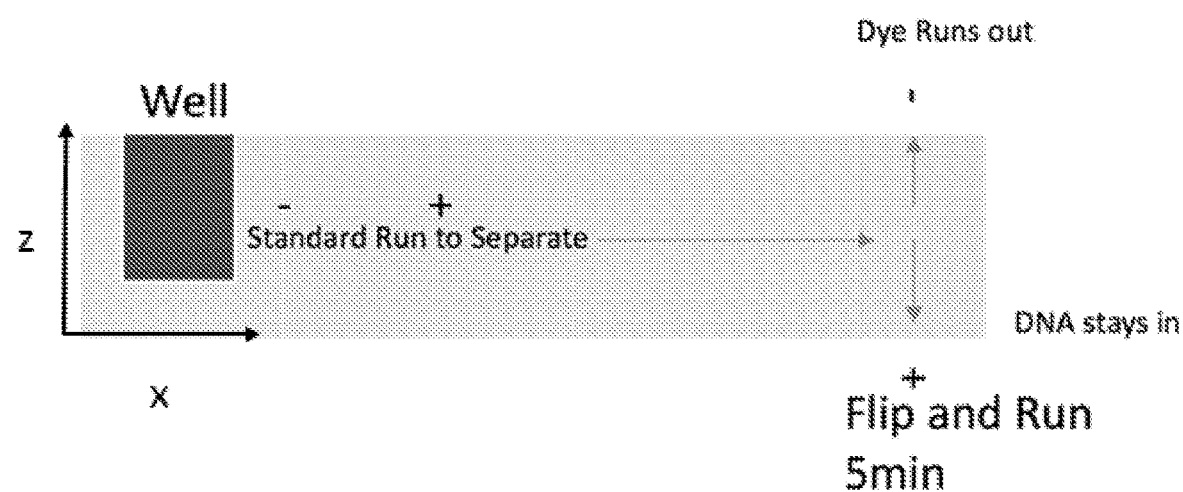
FIG. 10 provides an illustration of flipping the voltage in a direction orthogonal to the original (x) run direction to reduce background.

An alternative is to run the dye out of the gel in a direction orthogonal to the run direction as depicted in FIG. 10. First, the voltage was applied in the standard orientation so that the DNA migrated into the gel. Subsequently, either the voltage or the gel was 'flipped' such that the stain migrates out of the gel vertically (in the z direction as shown in FIG. 10), while the DNA migrated towards the bottom. This procedure was done by either rotating the gel, or by using a separate set of electrodes to apply a voltage in the z direction. This flip technique also alleviated a problem that could arise with the slice method described above, i.e., cutting the gel sometimes resulted in the DNA running too close to the end of the gel, which can hinder analysis.

Hydroxyethyl Cellulose Gels

While plain agarose gels are widely used for native gel electrophoresis, additives can be added to change the running conditions. Generally, these consist of another polymer that can change the gel's properties once it has formed. One polymer of interest is hydroxyethyl cellulose (HEC), a thickening and gelling agent generally used as an additive in cosmetics, drug capsules, and cleaning products. Adding HEC to agarose gels improves the separation between the linear and looped NS bands compared to agarose alone. This allows gels to be run for less time but maintain good separation for later analysis.

Specifically, the following experiment was performed: 0.5 g of agarose and 0.2 g of HEC (2-Hydroxyethyl cellulose, average Mv~90,000) were added to an Erlenmeyer flask. 50 mL of 0.5×TBE buffer was then added. The mixture was heated and mixed well until boiling while making sure all materials were dissolved and well mixed. The mixture was then gently cooled in a water bath, and stain was added if desired (e.g., SYBR Gold or GelRed). The mixture was poured into gel mold, and any bubbles were removed. The gel was cooled completely before use. HEC gels cold be run for less time than similar agarose gels.

Figure 11:
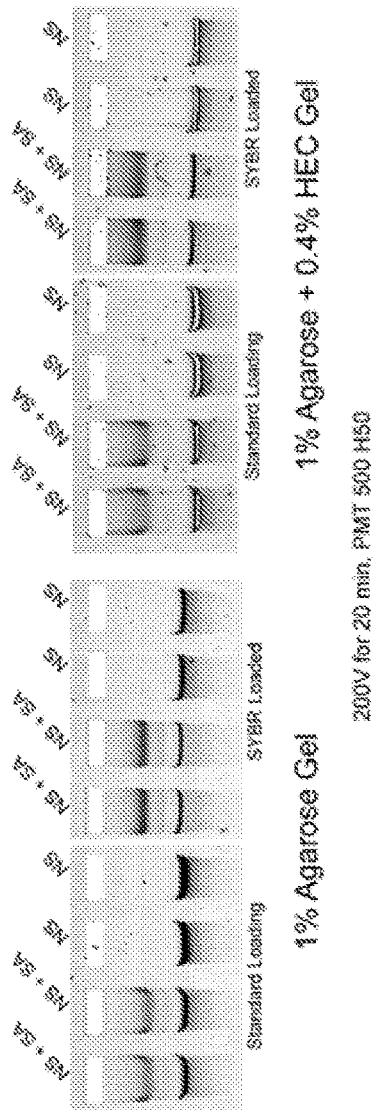
FIG. 11, panel A, shows a comparison of 1% agarose gel versus 1% agarose gel with incorporation of 0.4% hydroxyethyl cellulose (HEC). Panel B provide a series of plots showing the effects of various percentage of agarose and HEC on running conditions.
Figure 11:
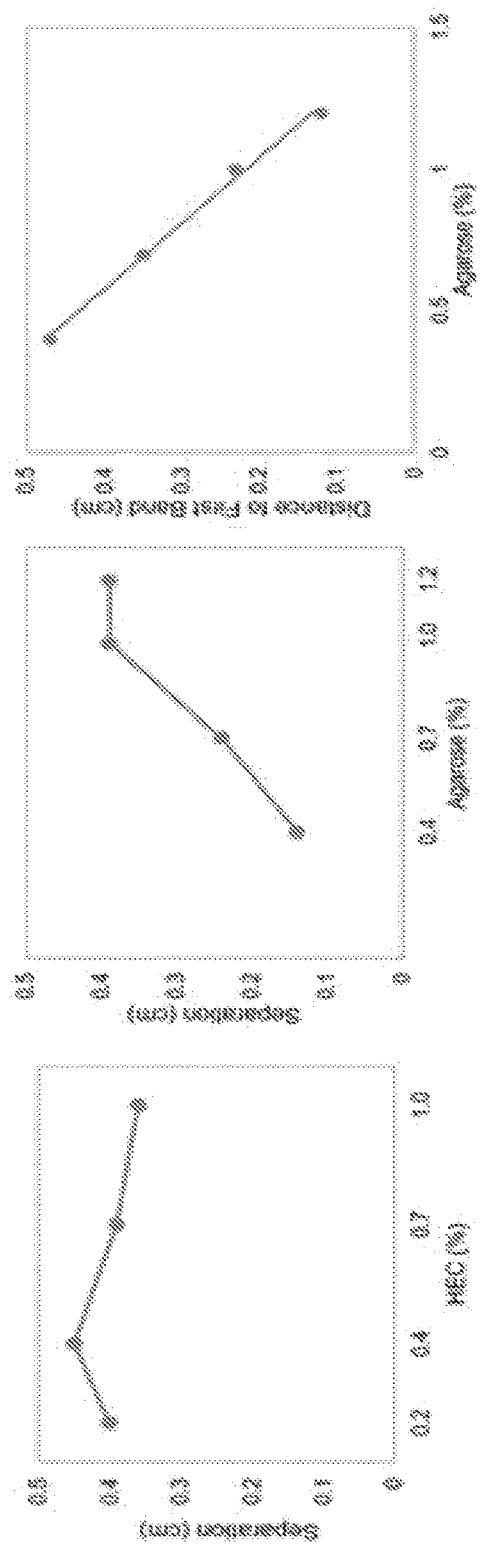

FIG. 11, panel A, shows a 1% agarose gel compared to a 1% agarose gel with 0.4% HEC added. With the incorporation of HEC, the average separation improved from 0.3 cm to 0.39 cm, i.e., a 26% increase in separation despite the same material and running conditions. FIG. 11, panel B shows plots of the effect of various percentages of HEC and Agarose and their effect on the running conditions. In the first plot agarose was held constant at 1.0% and HEC was changed, which showed the most improvement at 0.4% HEC. When HEC was held constant at 0.7%, and agarose changed, the best results were at 1.0% agarose and above. The last plot shows that the travel distance of the first band was inversely correlated to the agarose band, so 1.0% agarose was selected as for its good separation while maintaining some distance from the well.

Buffer Level Control

Buffer Level Control (BLC) provides the benefit of standardizing run distance between many different gels by controlling the total current pass-through within the gel. For gel electrophoresis, a voltage drop is generated across buffer and an agarose gel with the current in the gel moving linear DNA and other constituents through the gel. The resistance for where buffer and the gel exist in parallel is modeled by the equations below.

$$R_{gel} = \frac{L}{h_{gel}W} * \rho_{gel} \quad R_b = \frac{L}{h_bW} * \rho_b \quad \frac{1}{R_1} = \frac{1}{R_{gel}} + \frac{1}{R_b} = \frac{W}{L}\left(\frac{h_{gel}}{\rho_{gel}} + \frac{h_b}{\rho_b}\right)$$

Where L is the length of the gel, W is the width of the gel, $h_{gel}$, and $h_b$ are the heights of the gel and the buffer level above the gel, respectively, and $\rho_{gel}$ and $\rho_b$ are the respective electrolytic resistivities of gel and buffer where $\rho_b$ is smaller than $\rho_{gel}$. There is also buffer after the gel, which causes the overall resistance to be:

$$R_2 = \frac{L_2}{(h_b + h_{gel})W} * \rho_b \quad R = R_1 + R_2 = \frac{1}{\frac{W}{L}\left(\frac{h_{gel}}{\rho_{gel}} + \frac{h_b}{\rho_b}\right)} + \frac{L_2}{(h_b + h_{gel})W} * \rho_b$$

Ohm's Law states that current is related to resistance and voltage by the equation:

$$I = \frac{V}{R}$$

and voltage is held constant by the power supplies used for electrophoresis. This leaves the only variable within BLC to be the buffer height which causes the overall resistance to approach zero as it increases infinitely thus increasing the overall current. But, since the buffer and gel are in parallel, a greater percentage of current will be through the buffer opposed to gel as shown by:

$$\frac{R_b}{R_{gel}} = \frac{I_{gel}}{I_b}$$

Figure 12:
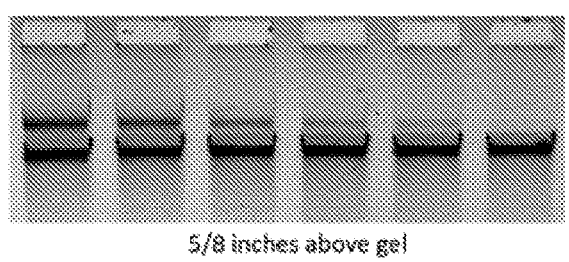
FIG. 12 shows the effect of buffer level (⅝ inches above gel or ⅜ inches above gel) on DNA running distance.
Figure 12:
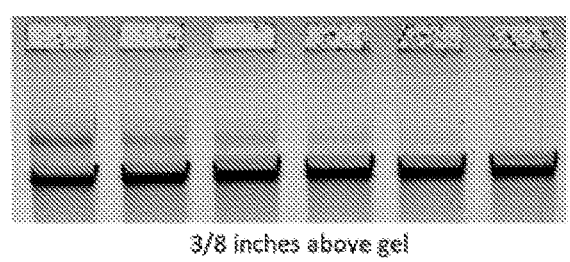

As shown in FIG. 12, two halves of the same gel, in the same buffer, for the same run-time, and same batch when tested with different buffer levels, can result in different DNA running distances.

In various embodiments, buffer levels are improved for gel electrophoresis.

Constant Current Gels

Typically, native agarose gels are run using a constant voltage. This allows the current to fluctuate in order to maintain the voltage, since the resistance of the gel can change, mostly due to changes in temperature resulting from joule heating during the running process.

A constant voltage does reduce the amount of heat generated as it runs, and the current does reduce over time. This makes for a safer running environment for long gel runs. However, since the nanoswitch tests being developed involve quick gel runs, heat generation is more manageable. Since current is the measure of ion/charged molecule movement, holding current constant leads to DNA traveling in a tighter band. Overall, there is some sacrifice in travel distance, but there are large gains in the sharpness of the looped bands.

Figure 13:
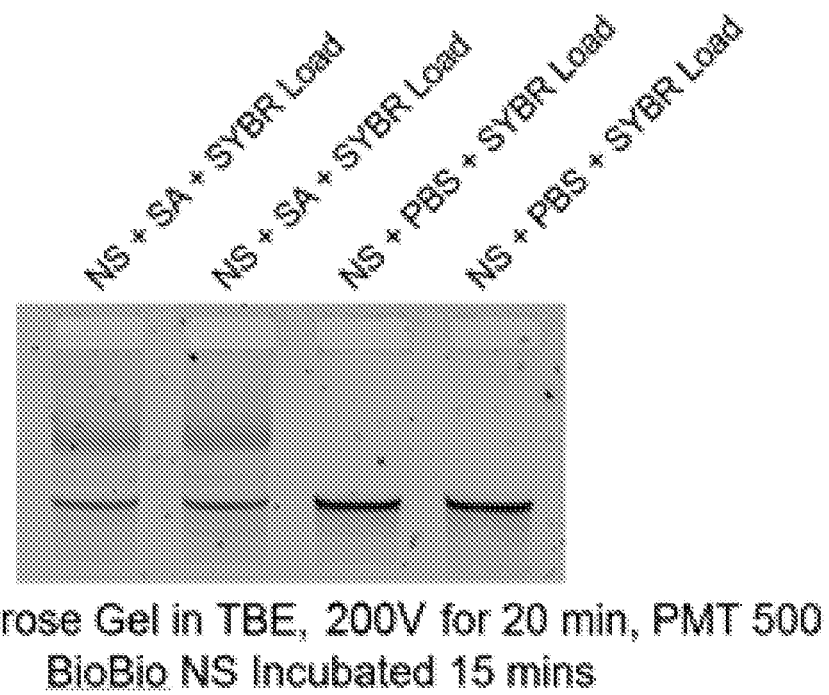
FIG. 13 shows a comparison of gels ran at constant current voltage (top gel) versus constant current (bottom gel). Improvement in sharpness of the looped bands was seen with gels ran at constant current.
Figure 13:
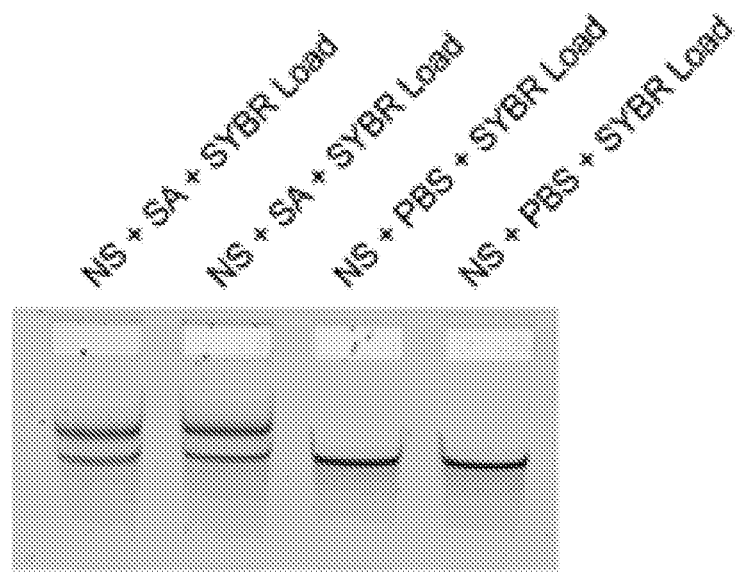

To hold the current constant, when running gel, the voltage was set to maximum and the power supply was set to constant current at 40 mA, which was roughly equivalent to 200V. A comparison of constant voltage versus constant current is shown in FIG. 13. By holding the current constant, gels may be run for less time and still maintain resolvability of the two bands due to the improved sharpness.

Tiny Gels (High V/Cm)

Being able to separate looped DNA from unlooped DNA is key to the detection technology described herein. The ability to do so quickly becomes extremely important for two reasons. First, the technical limitation of needing to ensure that the gel run time is shorter than the lifetime of the looped nanoswitches (as they can fall-apart/unloop during gel running resulting in a smear rather than a band). Second, ensuring a test run time is tolerable to the end user.

For these reasons methods for reducing the gel run time was developed. One such method is increasing the electric field measured in Volts/centimeter (V/cm). This can be achieved by either increasing the voltage applied across the gel or decreasing the size of the gel and thus the separation between the electrodes.

Figure 14:
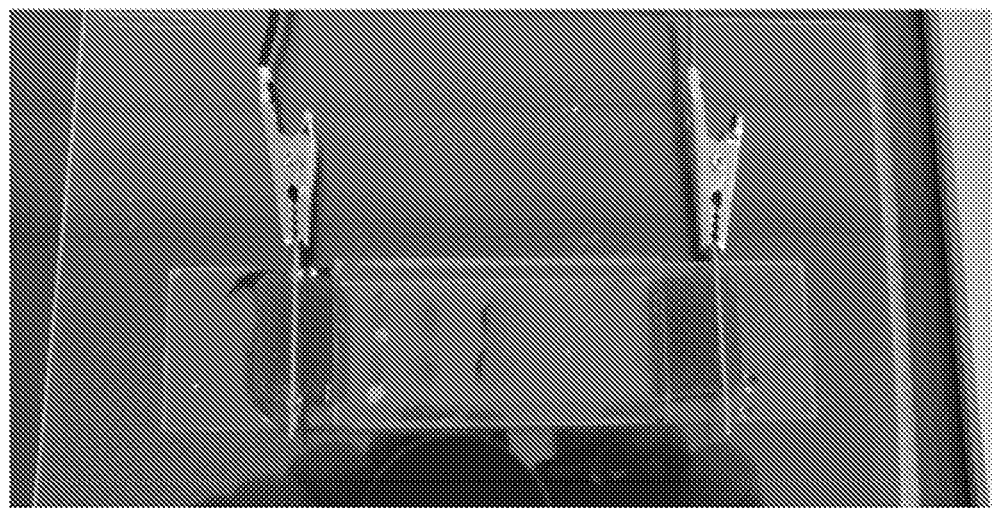
FIG. 14 depicts exemplary tiny gels (approximately 1-5 cm) that were used as described in Example 5. The exemplary gels shown in FIG. 14 are 2.5 cm.
Figure 14:
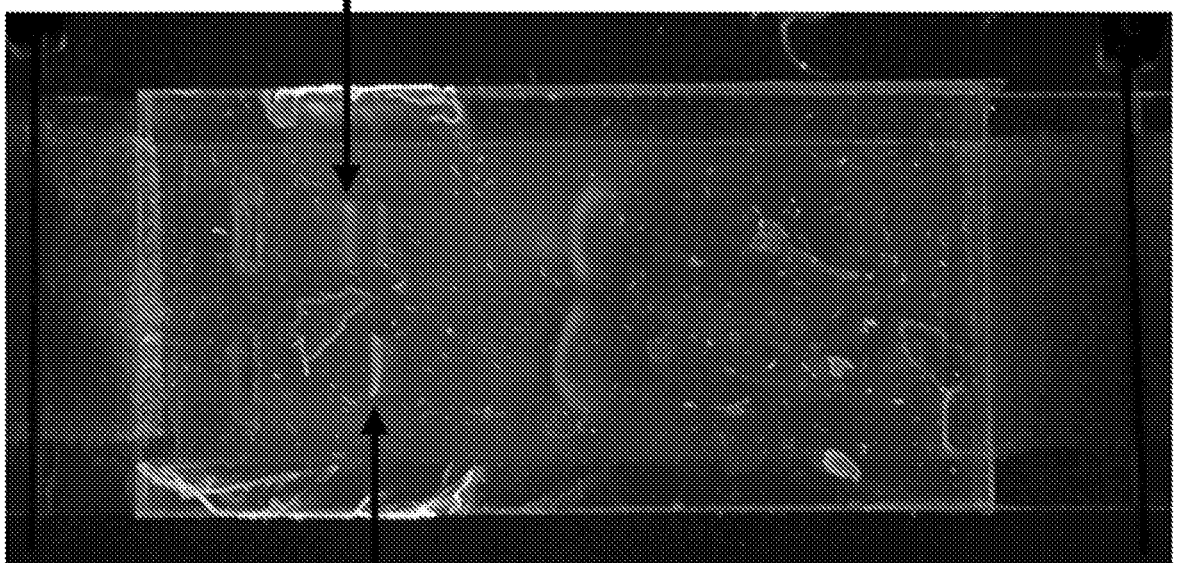

In an embodiment, a system was developed which utilized that provided 4 V/cm and took 1 hr and 40 minutes to provide separation. Alternatively, smaller gel boxes (14 cm vs 30 cm) and larger voltages (300V vs 100V) were used to reduce the gel runtime needed to see separation to 20 minutes. Additionally, very small gels (approximately 2-3 cm long) were developed enabling gel running in under 5 minutes. At such small scales, bubbles begin to interfere with the consistency of current through the gel. Using sponges soaked with electrolyte eliminated this issue. Exemplary small gels are shown in FIG. 14, which provided a clear differentiation between looped and unlooped DNA.

Gel Pre-Staining

DNA stains bind to DNA. This tends to alter the migration of DNA through gels during electrophoresis. For this reason, agarose gels are often stained after running to reduce potential issues with the dyes causing issues in the running conditions.

Figure 15:
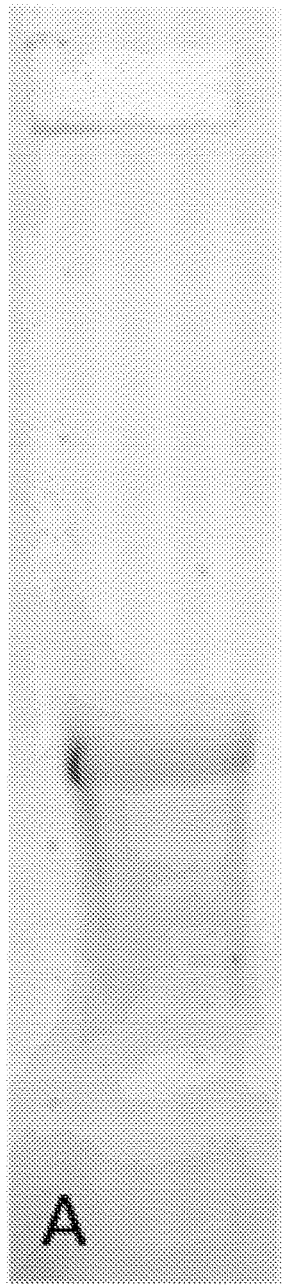
FIG. 15, panels A and B, depict gels that were not pre-stained (panel A) or pre-stained with 1×SYBR Gold (panel B).
Figure 15:
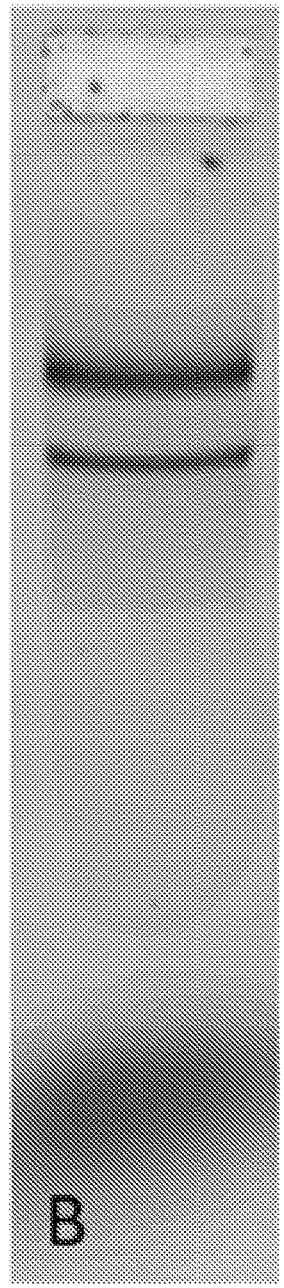

It was surprisingly discovered that although pre-staining did alter DNA mobility (overall reducing mobility), it actually increased the separation of looped and linear DNA (see FIG. 15). Without wishing to be bound by theory, it is believed that pre-staining slowed the looped DNA more than it slowed the linear DNA thus enabling shorter run times. This also had the added benefit that pre-stained gels allowed for the gel to be analyzed immediately after running.

Thus pre-staining the gels resulted in advantage including reducing the gel running time required to resolve the looped DNA signal from the linear signal, reduced the number of steps required to run the assay by eliminating the staining step, and reduced the time to run the assay by eliminating the staining step.

To stain gels with either SYBR Gold or GELRed, gels were made by boiling 350 mg of agarose in 50 mL of 0.5×TBE followed by cooling to approximately 40° C. before adding 5 μL of 10,000×SYBR Gold or GELRed. The solution was mixed and poured into a gel box in the fridge.

Buffer Consistency

It was discovered that gel running conditions were extremely sensitive to the gel running buffer composition. This was especially important when running gels in high electric fields (Volts/cm). Once a voltage and run time condition had been chosen for a particular running buffer, changes in the buffer composition could alter the migration of the DNA nanoswitch, and the heating of the running buffer. Altered migration of the DNA could cause changes in the band quality and band separation rendering a gel unanalyzable. Heating could cause the looped DNA nanoswitches to fall apart during the running of the gel, resulting in both a loss of band quality and reduced signal.

As such, tight regulation of the running buffer composition ensured reliable running results. All running buffers were therefore made using precision graduated cylinders and volumetric flasks such as the protocol described below for making 0.5×TBE running buffer:
Measure out 100 mL of 10×TBE in a 100 mL graduated cylinder;
Add the 100 mL 10×TBE to a 2 L volumetric flask;
Top the volumetric flask with milipore filtered water until the meniscus reaches the fill line.

Figure 16:
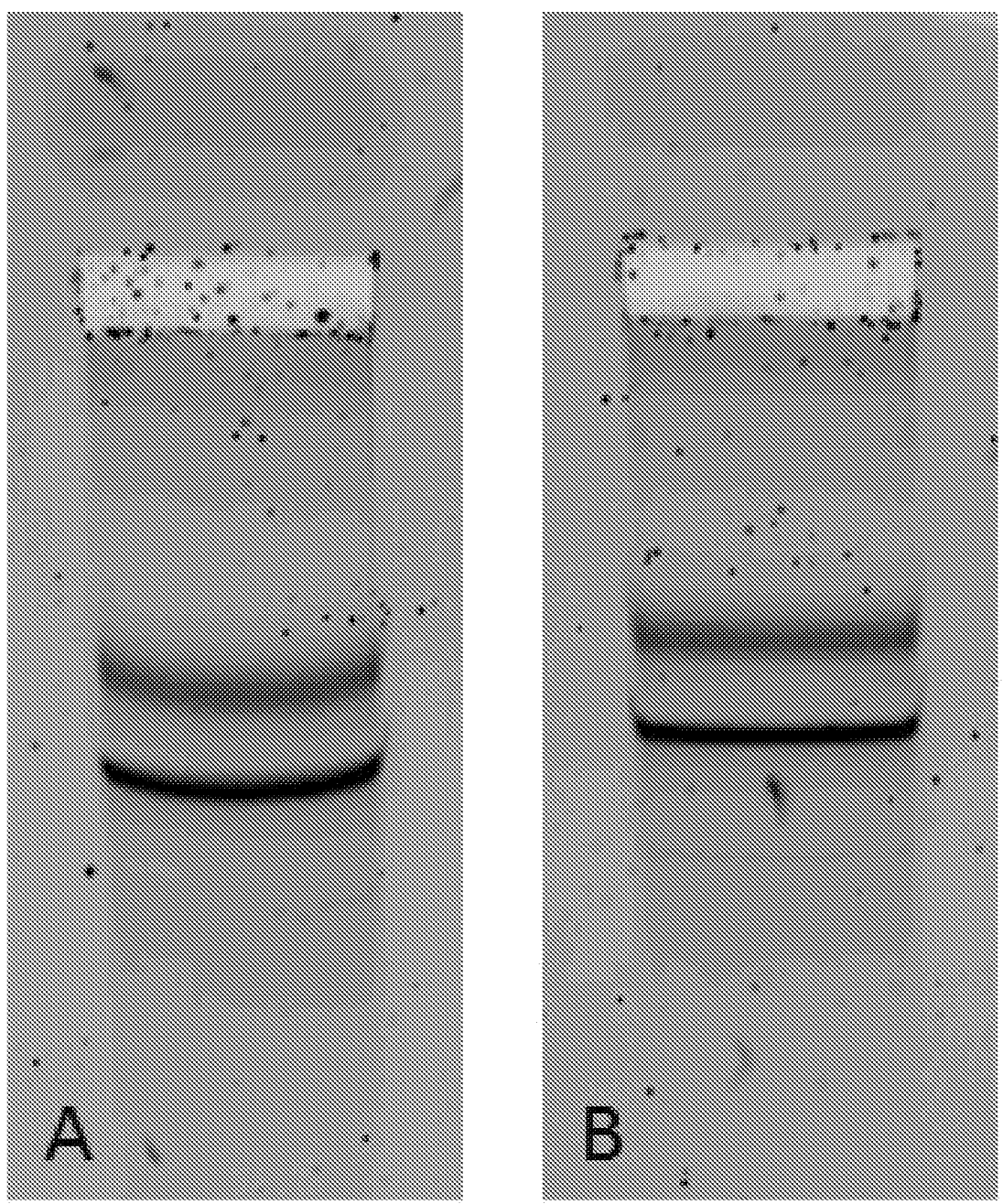
FIG. 16, panels A and B, provides a comparison of gels ran without pre-staining the sample (panel A) versus gel ran with a pre-stained sample (panel B). Pre-staining of sample appears to yield straighter and sharper bands.

Gel Preparation: Sybr Load and Red Load Protocols for Band Sharpness and Separation When running gels at high voltage to achieve short run times, band quality can be significantly degraded. It was discovered that adding the fluorescent DNA stain to the sample prior to loading in the gel can improve the clarity of the linear and looped DNA bands by both straightening and making the bands sharper (see FIG. 16, panels A and B). This yielded more reliable gel bands.

The procedure can be done with both SYBR Gold DNA stain and Gel Red. For SYBR Gold, this was done by adding 0.5 μL of 100×SYBR Gold and 2 μL of 6× Promega Loading Dye to 8.77 μL of material before being loaded onto a 1× pre-stained gel. For GELRed, this is done by adding 0.5 μL of 215×SYBR Gold and 2 μL of 6× Promega Loading Dye to 8.77 μL of material before being loaded onto a 1× pre-stained gel. Both of these loading conditions were altered to work best in urine but also worked well in buffer.

Example 6. Improvement of DNA Nanoswitch

Quad/Dodecas (Antibody Multiples)

When the concentration of the analyte is lower than that of the DNA nanoswitch (typical working concentrations of DNA nanoswitch range from 0.1 to 1 nM), it is the concentration of the nanoswitch not the concentration of the analyte that determines the fraction of analyte bound in equilibrium, and the rate at which the analyte binding reaches equilibrium.

To significantly improve the fraction of analyte bound, and minimize the time to reach equilibrium the concentration of the DNA nanoswitch can be increased. This, however, cannot be increased without end. If the concentration of DNA loaded in a lane is too high, there will be significant distortions in the lane profile, thus hindering analysis. A means of improving the nanoswitch performance was developed without increasing the total amount of DNA that needs to be loaded.

Figure 17:
FIG. 17, panel A, shows a typical DNA nanoswitch including a single pair of antibodies which can simultaneously bind to an analyte. Panel B shows an improved version of an antibody DNA nanoswitch that includes 3 pairs of antibodies with each type grouped in a closely spaced group. Panel C shows loop yield Increases as more antibodies are added to the scaffold. The gel on the left shows a nanoswitch with two antibodies has a 20% maximum loop yield. The middle gel shows a nanoswitch with 4 antibodies has a 30% maximum loop yield. The gel on the right shows a nanoswitch with 12 antibodies has a 90% maximum loop yield.
Figure 17:
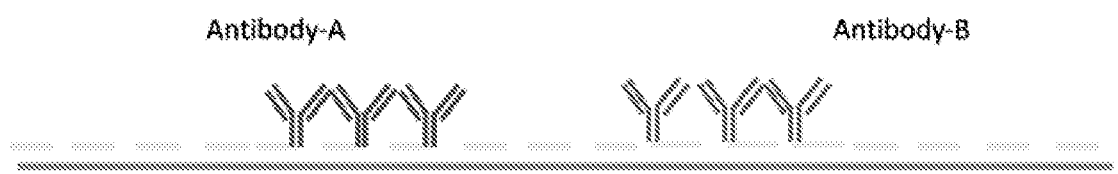
Figure 17:
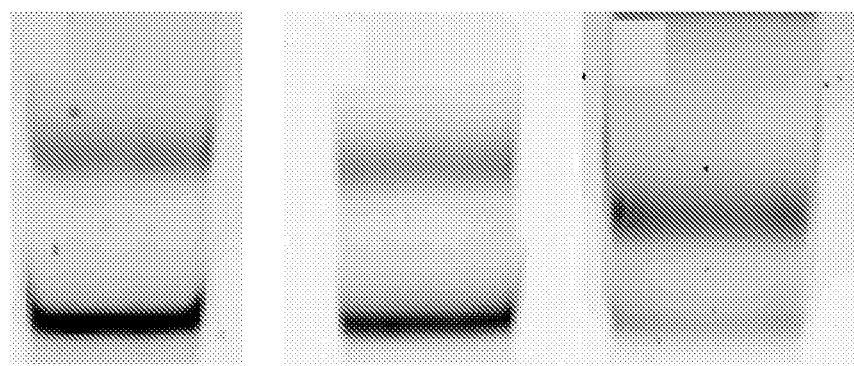

Typical DNA nanoswitches form a looped conformation via a pair of antibodies that are functionalized to oligos which are complementary to two different sites on the DNA nanoswitch scaffold (FIG. 17, panel A). By coupling multiple pairs of antibodies to oligos, DNA nanoswitches were created that composed of up to 6 pairs of antibodies (12 total antibodies). FIG. 17, panel B shows an example with three of each antibody (6 total antibodies). A design consideration when coupling such a high amount of antibodies is the location of the antibody. They should be located in clusters of close groupings so that all loop combinations run to a similar location in the gel.

Improvements in nanoswitch performance were observed as more antibodies were added to the DNA scaffold (FIG. 17, panel C). It was also observed that the kinetic performance of the nanoswitch was significantly improved, reducing 1 hour incubation time to 15 minutes when performing standard low analyte detection assays, when going from just 2 to 4 antibodies.

This concept could also be executed by coupling bi-valent or trivalent single-chain variable fragment antibodies, each of which can contain 4 or 6 analyte binding sites respectively. Another method is by chemically forming aggregates of multiple antibodies which can be coupled to a single oligo. This could be performed with a variety of multifunctional linkers.

Through experiments, the following M13 sites were identified as good locations to place clusters of antibodies

```
For a 4 antibody DNA nanoswitch
Cluster 1:
4.44_29:
                                        (SEQ ID NO: 4)
CTCAAATATCAAACCCTCAATCAATATCT 4.13:
                                        (SEQ ID NO: 5)
TTGGCAAATCAACAGTTGAAAGGAATTG Cluster 2:
4.19_1:
                                        (SEQ ID NO: 6)
ATAACTATATGTAAATGCTGATGC 4.19_3:
                                        (SEQ ID NO: 7)
AAATCCAATCGCAAGACAAAGAAC For DNA nanoswitch with 6 to 12 antibodies:
Cluster 1:
4.08 F20:
                                        (SEQ ID NO: 8)
CACCTTGCTGAACCTCAAAT 4.08 M20:
                                        (SEQ ID NO: 9)
ATCAAACCCTCAATCAATAT 4.08 L20:
                                        (SEQ ID NO: 10)
CTGGTCAGTTGGCAAATCAA 4.09 F20:
                                        (SEQ ID NO: 11)
CACCTTGCTGAACCTCAAAT 4.09 M20:
                                        (SEQ ID NO: 12)
CAGTTGAAAGGAATTGAGGA
```

-continued 4.09_L20:
AGGTTATCTAAAATATCTTT (SEQ ID NO: 13)

Cluster 2:
5.09_10:
GAGAAGAGTCAATAGTGAAT (SEQ ID NO: 14)

5.10_1:
TTATCAAAATCATAGGTCTG (SEQ ID NO: 15)

5.10_2:
AGAGACTACCTTTTTAACC (SEQ ID NO: 16)

5.10_3:
AGAGACTACCTTTTTAACC (SEQ ID NO: 17)

5.10_4:
TCCGGCTTAGGTTGGGTTAT (SEQ ID NO: 18)

4.19_1:
ATAACTATATGTAAATGCTGATGC (SEQ ID NO: 6)

4.19_3:
AAATCCAATCGCAAGACAAAGAAC (SEQ ID NO: 7)

False Positive Signals

When using DNA nanoswitches that are functionalized with antibodies, a common problem that can occur is the formation DNA loop in the absence of the antigen. This is commonly referred to as a false positive signal (see, for example, FIG. 18, panels A and B).

Analyte can still be detected when there is false positive signal by looking at differential measurements between a negative control lane, and the analyte containing lane. However, creating a true negative lane can be difficult when working to detect analyte in urine specimens as subjects often have baseline levels of analyte and the bodily fluid can add other signal.

Figure 18:
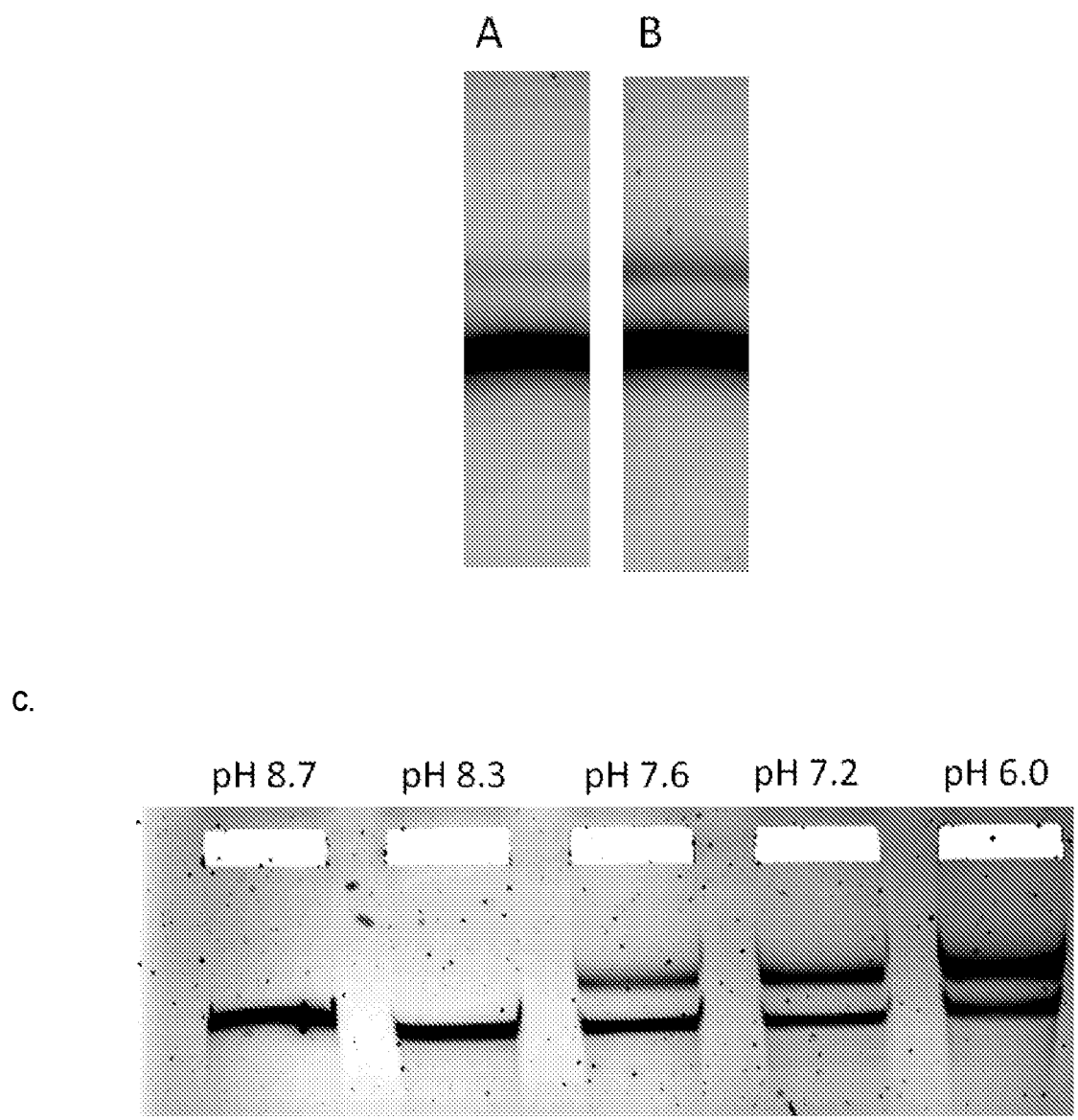
FIG. 18, panels A and B, show an example of a false positive signal. Panel A shows a gel lane with no analyte present containing a looped DNA band. Panel B shows a gel lane with low amount of analyte (10 pM) containing a more intense looped DNA band. Panel C shows the effect of pH on false positive signal. All of the lanes lacked analyte, but have been incubated in buffers with differing pH. For this nanoswitch, high pH eliminated the false positive signal.

Several solutions were developed to eliminate/reduce false positive signals. One method for reducing false positive signals was the control of solution pH. A person's urine can fluctuate in pH values from pH 5-8. It was discovered that buffer pH affected the false positive signal of a DNA nanoswitch (see FIG. 18, panel C). As seen in FIG. 18, panel C, the pH of the buffer had a significant effect on the false positive signal. It was observed that this was dependent on the antibody being used. Therefore, this should be studied for each pair of antibodies. Once the optimal pH was found, the appropriate buffers could be selected to regulate pH to the desired range in the bodily fluid of interest.

It was also discovered that buffering with TBE and EDTA helped mitigate false positives in urine for bHCG nanoswitches. Additionally, it was discovered that the use of passivating agents such as, tween, BSA, and poly ethylene glycol, or casein could also help to reduce false positive signals.

Nanoswitch Concentration to Enable Low Concentration Antigen Detection

When the concentration of the antigen being detected, $A_{tot}$, is considerably lower than the concentration of DNA nanoswitch, the fraction of antigen which is bound to the nanoswitch, and in the looped conformation $$\frac{A}{A_{tot}},$$

is determined by the concentration of the DNA nanoswitch $C_{dna}$, the effective concentration of the two antibodies to one another (as these antibodies are tethered by the Nanoswitch, the effective concentration is proportional to the loop size or length of DNA between them), $C_L$, and dissociation constant of the receptor-antigen interaction $K_d$. The fraction $$\frac{A}{A_{tot}}$$

as a function of $C_{dna}$, $C_L$, and $K_d$ are described by the following equation:

$$\frac{A}{A_{tot}} = \frac{1}{\frac{K_d^2}{C_{dna}C_L} + 1 + \frac{2K_d}{C_L}}$$

This model illustrates the three important factors to consider when detecting low concentration of analyte, $C_{dna}$, $C_L$, and $K_d$.

If one increases $C_{dna}$ or $C_L$ and/or decrease $K_d$ then improvements in sensitivity can be achieved. Furthermore, increases in $C_{dna}$ will also lead to a decrease in the binding time for the analyte. Increasing $C_{dna}$ can be achieved by simply increasing the concentration of Nanoswitch in solution. It was observed that sensitivity could be increased and incubation time could be decreased by increasing $C_{dna}$.

Increasing $C_L$ can be achieved by decreasing loop size, or increasing the number of antibodies on the construct. Decreasing $K_d$ could be achieved by using different antibodies.

In various embodiments, the concentration of the nanoswitch is changed/improved.

Megaloop Design (Loop With a Latch)

A megaloop design for the DNA nanoswitch was developed. Without wishing to be bound by theory, it is believed that the megaloop design can achieve two purposes: (i) a larger loop size for better separation and (ii) includes a latch to increase local concentration of antibodies on the construct which significantly improves the amount of analyte bound in the looped geometry. The latch can be made using streptavidin-desthiobiotin, streptavidin-biotin, DNA overhangs, or any other binding partner (preferably one with revisable binding). As an exemplary embodiment, a streptavidin-desthiobiotin (dbio), streptavidin-biotin (bio) latch is described.

The high local concentration also decreases the amount of DNA nanoswitch which has two analytes bound. This is especially important for solutions which have very high concentrations of analyte. If the concentration of analyte is too high, the majority of DNA nanoswitch will be capped and unable to loop. Megaloop ensures the closest possible distance between functionalized oligos and thus significantly improves the highest concentration of detectable analyte. This strategy leads to improved sensitivity of detection and incubation times required for the read out.

In an exemplary design shown in FIG. 19, panels A-D, the bio/dbio latch forms a smaller (inner) loop bringing the antibodies in close proximity (FIG. 19, panel B) than they were originally in the linear conformation of the construct (FIG. 19, panel A). Next, addition of the target of interest triggers the formation of the outer loop by the binding of the two antibodies to the antigen (FIG. 19, panel C). The latch can be released by addition of excess biotin, and the looped detection band of the antigen can be readout (FIG. 19, panel D).

Particularly, the latch is closed by binding of streptavidin (SA) to the biotin and desthiobiotin on the construct thereby forming a loop. Construction and testing of the latch using different concentrations of streptavidin is shown in FIG. 19, panel E.

The off-rate for biotin-SA-desthiobiotin latch was characterized. After detecting the antigen of interest, the latch can be released while the outer loop with the antigen-antibody interaction remained bound. For the latch to be released, excess biotin (as saturated biotin) was added to the solution which released the streptavidin bound to biotin/desthiobiotin on the construct and saturated all the available binding sites on the streptavidin molecule (one streptavidin can bind to four biotin moieties). FIG. 19, panel F shows how long it takes for the latch to be released. Specifically, release was tested at different time points on addition of biotin (lanes 1-6). It was determined that the latch was released between 30-60 minutes.

A megaloop using "key" and "bridge" oligonucleotides was designed as shown in FIG. 19, panel G. In this design, loop formation was tested using DNA strands instead of antibodies. Two versions of the construct were used for testing.

In the first version (top panel of FIG. 19, panel G), the megaloop construct had single-stranded extensions (seq-a and seq-b) at locations where the antibody-oligo conjugate was placed. Loop formation was tested by the addition of a DNA strand whose sequence was partially complementary to the single-stranded extensions (region seq-a* is complementary to extension seq-a and seq-b* is complementary to seq-b). Hybridization of this "key" oligonucleotide led to loop formation.

In the second version (bottom panel of FIG. 19, panel G), the megaloop construct had single-stranded regions on the scaffold M13 at locations where the antibody-oligo conjugate was placed. This was done by omitting specific backbone oligonucleotides that bind to those regions on the M13. Loop formation was tested by the addition of a DNA strand whose sequence was partially complementary to the single-stranded regions on the scaffold M13. For example, region 4.44* and L9* are complementary to single-stranded regions 4.44 and L9 on the M13 scaffold. Hybridization of this "bridge" oligonucleotide led to loop formation.

The megaloop using "key" and "bridge" oligonucleotides was characterized as shown in FIG. 19, panel H. Specifically, the stability of the megaloop using "key" and "bridge" oligonucleotides to close the loop, with and without bio/dbio/SA latch, was tested. Design and working principle is shown in FIG. 19, panel H, top and middle gels, which show loop formation using 'key' oligonucleotides of different lengths (30-nucleotides and 20-nucleotides respectively). Both these key oligonucleotides were designed to bind to the same single-stranded extension on the construct (30-nucleotides long). FIG. 19, panel H, bottom gel shows loop formation by the hybridization of a 40-nucleotide 'bridge' oligonucleotide to 20-nucleotide single-stranded regions on the M13 scaffold. It can be seen that the megaloop (~3900 bp, indicated by white arrow) migrated slower than a smaller loop (~900 bp, indicated by black arrow).

The megaloop with antigen-antibody interaction was also characterized (FIG. 19, panel I). For detection of βHCG, antibody-oligonucleotide conjugates were annealed on to the construct (antibody 5011 on 4.44 and antibody 5008 on Var L9). Different amounts of the antibody-oligo conjugate were added to the annealed M13/backbone oligo mixture (1:1, 1:3 and 1:5) with the highest amounts yielding a construct that did not have false positive bands. Detection of βHCG using this construct was also indicated by loop formation.

Alternative ssDNA Linearization and Source DNA

Nanoswitch loop size has been observed to have an effect on the migration distance of looped constructs. Increasing loop size, while fixing gel run time, tends to increase the separation between the looped and linear bands (see, for example, FIG. 20, panel B).

In addition to changing the size of the loop, changing the way the originally circular ssDNA was linearized, as well as changing the DNA itself, was also tested.

Currently, circular M13 DNA is linearized using the BtsCI restriction enzyme. Restriction enzymes have differing targets and specificities for those targets. Linearizing the DNA at different locations means that the loop will (in most cases) stay the same size, but shift along the nanoswitch backbone. A variety of restriction enzymes was tested while holding constant the functional oligos (and thus the loop size) to determine which provided the cleanest, most reliable cut, and which significantly improves separation of the looped and linear bands (see FIG. 20, panels A and C).

Furthermore, different starting material for the DNA was also tested. Larger ssDNA scaffolds yielded greater signal/molecule as the number of dye molecules is directly proportional to the length of the DNA (see FIG. 20, panel B). A larger scaffold also allowed for larger loop sizes, increased separation, and more options for multiplexing interactions.

For linearization of M13 ssDNA using BtsCI, 10 μL of circular M13 ssDNA (NEB) were mixed with 5 μL of NEB buffer 2.1, 26 μL of nuclease-free water, and 1.0 μL of BtsCI complementary oligo. The mixture was brought up to 95° C. for 30 seconds and ramped down to 37° C. 8 μL of BtsCI enzyme (NEB) was added to the tube and allowed to incubate for 1 Hr at 37° C. and then heat inactivated at 90° C. for 1 minute.

For linearization of M13 ssDNA using EcoRI, 5 μL of circular M13 ssDNA (NEB) were mixed with 2.5 μL of NEB buffer 2.1, 13 μL of nuclease-free water, and 0.5 μL of EcoRI complementary oligo. The mixture was brought up to 95° C. for 30 seconds and ramped down to 50° C. 4 μL of EcoRI HF enzyme (NEB) were added to the tube and allowed to incubate for 1 Hr at 50° C. and then heat inactivated at 80° C. for 20 minutes.

M13 ssDNA was also linearized using BtsCI followed by EcoRI (BtsEco). Specifically, the BtsCI protocol was used followed by addition of 0.5 μL of EcoRI complementary oligo to 25 μL of BtsCI linearized M13 ssDNA. The mixture was brought up to 95° C. for 30 seconds and ramped down to 50° C. 4 μL of EcoRI HF enzyme (NEB) were added to the tube and allowed to incubate for 1 hour at 50° C. and then heat inactivated at 80° C. for 20 minutes. This yielded a shorter ssDNA scaffold cut at both the BtsCI and EcoRI restriction site.

For linearization of M13 ssDNA using HindIII, 5 µL of circular M13 ssDNA (NEB) were mixed with 2.5 µL of NEB buffer 2.1, 13 µL of nuclease-free water, and 0.5 µL of HindIII complementary oligo. The mixture was brought up to 95° C. for 30 seconds and ramped down to 50° C. 4 µL of HindIII HF enzyme (NEB) were then added to the tube and allowed to incubate for 1 Hr at 50° C. and then heat inactivated at 80° C. for 20 minutes.

Linearization of the p8064 circular ssDNA was also performed. 5 µL of circular p8064 ssDNA (Tilibit) were mixed with 2.5 µL of NEB buffer 2.1, 13 µL of nuclease-free water, and 0.5 µL of restriction-site complementary oligo (BtsCI, EcoRI, or HindIII). The ramping procedure was followed for each enzyme as described for M13 above to yield linearized p8064 ssDNA scaffold.

Figure 20A:
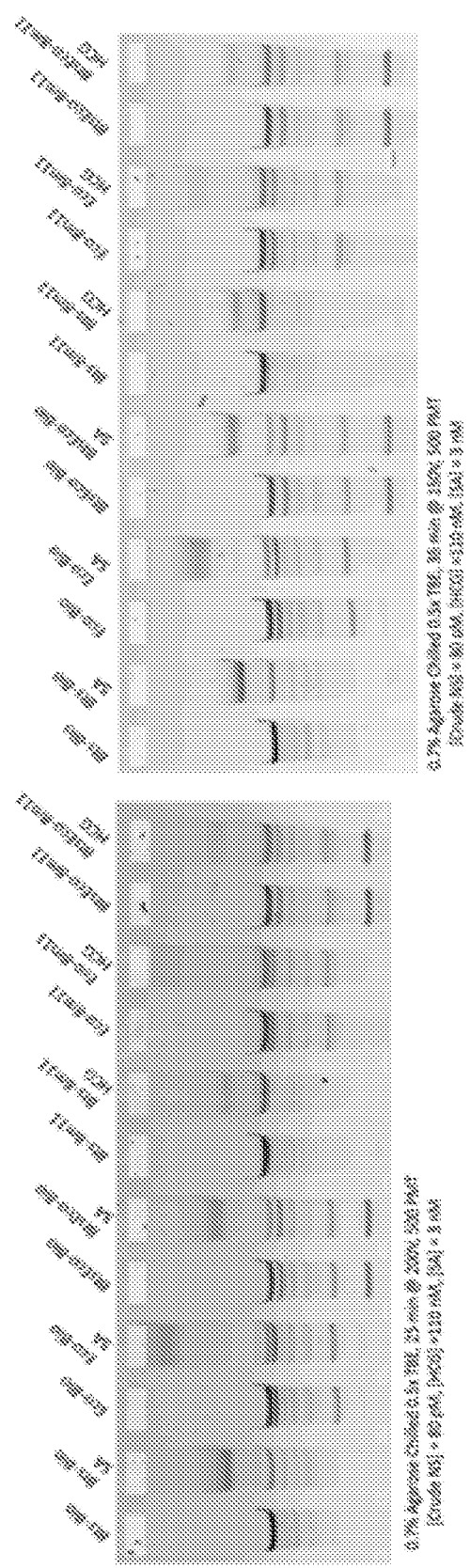
FIG. 20, panel A depicts loop migration comparison of alternative cut sites using various restriction enzymes. Panel B shows migration of oligonucleotide bridge loops at different restriction enzyme cut sites and DNA sources. Panel C shows loop migration of alternative restriction enzyme cut sites on M13 and p8064 DNA.
Figure 20:
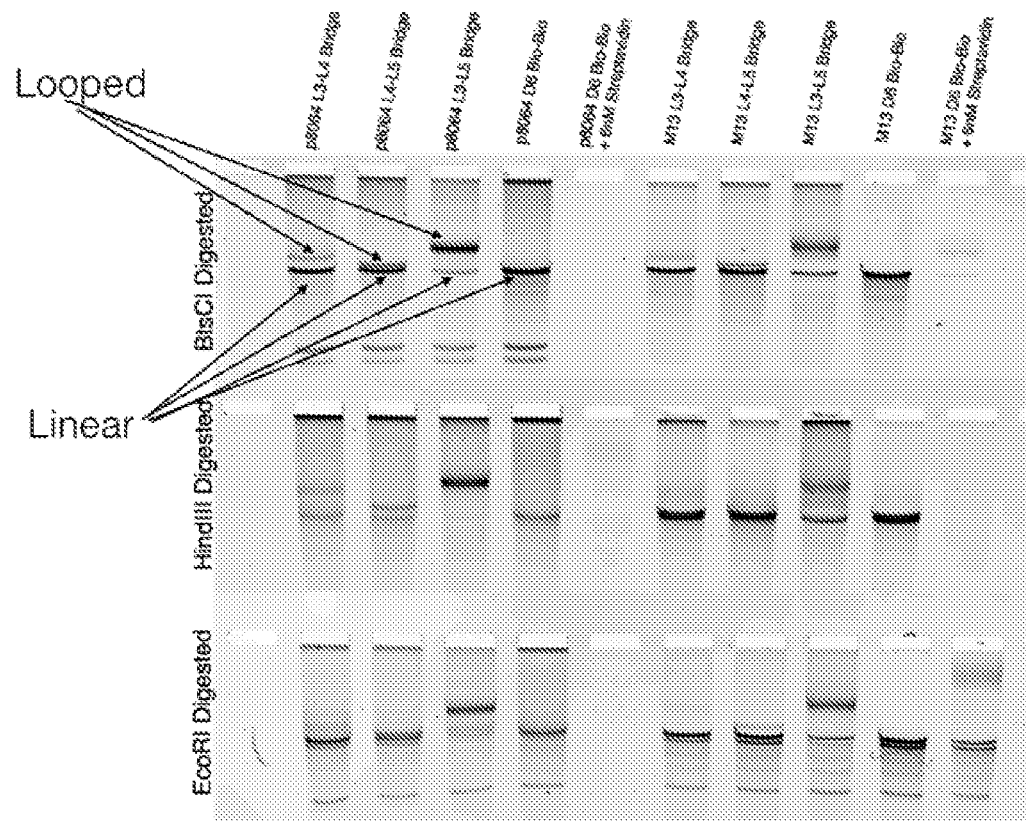
Figure 20:
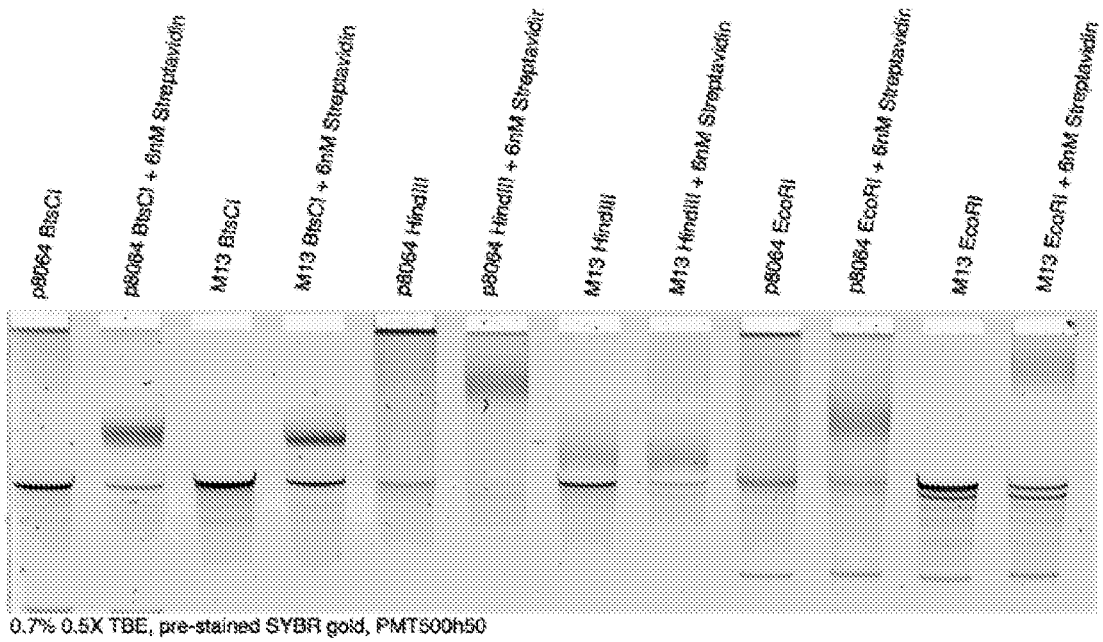

Formation of bridge loops was induced. Specifically, a fill 119 scaffold fill-in mix was prepared and hybridized to the linearized DNA scaffold. An additional p8064 fill-in mix was introduced to linearized p8064 ssDNA scaffolds to fill in the remaining DNA. Bridging oligos (a single oligo that bridges the two unhybridized regions of the scaffold to form a loop) were then introduced to induce specific loop sizes (L4-L5 (500 bp loop size) L3-L5 (1000-bp loop size), or L3-L4(600 bp loop size) conformations). Results are shown in FIG. 20, panels B and C.

Example 7. Process Improvements

Gel Purification

All phases of DNA nanoswitch construction require effective purification techniques. Particularly, it was observed that gel extraction is a highly effective tool for many purification processes. The Blue pippin device is an automated gel extraction system that simplifies the purification process. Gel extraction is particularly useful at two stages of DNA nanoswitch construction: the antibody conjugation step, and the DNA nanoswitch hybridization step.

Figure 21:
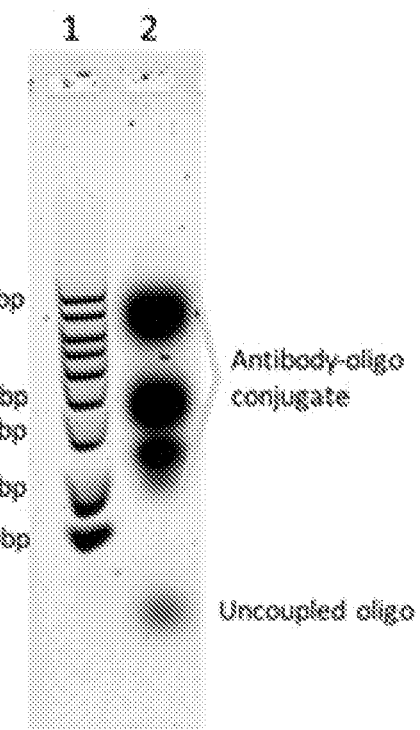
FIG. 21, panel A, shows antibody oligo conjugates ran on an agarose gel. Lane 1 is a DNA ladder, Lane 2 is mix of conjugated and unconjugated Antibody-oligo. The uncoupled oligo runs significantly lower on an agarose gel. Panel B shows selection of appropriate Blue Pippin cutoffs. Lane 1: DNA Ladder. Lane 2: An unpurified antibody oligo conjugate contains uncoupled oligo which runs below 1 kbp, and an antibody-oligo conjugate which runs similarly to where a DNA nanoswitch. Lane 3: A purified antibody which has been Blue Pippin purified using 1-3 kbp cutoff region. Lane 4: A DNA nanoswitch purified using a 5-9 kbp. If the antibody conjugates were not purified using the 1-3 kbp cutoffs there would still be excess antibody-oligo conjugate that could compete with the DNA nanoswitch for antigen binding.
Figure 21:
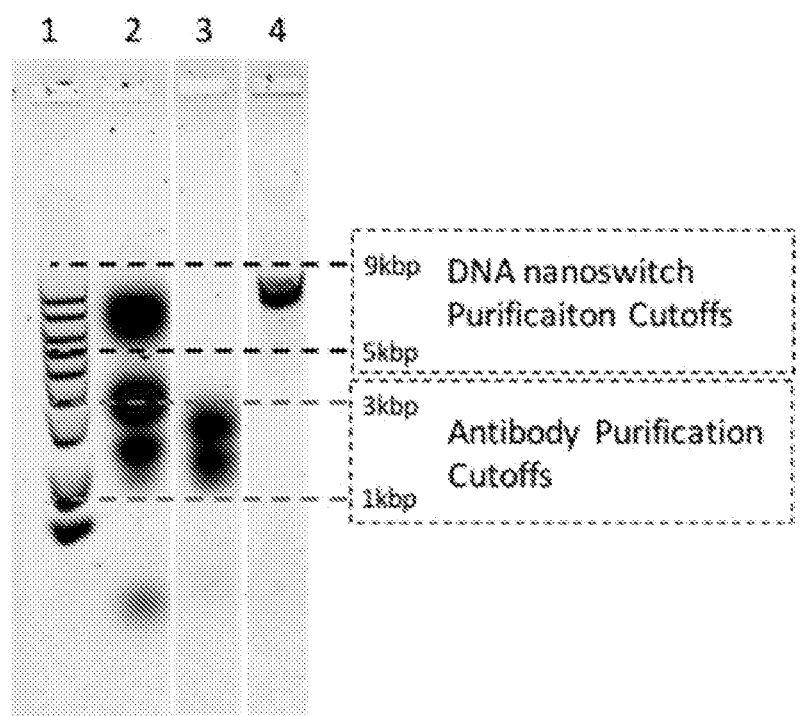

The purification of Antibody conjugates from unconjugated oligo is important in DNA nanoswitch construction. Uncoupled oligo can compete with the Antibody-oligo when hybridizing onto the DNA scaffold. This leads to a drop in nanoswitch functionality. As seen in FIG. 21, panel A, uncoupled oligo runs much faster on an agarose gel then Antibody-oligo conjugates.

In practice an agarose gel can be run, and the antibody oligo conjugates can be extracted from bands cut out of the gel. The use of a Sage BluePippin simplifies this process. It was observed that the 0.75% DF 3-10 kb Marker 51 Improved Recovery Cassette Definition was highly effective at removing uncoupled oligos. The Blue Pippin allows the user to select when to collect based on where the material runs relative to a DNA ladder. Based on FIG. 21, panel A, the user could enter cutoff selection of 1-9K to remove the uncoupled oligo and retain all the conjugated antibodies.

The antibody conjugate can then be hybridized to a DNA nanoswitch.

In order to significantly improve the hybridization efficiency of the antibody-oligo conjugate, it is typically added in vast excess to the DNA nanoswitch. This leaves unhybridized antibody in the solution which can compete with the DNA nanoswitch for analyte binding. Removal of these excess oligos is especially important when detecting analyte at low concentrations because high concentrations of DNA nanoswitch are needed. The BluePippin can be used to purify out any excess antibody which runs lower than the DNA nanoswitch (7249 bp). However, as seen in FIG. 21, panel A, there were sometimes antibody conjugates which run in the same location as the DNA nanoswitch. This required different cutoff selections to be used to remove Antibody conjugates which run near the DNA nanoswitch. It was determined that a reliable cutoff to choose is 1-3 Kbp, when purifying antibody-oligos conjugates (FIG. 21, panel B). These purified conjugates can then be hybridized the DNA nanoswitch, and sent through a second round of Blue Pippin Purification selecting a cutoff of 5 k-9 k.

Lastly, the BluePippin purification of the DNA nanoswitch also removed un-hybridized backbone oligos which fill in the single stranded DNA scaffold to make it fully double stranded. This has an additional benefit of leading to sharper DNA bands, and improved quality. When running DNA nanoswitch in a pre-stained gel the presence of excess oligo can alter the run conditions leading to poor band quality.

Nanoswitch Pulldown

When producing Nanoswitches it is important to be able to purify away excess oligonucleotides as excess functional oligonucleotides can bind to antigen thus blocking their ability to close a Nanoswitch.

One method for achieving this is to add a tag to the Nanoswitch that can be bound by a functionalized bead. The nanoswitch can be modified with a protein tag, small molecule tag, or a string of additional bases in the form of a single stranded region (e.g. an overhang at the 5' or 3' end of the Nanoswitch, or an unhybridized region anywhere along the nanoswitch). A nanoswitch with the protein or small molecule tag can be run through purification resin with the complementary binder to the tag on the resin. For example, a biotinylated oligo can be bound to the Nanoswitch. The Nanoswitch could then be purified with a resin made up of streptavidin beads. An end oligo can also be modified to have additional bases to include a polyA tail. The polyA tail would allow for purification using dT oligo beads. The nanoswitches can be eluted by the addition of binding partner excess biotin, excess streptavidin, excess polyA, or excess polyT. Other protein, small molecule, or nucleotide modifications can be used, as well.

Provided herewith is a protocol for the polyA purification with dT oligo beads for a Nanoswitch with two biotins on it. The protocol is also applicable to for the purification of Nanoswitches with two antibodies or two antigens, or any Nanoswitch.

Preparation of Magnetic dT Oligo Beads

Beads to sample ratio

Step 1-Prep N.S. With F30A and L30 Oligos to Add PolyA Strands

10 Var (−4.19, −Var12) was made with 10 µL of each Var excluding 4.19 and Var12. BB (−4.44) mix was made with 10 µL of each backbone excluding BB4.08 which overlaps with 4.44. Make a 119 Mix with:
  10 µL 10 Var (−4.19, −Var12)
  108 µL BB mix (−4.44)
  1 µL F30 stock
  2 µL [PolyA L30+ToeHold] mix stock
Mix a diluted 4.19 and 4.44 mix with 1 µL 4.19-bio, 1 µL 4.44-bio, and 13 µL NF water. Make NS solution:

| Solution | uL |
| --- | --- |
| M13 | 40 |
| 119Mix | 9.52 |
| 4.19/4.44 | 1.19 |
| 10X NEB Buffer 2 | 1.19 |

Heat in thermocycler with ANNEAL method (depends on the application)

Step 2: Solution Prep

The following solutions were made:
Binding Buffer 200 µL+(500*× washes) µL used:
20 mM Tris-HCl (pH 7.5)
500 mM LiCl
1 mM EDTA
Low Salt Buffer (decreased LiCl) 500 µL used:
20 mM Tris-HCl (pH 7.5)
200 mM LiCl
1 mM EDTA
10 µM polyA comp buffer
Stocks:
100 mM Tris-HCl (pH 7.5) (made already)
2.5M LiCl (3.18 g in 30 mL)
50 mM 1 mM EDTA (need a 10-fold dilution)
100 uM polyA comp buffer (in green box in Chill-es Darwin)
For Binding Buffer
10 mL Tris HCl
10 mL LiCl
1 mL EDTA
29 mL water
For Low Salt Buffer
10 mL Tris HCl
4 mL LiCl
1 mL EDTA
35 mL water
Elution buffer
10 µM polyA complement buffer (This concentration can be titrated to improve for different situations)
10-fold dilution of 100 uM polyA comp stock (in protein lo-bind tube)

Step 3-Prep Magnetic Beads

Pipette 100 µL of Oligo d(T) magnetic beads into 2 mL DNA low-bind tube. Add 200 µL of Lysis binding buffer, vortex briefly and mix with agitation (shaken by hand) for 2 min.

Step 4-Binding

Place magnetic bead tube on magnetic rack for 1 minute (whenever magnetic bead is on rack, be sure not to rotate tube as it may cause loss of magnetic bead into solution). Remove Binding Buffer (should be ~300 µL) from tube. Add 5 µL crude polyA N.S. (decreasing the bead amount). Bring the volume up to 100 µL by adding 95 µL PBS. (NS volume can be changed/improved for different situations). Remove from magnetic rack, suspend by vortexing or shaking to get beads off tube wall, and agitate for 10 minutes. Place in magnetic rack for 1 minute before removing supernatant.

Step 5-Washes

Add 500 µL Binding buffer. Mix and agitate for 1 min. Place tube in magnetic rack for 1 minute then remove wash solution (Potentially keep wash solutions to analyze any NS loss). Repeat steps of step 5 10 times with Binding Buffer. Repeat previous steps once with Low Salt Buffer in place of Binding Buffer.

Step 6-Elute

Add 100 µL of polyA comp buffer, and vortex/shake to suspend beads. Mix and agitate for 30 minutes. Place tube in magnetic rack for 1 minute then remove and keep supernatant. Repeat steps of step 6 two more times.

Step 7-Prep and Run in Gel

Dilute the crude polyA nanoswitch 100-fold. Mix a negative control of 5 µL 100-fold diluted polyA nanoswitch+5 µL NF water. Mix a 5 µL 100-fold diluted polyA nanoswitch+5 µL 60 nM SA. Dilute the elutions 5-fold. (to have even amounts in each gel). For each 10-fold dilution, mix 5 µL of the elution 10-fold dilution+5 µL of water. The wash buffer solutions were not diluted. 2 µL of loading dye were added to 10 µL of each the new mixes, then the 12 µL were loaded onto a 7% 0.5×TBE gel. All the gel inputs were set to 2%. The gel is run at 200V for 30 minutes.

Conjugated Oligo Purification

When making antibody-oligo conjugates, it is important to be able to remove unconjugated oligonucleotide, as these can hybridize to a Nanoswitch resulting in un-loopable nanoswitches.

Purification of oligo conjugated with antibody can be accomplished with protein G and protein A beads. The Protein G and Protein A bind to the Fc region of an antibody, allowing for removal of any oligo that lacks and antibody thus enriching the conjugated oligo. Alternatively, beads coated with antigen (which would also bind to the antibody) may be used, or a small molecule or protein tag could be added to the antibody which could be bound by the beads.

The following protocol was used for protein G or protein A magnetic bead purification (adapted from Promega):
Materials to Be Supplied by the User
bind/wash buffer: 1×PBS
Pierce Gentle elution buffer AG/Ab (www.thermofisher.com/order/catalog/product/21030)
magnetic stand
mixing platform Gently vortex or invert the beads to obtain a uniform suspension. Keep the suspension uniform when aliquoting beads. Add 50 µl of bead slurry to a 1.5 ml microcentrifuge tube. Place in the magnetic stand for 10 seconds. Remove and discard the storage buffer. Add 500 µl of 1×PBS. Mix and place in the magnetic stand for 10 seconds. Remove and discard the 1×PBS. Combine 50 µl of 1×PBS and 50 µl of sample, then add to the equilibrated beads. Mix sample for 45 minutes at room temperature. Make sure the beads remain in suspension by using a tube shaker or end-over-end mixer. Place tube in the magnetic stand for 10 seconds. Remove the supernatant, and save for analysis if desired. Wash beads by adding 500 µl of 1×PBS and mix for 5 minutes. Place in the magnetic stand for 10 seconds. Remove and save for analysis if desired. Repeat the previous washing step for a total of two washes. Wash beads by adding 200 µl of 1×PBS. Mix and place in the magnetic stand for 10 seconds. Remove and save for analysis if desired. Add 50 µl of Gentle Elution Buffer to the beads. Mix for 5 minutes at room temperature. Repeat the elution steps.

Eluted samples can be combined. Buffer exchange the samples using a Zeba column into desired storage buffer (e.g. 10 mM sodium phosphate, 150 mM sodium chloride, 1 mM EDTA, 0.05% sodium azide, pH 7.2.)

Lyophilization/SpeedVac/Drying of Nanoswitches (To Increase Shelf Life)

Antibody conjugates and DNA nanoswitches can be stored in solution at 4° C. for up to 1 month. However, if stored at room temperature, the nanoswitch degrades much faster. Without wishing to be bound by theory, it is believed that storage of the Antibody conjugate or the DNA nanoswitch in a dry form can increase the shelf life and allow significant improvement of the final Nanoswitch concentration in the bodily fluid (which helps with the kinetics and fraction of analyte bound).

The concentration of the antibodies is very important to the nanoswitch hybridization, where the reaction efficiency depends directly on how dilute or concentrated the antibodies are. The drying procedure can be done using a SpeedVac or Lyophilizer. One potential problem associated with the use of a SpeedVac is that samples are dried at an elevated temperature, which has the potential of denaturing antibodies. SpeedVac'd antibody-oligo conjugates were run against control antibody-oligos to look for any loss of functionality.

Figure 22:
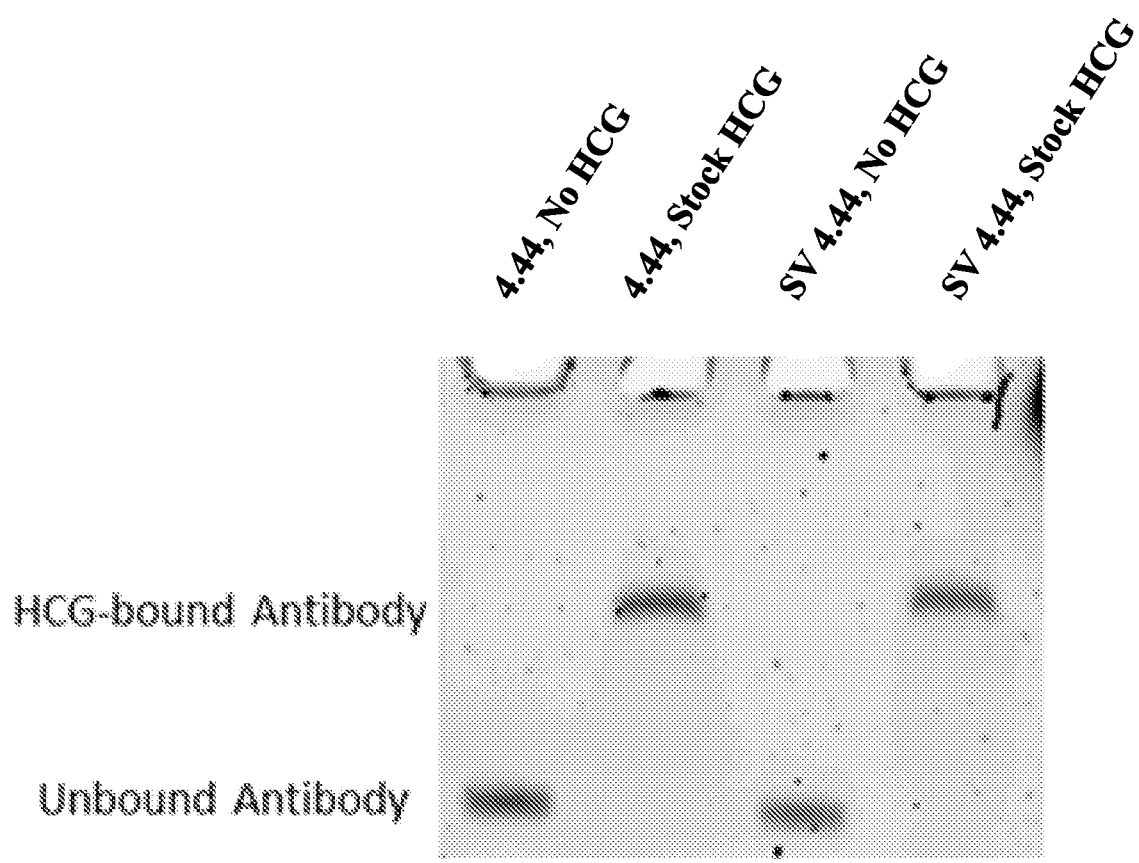
FIG. 22 demonstrates a functional testing (i.e., HCG binding) of individual antibody-oligos that were either dried using SpeedVac or control antibody-oligos.

Specifically, 5 µL purified (by BluePippin) 4.44-5011 and 5 µL purified 4.19-5008 were SpeedVac'd at medium temperature for the initial functionality test. All liquid was evaporated in the SpeedVac before re-suspending to the same volume with 5 µL PBS. To test functionality of the individual antibody-oligos, a polyacrylamide gel comparing HCG binding between the SpeedVac'd antibody-oligos and the control antibody-oligos were run (FIG. 22). Since HCG concentration in the positive lane should have been enough to saturate the antibodies, any unbound antibody band remaining would represent antibodies that had lost functionality and did not bind HCG.

As seen in FIG. 22, both the SpeedVac'd and non-SpeedVac'd Antibody-oligo conjugates showed an equal shift upon addition of HCG, suggesting no loss of functionality resulted from the SpeedVac drying procedure.

Room Temperature Hybridization Protocol

When hybridizing oligonucleotides to the Nanoswitch scaffold, they usually need to be heated to remove secondary structure. Antibody/Protein/Peptide oligo conjugates are often not tolerant of heating, as heating can denature proteins. This can lead to loss of functionality leading to decreased sensitivity, a complete lack of functionality, or aggregation which can cause false positive readings. Additionally, heating can lead to hydrolysis of the linker especially in the case of hydrazone linkages.

For this reason, when conjugating proteins to oligos, oligonucleotides which lack secondary structure were used so that they can hybridize at room temperature. A protocol was developed for optimal low temperature hybridization.

First all non-functionalized oligos were hybridized to the M13 scaffold by heating to 95° C. for 2 min and brought down to 35° C. at 1° C./min). Once at 35° C. the Antibodies-oligo conjugates were added to the scaffold, the temperature is held at 35° C. for 10 minutes, then dropped to 20° C. for 1 hour, and finally dropped to 4° C. for storage. This protocol enabled efficient hybridization of all oligos without the risk of denaturing the proteins on the functionalized oligos.

DNA Linearization

For DNA nanoswitches that use circular plasmids, the successful linearization of the plasmid prior to hybridizing the functionalized oligos is important for nanoswitch performance. Inefficient linearization can lead to a reduction in DNA nanoswitch yield. Additionally, the circular DNA runs close to the looped DNA nanoswitch providing false signal which could contaminate true signal.

This is especially important when trying to detect analyte at low concentrations. In this case, a high concentration of DNA nanoswitch is loaded in the gel. For example, if 500 pM of DNA nanoswitch is loaded, and the analyte is at 5 pM concentration, a 98% linear DNA nanoswitch, will have 10 pM of circular DNA, this can introduce significant noise into the readout.

Accordingly, an improved linearization process was developed to ensure linear DNA purity by adding in vast excess of restriction enzyme. Initially, the following agents were added to a clean PCR tube:
20 µL Single-Stranded M13mp18 (240 µg/mL)
2 µL BTSCI oligo
10 µL 10× NEBuffer2
52 µL NF H$_2$O The mixture was placed in a thermocycler, brought up to 90° C. for 1 minute, and dropped down to and held at 50° C. Subsequently, 16 µL BtsCI Enzyme (NEB R0647S) was added. The mixture was held at 50° C. for 1 hour. Heat inactivation of the enzyme was performed by heating the mixture to 95° C. for 1 minute. For this protocol, the BTSCI cut site oligo comprises the sequence: CTACTAATAGTAGTAGCATTAACATCCAATAAAT-CATACA (SEQ ID NO:19).

Circular DNA Purity

Figure 23:
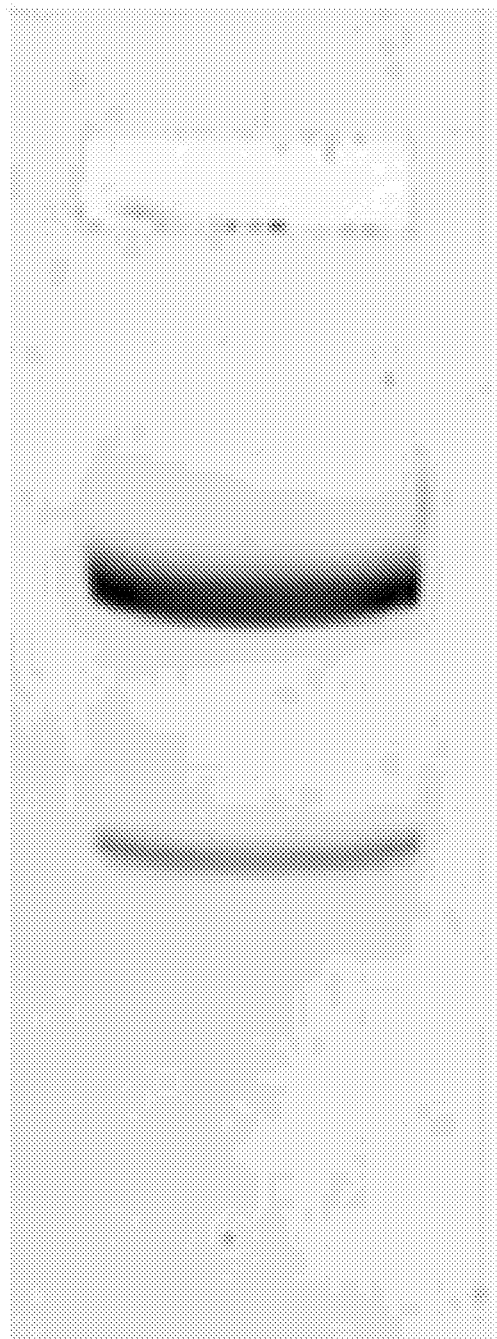
FIG. 23 depicts circular DNA purity. Between 70-80% circular purity was typically obtained when purchasing commercial M13.

For DNA nanoswitches that use circular ssDNA as scaffold sources, the circular purity of the source is important for functional nanoswitch yield and band quality. When purchasing circular M13 from a variety of sources, it was observed that the circular purity varied between 70-80% circular (see FIG. 23)

Circular DNA is usually converted to linear DNA through the addition of a cut-site oligo and digestion enzyme. Any DNA which is already linear will be further cut. This leads to a continuous distribution of shorter DNA fragments. This distribution manifests as a leading smear that runs below the linear DNA band. Fragments which have been cut between the two antibodies sites will lead to pieces of DNA which have only 1 antibody. These can bind up antigen in solution, but will not adopt a loop geometry, leading to a loss in analyte detection sensitivity. Other cuts result in loopable DNA nanoswitches which run to other locations thus diluting signals.

It was observed that M13 DNA from Tilibit was 99% circular. This resulted in a maximum yield of functional DNA nanoswitches.

Streamlining of Purification and Assembly Processes

The production of DNA nanoswitches with multiple antibodies is a possible next step in increasing detection limits of DNA nanoswitches. However, the purification of multiple antibodies in parallel can be time-consuming and expensive. The pooling method described herein ensures an equal-molar ratio of material as well as the separation of cross-reacting antibodies. Specifically, a protocol was developed for antibody-oligo pooling. The concentration of each antibody-oligo conjugate was calculated using a KBB gel electrophoresis with a 1 µM oligo standard from the intensity profile. Antibodies coupled to the same oligo were pooled into equimolar concentrations to create a Var-specific master mix. These antibody-oligo master mixes were then purified using protein A bead. Further purification included BluePippin improved recovery purification from 500-4000 bp range.

Affinity Based Purification: Temporal Elution to Purify Only Fully Functional Nanoswitches When assembling DNA nanoswitches with two antibodies on them, 3 species can form.
1) a species with two antibodies on it (The desired product-"Loopables")
2) a species with only one antibody on it (Antibody 1 or Antibody 2) (undesired products-"Halfers")
3) a species with no antibodies on it (Undesired products-"Unfunctionalized")

Figure 24:
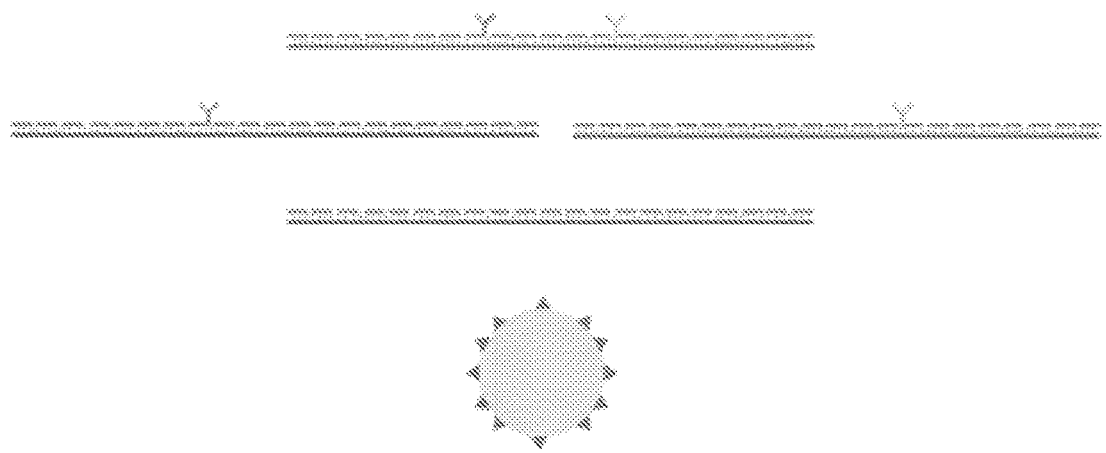
FIG. 24, panels A-G provides a schematic of the sequential affinity purification protocol describe herein. Panels H-K provides a schematic of the temporal affinity purification protocol described herein.
Figure 24:
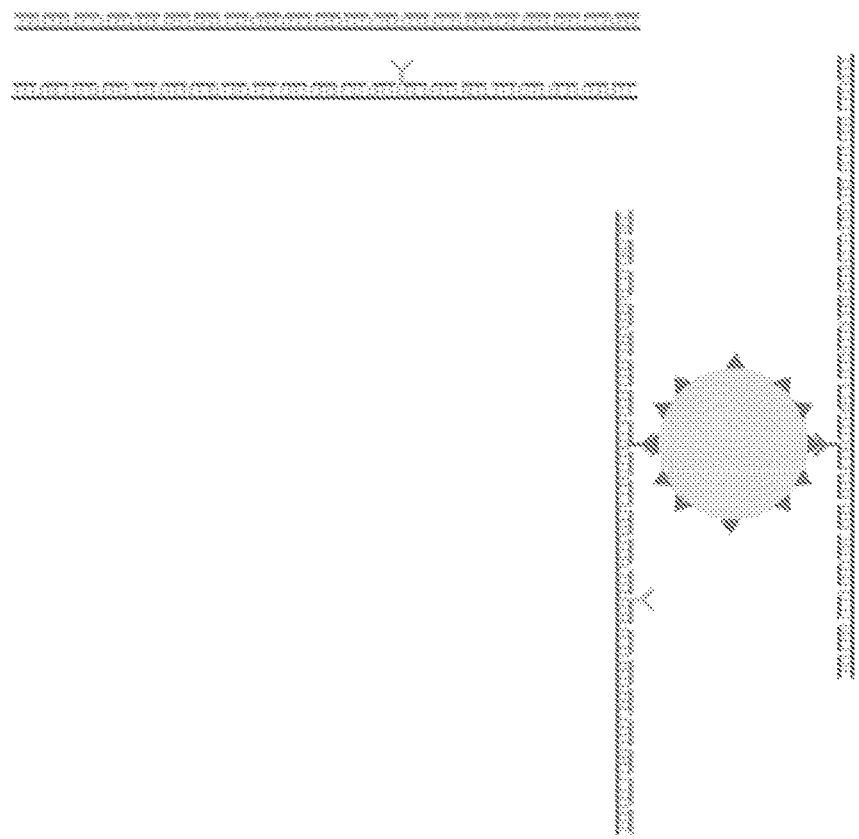
Figure 24:
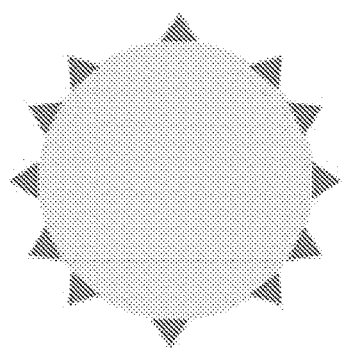
Figure 24:
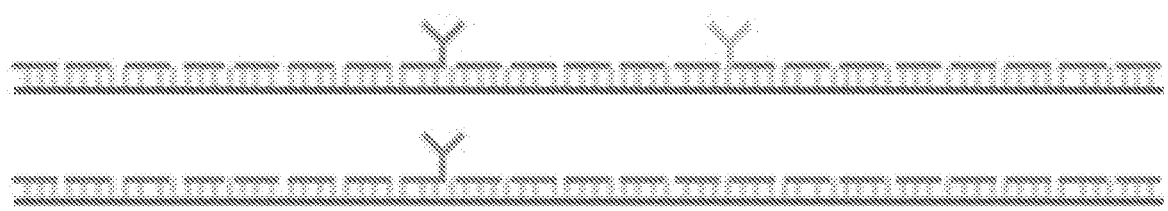
Figure 24:
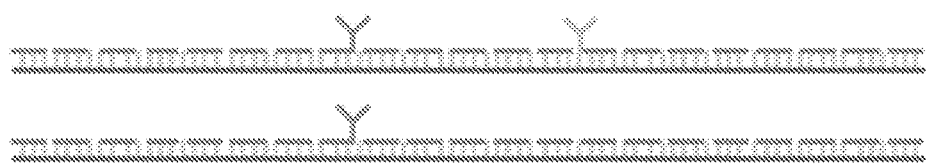
Figure 24:
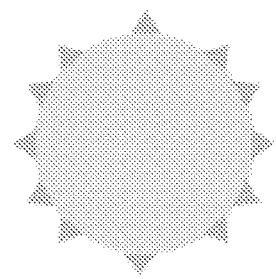
Figure 24:
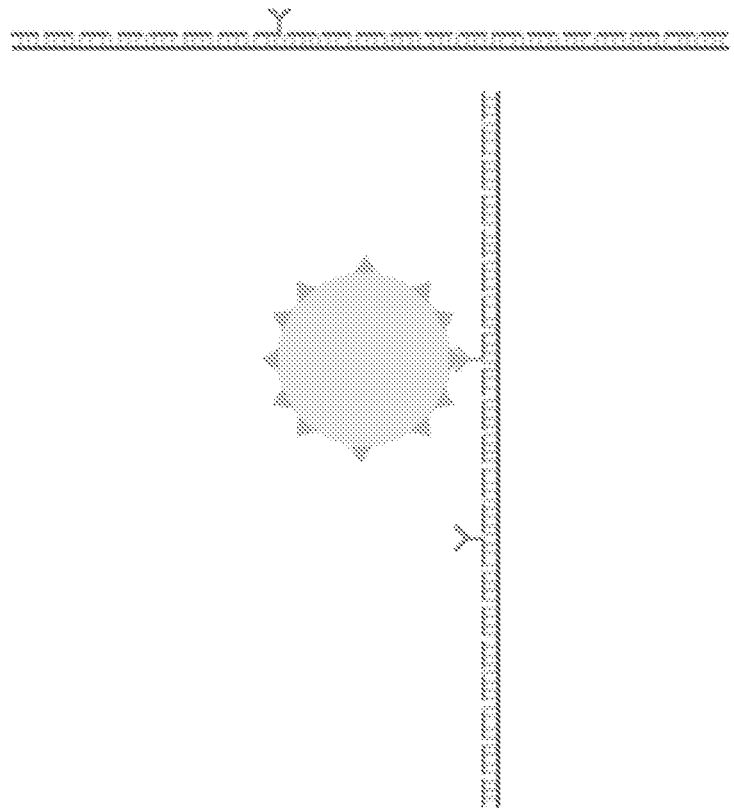
Figure 24:
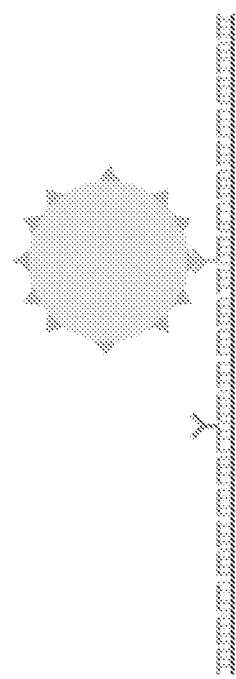
Figure 24:
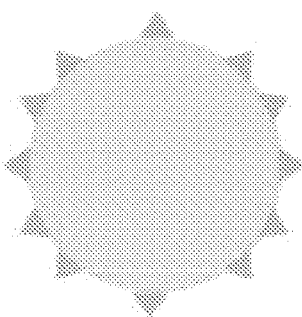
Figure 24:
Figure 24:
Figure 24:
Figure 24:
Figure 24:
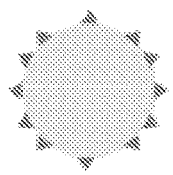
Figure 24:
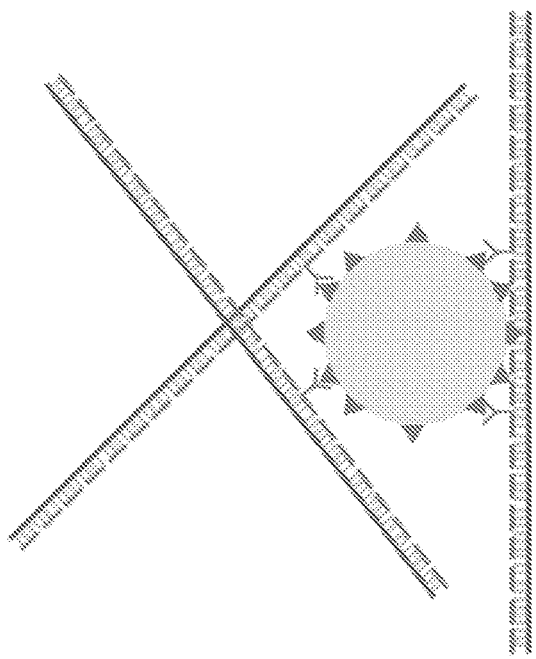
Figure 24:
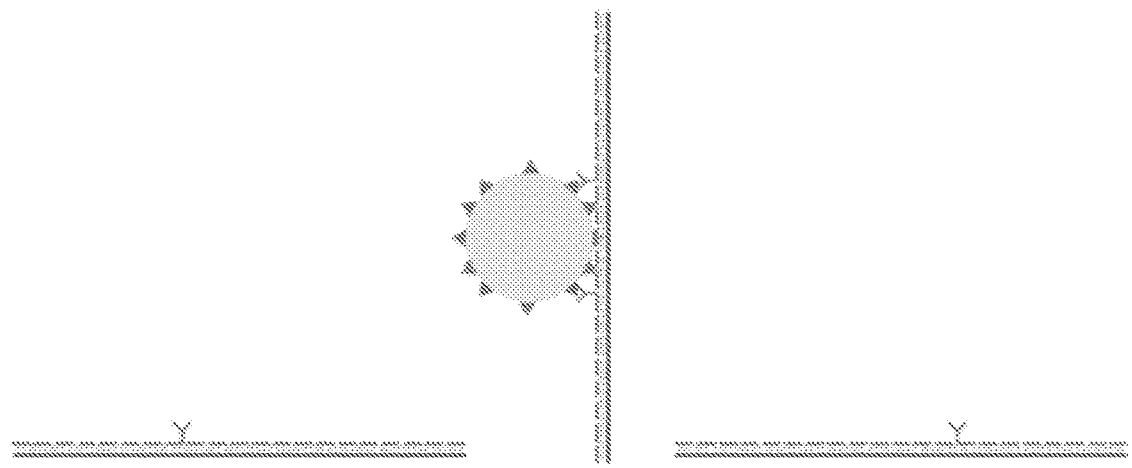
Figure 24:
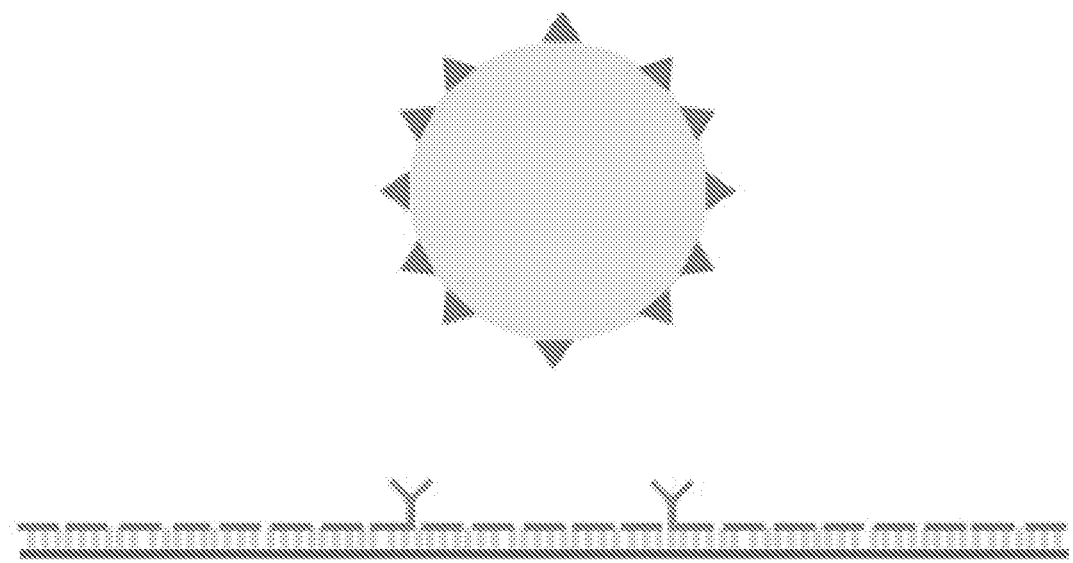

A method was developed for selectively purifying out loopables to enrich the population of the desired species from a crude mixture (See FIG. 24, panels A-K). Specifically, the following two methods were developed:

Sequential affinity purification in which the nanoswitches could be incubated with beads functionalized with the epitope that binds to Antibody 1. Removal of the supernatant and washing of the beads would eliminate all unfunctionalized constructs, and half of the Halfers (those that only contain Antibody 2). Once the nanoswitches were released from the beads they could be incubated with beads with functionalized epitope that binds to antibody 2. Removal of the supernatant and washing of the beads would eliminate all the remaining Halfers (those that only contain Antibody 1). See FIG. 24, panels A-G.

Temporal affinity purification is similar to the sequential purification, but rather than requiring two different epitopes, this method used the fact that nanoswitches with two antibodies would bind more tightly to an antigen functionalized bead than will nanoswitches with only one antibody. Incubate the nanoswitches with antigen-functionalized beads, followed by removal of the supernatant and washing of the beads, which would eliminate all unfunctionalized constructs. Placing these beads in a column and applying flow would allow removal of the Halfers which will unbind long before the Loopables. The Loopables could then be eluted from the beads and collected. See FIG. 24, panels H-K.

Example 8. Improvement of Imaging

Background Subtraction

Figure 25:
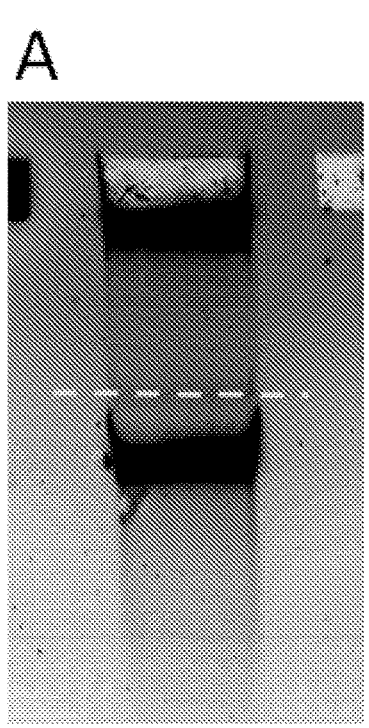
FIG. 25, panel A, provides image of a gel lane. The dotted line indicates a row along which the intensity was analyzed to determine if the background is inhomogeneous. Panel B provides a plot of the intensity profile of the row as a function of the pixel location. The dotted line indicates the slope of the background signal. This line was subtracted from the profile before any further analysis was done.
Figure 25:
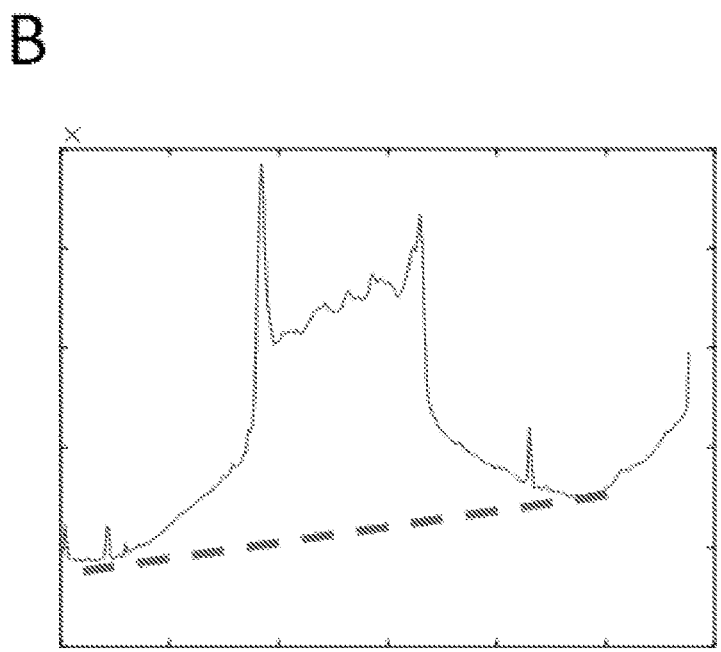

The intensity at each point in a gel image is the sum of the intensity resulting from the DNA present at that location and any background signal. Typically, when analyzing a gel, the intensity in each row is either summed or averaged to obtain a 1D Intensity profile. Background is then subtracted from the resulting 1D profile. This is appropriate if the background signal is homogeneous. However, this is often not the case (see FIG. 25, panel A). The background typically has a characteristic slope to it. Without correcting for this, the resulting analysis can be biased. As shown in FIG. 25, panel B, background can be subtracted from the gel images prior to analysis so as to achieve a more unbiased analysis of DNA gels.

Analysis by Column for Statistical Support

A typical method of analyzing a gel lane is to take the mean/median, or some other ranked filter of each row to form a 1D intensity profile. Following this the area of the looped band is calculated to estimate the amount of analyte detected in the looped band. Rather than analyze this average profile, each individual column in a gel lane can be analyzed, and the area of the looped band measured. By using this as a population of measurements rather than a single measurement, one can fit the population and estimate the error in analyte detection measurement.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50%" covers the range of 45% to 55%.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the technology described herein that do not contain those elements or features.

Although the open-ended term "comprising," as a synonym of terms such as including, containing, or having, is used herein to describe and claim the invention, the invention described herein, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of this application. Nothing herein is to be construed as an admission that the invention described herein is not entitled to antedate such publication by virtue of prior invention.

As used herein, all headings are simply for organization and are not intended to limit the disclosure in any manner. The content of any individual section may be equally applicable to all sections.

The invention claimed is:

1. A biomarker test system comprising:
a nanoswitch source comprising a nanoswitch for detecting a biomarker in a sample, the nanoswitch comprising:
a nucleic acid scaffold;
a set of binding partners that are linked to the nucleic acid scaffold or one or more oligonucleotides hybridized to the nucleic acid scaffold, the set of binding partners being configured to bind the biomarker such that the binding causes the nucleic acid scaffold to change a conformation to form a detectable loop;
a sample receiver configured to receive the sample; and
a gel electrophoresis medium in fluid communication with the nanoswitch source and the sample receiver, the gel electrophoresis medium being configured to detect the conformation of the nucleic acid scaffold,
wherein the set of binding partners further comprises a pair of control binding partners configured to bind a control analyte present in the sample.

2. The biomarker test system of claim 1, wherein the set of binding partners comprises a first pair of binding partners comprising a first binding partner and a second binding partner disposed separately from the first binding partner, the first and second binding partners being configured to simultaneously bind the biomarker when the biomarker is present in the sample to thereby cause the nucleic acid scaffold to form the detectable loop.

3. The biomarker test system of claim 2, wherein the first and second binding partners are antibodies selected from one or more of an anti-luteinizing hormone (LH) antibody, an anti-estrone 3-glucuronide antibody, an anti-hCG antibody, an anti-prostate specific antigen antibody, an anti-streptococcus A antibody, an anti-chlamydia antibody, an anti-gonorrhea antibody, an anti-hemoglobin A1C antibody, and an anti-C-reactive protein antibody.

4. The biomarker test system of claim 3, wherein the antibody is an anti-prostate specific antigen antibody and wherein the anti-prostate specific antigen antibody comprises one or more of anti-PSA 5001, anti-PSA 5012, and functional fragments thereof.

5. The biomarker test system of claim 3, wherein the antibody is an anti-streptococcus A antibody and wherein the anti-streptococcus A antibody comprises one or more of anti-strepA 2601 SPTN-5, anti-strepA 2603, and functional fragments thereof.

6. The biomarker test system of claim 3, wherein the antibody is an anti-chlamydia antibody and wherein the anti-chlamydia antibody comprises one or more of anti-chlamydia 6701 SP-5, anti-chlamydia 6703 SPRN-5, anti-chlamydia 6703 SPRN-5, ab20881, ab20767, ab41193, and functional fragments thereof.

7. The biomarker test system of claim 3, wherein the antibody is an anti-gonorrhea antibody and wherein the anti-gonorrhea antibody comprises one or more of ab19962, ab62964, ab40998, ab21096, and functional fragments thereof.

8. A biomarker test system comprising:
a nanoswitch source comprising a nanoswitch for detecting a biomarker in a sample, the nanoswitch comprising:
a nucleic acid scaffold;
a set of binding partners that are linked to the nucleic acid scaffold or one or more oligonucleotides hybridized to the nucleic acid scaffold, the set of binding partners being configured to bind the biomarker such that the binding causes the nucleic acid scaffold to change a conformation to form a detectable loop;
a sample receiver configured to receive the sample; and
a gel electrophoresis medium in fluid communication with the nanoswitch source and the sample receiver, the gel electrophoresis medium being configured to detect the conformation of the nucleic acid scaffold,
wherein the set of binding partners comprises a first pair of binding partners comprising a first binding partner and a second binding partner disposed separately from the first binding partner, the first and second binding partners being configured to simultaneously bind the biomarker when the biomarker is present in the sample to thereby cause the nucleic acid scaffold to form the detectable loop, and
wherein the set of binding partners further comprises a second pair of binding partners comprising a third binding partner comprising a third antibody and a fourth binding partner comprising a fourth antibody, the third and fourth binding partners being configured to simultaneously bind a second biomarker present in the sample to thereby form a second detectable loop.

9. The biomarker test system of claim 8, wherein the first and second binding partners are antibodies selected from one or more of an anti-luteinizing hormone (LH) antibody, an anti-estrone 3-glucuronide antibody, an anti-hCG antibody, an anti-prostate specific antigen antibody, an anti-streptococcus A antibody, an anti-chlamydia antibody, an anti-gonorrhea antibody, an anti-hemoglobin A1C antibody, and an anti-C-reactive protein antibody.

10. The biomarker test system of claim 9, wherein the antibody is an anti-prostate specific antigen antibody and wherein the anti-prostate specific antigen antibody comprises one or more of anti-PSA 5001, anti-PSA 5012, and functional fragments thereof.

11. The biomarker test system of claim 9, wherein the antibody is an anti-streptococcus A antibody and wherein the anti-streptococcus A antibody comprises one or more of anti-strepA 2601 SPTN-5, anti-strepA 2603, and functional fragments thereof.

12. The biomarker test system of claim 9, wherein the antibody is an anti-chlamydia antibody and wherein the anti-chlamydia antibody comprises one or more of anti-chlamydia 6701 SP-5, anti-chlamydia 6703 SPRN-5, anti-chlamydia 6703 SPRN-5, ab20881, ab20767, ab41193, and functional fragments thereof.

13. The biomarker test system of claim 9, wherein the antibody is an anti-gonorrhea antibody and wherein the anti-gonorrhea antibody comprises one or more of ab19962, ab62964, ab40998, ab21096, and functional fragments thereof.

14. The biomarker test system of claim 8, wherein the first and second binding partners each comprise an anti-hCG antibody, and the third and fourth binding partners each comprise an anti-LH antibody.

15. The biomarker test system of claim 14, wherein the anti-LH antibody comprises one or more of Fitzgerald 10-L15A, Fitzgerald 10-L15B, and functional fragments thereof.

16. The biomarker test system of claim 14, wherein the anti-hCG antibody comprises one or more of INN-hCG-2, INN-hCG-22, 5008-SP5, 5014-SPTN5, 5011 SPRN-1, and functional fragments thereof.

17. The biomarker test system of claim 8, wherein the set of binding partners further comprises a third pair of binding partners comprising a fifth binding partner and a sixth binding partner, the fifth and sixth binding partners being configured to simultaneously bind a control analyte present in the sample.

18. The biomarker test system of claim 17, wherein the biomarker test system is configured such that, upon being brought in contact with the sample, the first pair of binding partners, the second pairs of binding partners, and the third pair of binding partners are provided to respective separate lanes in the gel electrophoresis medium, wherein the gel electrophoresis medium is pre-stained.

19. The biomarker test system of claim 18, wherein the biomarker test system is manufactured as a kit for simultaneous ovulation and pregnancy testing.

20. A biomarker test system comprising:
a nanoswitch source comprising a nanoswitch for detecting a biomarker in a sample, the nanoswitch comprising:
a nucleic acid scaffold;
a set of binding partners that are linked to the nucleic acid scaffold or one or more oligonucleotides hybridized to the nucleic acid scaffold, the set of binding partners being configured to bind the biomarker such that the binding causes the nucleic acid scaffold to change a conformation to form a detectable loop;
a sample receiver configured to receive the sample; and
a gel electrophoresis medium in fluid communication with the nanoswitch source and the sample receiver, the gel electrophoresis medium being configured to detect the conformation of the nucleic acid scaffold, wherein the set of binding partners comprises a first pair of binding partners comprising a first binding partner and a second binding partner disposed separately from the first binding partner, the first and second binding partners being configured to simultaneously bind the biomarker when the biomarker is present in the sample to thereby cause the nucleic acid scaffold to form the detectable loop, and wherein the nanoswitch further comprises a pair of latch oligonucleotides linked to the nucleic acid scaffold such that they are disposed between the first and second binding partners and such that the oligonucleotides of the pair of latch oligonucleotides are linked to one another thereby forming an inner loop and positioning the first and second binding partners closer to one another than in a configuration of the nucleic acid scaffold prior to the formation of the inner loop.

21. The biomarker test system of claim 20, wherein the first and second binding partners are antibodies selected from one or more of an anti-luteinizing hormone (LH) antibody, an anti-estrone 3-glucuronide antibody, an anti-hCG antibody, an anti-prostate specific antigen antibody, an anti-streptococcus A antibody, an anti-chlamydia antibody, an anti-gonorrhea antibody, an anti-hemoglobin A1C antibody, and an anti-C-reactive protein antibody.

22. The biomarker test system of claim 21, wherein the antibody is an anti-prostate specific antigen antibody and wherein the anti-prostate specific antigen antibody comprises one or more of anti-PSA 5001, anti-PSA 5012, and functional fragments thereof.

23. The biomarker test system of claim 21, wherein the antibody is an anti-streptococcus A antibody and wherein the anti-streptococcus A antibody comprises one or more of anti-strepA 2601 SPTN-5, anti-strepA 2603, and functional fragments thereof.

24. The biomarker test system of claim 21, wherein the antibody is an anti-chlamydia antibody and wherein the anti-chlamydia antibody comprises one or more of anti-chlamydia 6701 SP-5, anti-chlamydia 6703 SPRN-5, anti-chlamydia 6703 SPRN-5, ab20881, ab20767, ab41193, and functional fragments thereof.

25. The biomarker test system of claim 21, wherein the antibody is an anti-gonorrhea antibody and wherein the anti-gonorrhea antibody comprises one or more of ab19962, ab62964, ab40998, ab21096, and functional fragments thereof.

26. The biomarker test system of claim 20, wherein the formation of the inner loop is reversible.

27. The biomarker test system of claim 20, wherein the binding the biomarker by the first and second binding partners causes the nucleic acid scaffold to form the detectable loop that is an outer loop having a size different than a size of the inner loop.

28. The biomarker test system of claim 27, wherein the size of the outer loop is larger than the size of the inner loop.

29. The biomarker test system of claim 27, wherein the first and second binding partners are single-stranded extension oligonucleotides hybridized to the nucleic acid scaffold in proximity to the oligonucleotides of the pair of latch oligonucleotides, so that binding, by the first and second binding partners, the biomarker comprising a DNA strand having a sequence that is at least partially complementary to the single-strand extension oligonucleotides causes formation of the detectable loop.

* * * * *

```
                              SEQUENCE LISTING

<160> NUMBER OF SEQ ID NOS: 147

<210> SEQ ID NO 1
<211> LENGTH: 40
<212> TYPE: DNA
<213> ORGANISM: ARTIFICIAL SEQUENCE
<220> FEATURE:
<223> OTHER INFORMATION: single strand nucleic acid scaffold

<400> SEQUENCE: 1
ctcaaatatc aaaccctcaa tcaatatctg gtcagttggc                           40

<210> SEQ ID NO 2
<211> LENGTH: 45
<212> TYPE: DNA
<213> ORGANISM: ARTIFICIAL SEQUENCE
<220> FEATURE:
<223> OTHER INFORMATION: single strand nucleic acid scaffold

<400> SEQUENCE: 2
actatatgta aatgctgatg caaatccaat cgcaagacaa agaac                      45

<210> SEQ ID NO 3
<211> LENGTH: 54
<212> TYPE: PRT
<213> ORGANISM: Artificial Sequence
<220> FEATURE:
<223> OTHER INFORMATION: azide-functionalized HSV-2 peptide

<400> SEQUENCE: 3

Arg Gly Thr Ala Arg Thr Pro Pro Thr Asp Pro Lys Thr His Pro His
1               5                   10                  15

Gly Pro Ala Asp Ala Pro Pro Gly Ser Pro Ala Pro Pro Pro Pro Glu
            20                  25                  30

His Arg Gly Gly Pro Glu Glu Phe Glu Gly Ala Gly Asp Gly Glu Pro
        35                  40                  45

Pro Glu Asp Asp Asp Ser
    50

<210> SEQ ID NO 4
<211> LENGTH: 29
<212> TYPE: DNA
<213> ORGANISM: ARTIFICIAL SEQUENCE
<220> FEATURE:
```

<223> OTHER INFORMATION: single strand nucleic acid scaffold

<400> SEQUENCE: 4
ctcaaatatc aaaccctcaa tcaatatct                                29

<210> SEQ ID NO 5
<211> LENGTH: 28
<212> TYPE: DNA
<213> ORGANISM: ARTIFICIAL SEQUENCE
<220> FEATURE:
<223> OTHER INFORMATION: single strand nucleic acid scaffold

<400> SEQUENCE: 5
ttggcaaatc aacagttgaa aggaattg                                 28

<210> SEQ ID NO 6
<211> LENGTH: 24
<212> TYPE: DNA
<213> ORGANISM: ARTIFICIAL SEQUENCE
<220> FEATURE:
<223> OTHER INFORMATION: single strand nucleic acid scaffold

<400> SEQUENCE: 6
ataactatat gtaaatgctg atgc                                    24

<210> SEQ ID NO 7
<211> LENGTH: 24
<212> TYPE: DNA
<213> ORGANISM: ARTIFICIAL SEQUENCE
<220> FEATURE:
<223> OTHER INFORMATION: single strand nucleic acid scaffold

<400> SEQUENCE: 7
aaatccaatc gcaagacaaa gaac                                    24

<210> SEQ ID NO 8
<211> LENGTH: 20
<212> TYPE: DNA
<213> ORGANISM: Artificial Sequence
<220> FEATURE:
<223> OTHER INFORMATION: single strand nucleic acid scaffold

<400> SEQUENCE: 8
caccttgctg aacctcaaat                                         20

<210> SEQ ID NO 9
<211> LENGTH: 20
<212> TYPE: DNA
<213> ORGANISM: Artificial Sequence
<220> FEATURE:
<223> OTHER INFORMATION: single strand nucleic acid scaffold

<400> SEQUENCE: 9
atcaaaccct caatcaatat                                         20

<210> SEQ ID NO 10
<211> LENGTH: 20
<212> TYPE: DNA
<213> ORGANISM: Artificial Sequence
<220> FEATURE:
<223> OTHER INFORMATION: single strand nucleic acid scaffold

<400> SEQUENCE: 10
ctggtcagtt ggcaaatcaa                                         20

```
<210> SEQ ID NO 11
<211> LENGTH: 20
<212> TYPE: DNA
<213> ORGANISM: Artificial Sequence
<220> FEATURE:
<223> OTHER INFORMATION: single strand nucleic acid scaffold

<400> SEQUENCE: 11
caccttgctg aacctcaaat                                                   20

<210> SEQ ID NO 12
<211> LENGTH: 20
<212> TYPE: DNA
<213> ORGANISM: Artificial Sequence
<220> FEATURE:
<223> OTHER INFORMATION: single strand nucleic acid scaffold

<400> SEQUENCE: 12
cagttgaaag gaattgagga                                                   20

<210> SEQ ID NO 13
<211> LENGTH: 20
<212> TYPE: DNA
<213> ORGANISM: Artificial Sequence
<220> FEATURE:
<223> OTHER INFORMATION: single strand nucleic acid scaffold

<400> SEQUENCE: 13
aggttatcta aaatatcttt                                                   20

<210> SEQ ID NO 14
<211> LENGTH: 20
<212> TYPE: DNA
<213> ORGANISM: Artificial Sequence
<220> FEATURE:
<223> OTHER INFORMATION: single strand nucleic acid scaffold

<400> SEQUENCE: 14
gagaagagtc aatagtgaat                                                   20

<210> SEQ ID NO 15
<211> LENGTH: 20
<212> TYPE: DNA
<213> ORGANISM: Artificial Sequence
<220> FEATURE:
<223> OTHER INFORMATION: single strand nucleic acid scaffold

<400> SEQUENCE: 15
ttatcaaaat cataggtctg                                                   20

<210> SEQ ID NO 16
<211> LENGTH: 19
<212> TYPE: DNA
<213> ORGANISM: Artificial Sequence
<220> FEATURE:
<223> OTHER INFORMATION: single strand nucleic acid scaffold

<400> SEQUENCE: 16
agagactacc tttttaacc                                                    19

<210> SEQ ID NO 17
<211> LENGTH: 19
<212> TYPE: DNA
<213> ORGANISM: Artificial Sequence
<220> FEATURE:
<223> OTHER INFORMATION: single strand nucleic acid scaffold
```

<400> SEQUENCE: 17
agagactacc tttttaacc                                                    19

<210> SEQ ID NO 18
<211> LENGTH: 20
<212> TYPE: DNA
<213> ORGANISM: Artificial Sequence
<220> FEATURE:
<223> OTHER INFORMATION: single strand nucleic acid scaffold

<400> SEQUENCE: 18
tccggcttag gttgggttat                                                   20

<210> SEQ ID NO 19
<211> LENGTH: 40
<212> TYPE: DNA
<213> ORGANISM: Artificial Sequence
<220> FEATURE:
<223> OTHER INFORMATION: BTSC1 cut site oligonucleotide

<400> SEQUENCE: 19
ctactaatag tagtagcatt aacatccaat aaatcataca                             40

<210> SEQ ID NO 20
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 20
caatatatgt gagtgaataa ccttgcttct gtaaatcgtc gctattaatt aattttccct       60

<210> SEQ ID NO 21
<211> LENGTH: 48
<212> TYPE: DNA
<213> ORGANISM: Artificial Sequence
<220> FEATURE:
<223> OTHER INFORMATION: single strand nucleic acid scaffold

<400> SEQUENCE: 21
ataactatat gtaaatgctg atgcaaatcc aatcgcaaga caaagaac                    48

<210> SEQ ID NO 22
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 22
ctgaacaaga aaataatat cccatcctaa tttacgagca tgtagaaacc aatcaataat        60

<210> SEQ ID NO 23
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 23
ttgtttaacg tcaaaaatga aaatagcagc ctttacagag agaataacat aaaaacaggg       60

<210> SEQ ID NO 24
<211> LENGTH: 25

```
<212> TYPE: DNA
<213> ORGANISM: Artificial Sequence
<220> FEATURE:
<223> OTHER INFORMATION: single strand nucleic acid scaffold

<400> SEQUENCE: 24
taccgagctc gaattcgtaa tcatg                                              25

<210> SEQ ID NO 25
<211> LENGTH: 25
<212> TYPE: DNA
<213> ORGANISM: Artificial Sequence
<220> FEATURE:
<223> OTHER INFORMATION: single strand nucleic acid scaffold

<400> SEQUENCE: 25
ggccagtgcc aagctttcag aggtg                                              25

<210> SEQ ID NO 26
<211> LENGTH: 25
<212> TYPE: DNA
<213> ORGANISM: Artificial Sequence
<220> FEATURE:
<223> OTHER INFORMATION: single strand nucleic acid scaffold

<400> SEQUENCE: 26
ggccagtgcc aagcttgcat gcctg                                              25

<210> SEQ ID NO 27
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 27
agagcataaa gctaaatcgg ttgtaccaaa acattatga ccctgtaata cttttgcggg         60

<210> SEQ ID NO 28
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 28
agaagccttt atttcaacgc aaggataaaa atttttagaa ccctcatata ttttaaatgc         60

<210> SEQ ID NO 29
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 29
aatgcctgag taatgtgtag gtaaagattc aaaagggtga gaaggccgg agacagtcaa         60

<210> SEQ ID NO 30
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 30
```
atcaccatca atatgatatt caaccgttct agctgataaa ttaatgccgg agagggtagc    60

<210> SEQ ID NO 31
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 31
tatttttgag agatctacaa aggctatcag gtcattgcct gagagtctgg agcaaacaag    60

<210> SEQ ID NO 32
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 32
agaatcgatg aacggtaatc gtaaaactag catgtcaatc atatgtaccc cggttgataa    60

<210> SEQ ID NO 33
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 33
tcagaaaagc cccaaaaaca ggaagattgt ataagcaaat atttaaattg taaacgttaa    60

<210> SEQ ID NO 34
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 34
tattttgtta aaattcgcat taaattttg ttaaatcagc tcatttttta accaatagga    60

<210> SEQ ID NO 35
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 35
acgccatcaa aaataattcg cgtctggcct tcctgtagcc agctttcatc aacattaaat    60

<210> SEQ ID NO 36
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 36
ggataggtca cgttggtgta gatgggcgca tcgtaaccgt gcatctgcca gtttgagggg    60

<210> SEQ ID NO 37
<211> LENGTH: 60
<212> TYPE: DNA
<213> ORGANISM: Artificial Sequence

```
<220> FEATURE:
<223> OTHER INFORMATION: single strand nucleic acid scaffold

<400> SEQUENCE: 37
acgacgacag tatcggcctc aggaagatcg cactccagcc agctttccgg caccgcttct    60

<210> SEQ ID NO 38
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 38
ggtgccggaa accaggcaaa gcgccattcg ccattcaggc tgcgcaactg ttgggaaggg    60

<210> SEQ ID NO 39
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 39
cgatcggtgc gggcctcttc gctattacgc cagctggcga aaggggatg tgctgcaagg    60

<210> SEQ ID NO 40
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 40
cgattaagtt gggtaacgcc agggttttcc cagtcacgac gttgtaaaac gacggccagt    60

<210> SEQ ID NO 41
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 41
gccaagcttg catgcctgca ggtcgactct agaggatccc cgggtaccga gctcgaattc    60

<210> SEQ ID NO 42
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 42
gtaatcatgg tcatagctgt ttcctgtgtg aaattgttat ccgctcacaa ttccacacaa    60

<210> SEQ ID NO 43
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 43
catacgagcc ggaagcataa agtgtaaagc ctggggtgcc taatgagtga gctaactcac    60
```

<210> SEQ ID NO 44
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 44
attaattgcg ttgcgctcac tgcccgcttt ccagtcggga aacctgtcgt gccagctgca    60

<210> SEQ ID NO 45
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 45
ttaatgaatc ggccaacgcg cggggagagg cggtttgcgt attgggcgcc agggtggttt    60

<210> SEQ ID NO 46
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 46
gttgcagcaa gcggtccacg ctggtttgcc ccagcaggcg aaaatcctgt ttgatggtgg    60

<210> SEQ ID NO 47
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 47
ttccgaaatc ggcaaaatcc cttataaatc aaaagaatag cccgagatag ggttgagtgt    60

<210> SEQ ID NO 48
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 48
tgttccagtt tggaacaaga gtccactatt aaagaacgtg gactccaacg tcaaagggcg    60

<210> SEQ ID NO 49
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 49
aaaaaccgtc tatcagggcg atggcccact acgtgaacca tcacccaaat caagtttttt    60

<210> SEQ ID NO 50
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 50
ggggtcgagg tgccgtaaag cactaaatcg aaccctaaa gggagccccc gatttagagc    60

<210> SEQ ID NO 51
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 51
ttgacgggga agccggcga acgtggcgag aaaggaaggg aagaaagcga aaggagcggg    60

<210> SEQ ID NO 52
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 52
cgctagggcg ctggcaagtg tagcggtcac gctgcgcgta accaccacac ccgccgcgct    60

<210> SEQ ID NO 53
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 53
taatgcgccg ctacagggcg cgtactatgg ttgctttgac gagcacgtat aacgtgcttt    60

<210> SEQ ID NO 54
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 54
cctcgttaga atcagagcgg gagctaaaca ggaggccgat taagggatt ttagacagga    60

<210> SEQ ID NO 55
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 55
acggtacgcc agaatcctga gaagtgtttt tataatcagt gaggccaccg agtaaaagag    60

<210> SEQ ID NO 56
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 56
ttgcctgagt agaagaactc aaactatcgg ccttgctggt aatatccaga acaatattac    60

<210> SEQ ID NO 57

<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 57
cgccagccat tgcaacagga aaaacgctca tggaaatacc tacattttga cgctcaatcg    60

<210> SEQ ID NO 58
<211> LENGTH: 60
<212> TYPE: DNA
<213> ORGANISM: Artificial Sequence
<220> FEATURE:
<223> OTHER INFORMATION: 4.03

<400> SEQUENCE: 58
tctgaaatgg attatttaca ttggcagatt caccagtcac acgaccagta ataaaaggga    60

<210> SEQ ID NO 59
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 59
cattctggcc aacagagata gaacccttct gacctgaaag cgtaagaata cgtggcacag    60

<210> SEQ ID NO 60
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 60
acaatatttt tgaatggcta ttagtcttta atgcgcgaac tgatagccct aaaacatcgc    60

<210> SEQ ID NO 61
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 61
cattaaaaat accgaacgaa ccaccagcag aagataaaac agaggtgagg cggtcagtat    60

<210> SEQ ID NO 62
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 62
taacaccgcc tgcaacagtg ccacgctgag agccagcagc aaatgaaaaa tctaaagcat    60

<210> SEQ ID NO 63
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 63
caccttgctg aacctcaaat atcaaaccct caatcaatat ctggtcagtt ggcaaatcaa    60

<210> SEQ ID NO 64
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 64
cagttgaaag gaattgagga aggttatcta aaatatcttt aggagcacta acaactaata    60

<210> SEQ ID NO 65
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 65
gattagagcc gtcaatagat aatacatttg aggatttaga agtattagac tttacaaaca    60

<210> SEQ ID NO 66
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 66
cattatcatt ttgcggaaca aagaaaccac cagaaggagc ggaattatca tcatattcct    60

<210> SEQ ID NO 67
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 67
gattatcaga tgatggcaat tcatcaatat aatcctgatt gtttggatta tacttctgaa    60

<210> SEQ ID NO 68
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 68
taatggaagg gttagaacct accatatcaa aattatttgc acgtaaaaca gaaataaaga    60

<210> SEQ ID NO 69
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 69
aattgcgtag attttcaggt ttaacgtcag atgaatatac agtaacagta ccttttacat    60

<210> SEQ ID NO 70
<211> LENGTH: 60
<212> TYPE: DNA

<213> ORGANISM: Artificial Sequence
<220> FEATURE:
<223> OTHER INFORMATION: single strand nucleic acid scaffold

<400> SEQUENCE: 70
cgggagaaac aataacggat tcgcctgatt gctttgaata ccaagttaca aaatcgcgca    60

<210> SEQ ID NO 71
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 71
gaggcgaatt attcatttca attacctgag caaagaaga tgatgaaaca aacatcaaga    60

<210> SEQ ID NO 72
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 72
aaacaaaatt aattacattt aacaatttca tttgaattac cttttttaat ggaaacagta    60

<210> SEQ ID NO 73
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 73
cataaatcaa tatatgtgag tgaataacct tgcttctgta aatcgtcgct attaattaat    60

<210> SEQ ID NO 74
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 74
tttcccttag aatccttgaa aacatagcga tagcttagat taagacgctg agaagagtca    60

<210> SEQ ID NO 75
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 75
atagtgaatt tatcaaaatc ataggtctga gagactacct ttttaacctc cggcttaggt    60

<210> SEQ ID NO 76
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 76
gaaaactttt tcaaatatat tttagttaat ttcatcttct gacctaaatt taatggtttg    60

<210> SEQ ID NO 77
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 77
aaataccgac cgtgtgataa ataaggcgtt aaataagaat aaacaccgga atcataatta    60

<210> SEQ ID NO 78
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 78
ctagaaaaag cctgtttagt atcatatgcg ttatacaaat tcttaccagt ataaagccaa    60

<210> SEQ ID NO 79
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 79
cgctcaacag tagggcttaa ttgagaatcg ccatatttaa caacgccaac atgtaattta    60

<210> SEQ ID NO 80
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 80
ggcagaggca ttttcgagcc agtaataaga gaatataaag taccgacaaa aggtaaagta    60

<210> SEQ ID NO 81
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 81
attctgtcca gacgacgaca ataaacaaca tgttcagcta atgcagaacg cgcctgttta    60

<210> SEQ ID NO 82
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 82
tcaacaatag ataagtcctg aacaagaaaa ataatatccc atcctaattt acgagcatgt    60

<210> SEQ ID NO 83
<211> LENGTH: 60
<212> TYPE: DNA
<213> ORGANISM: Artificial Sequence
<220> FEATURE:

<223> OTHER INFORMATION: single strand nucleic acid scaffold

<400> SEQUENCE: 83
agaaaccaat caataatcgg ctgtctttcc ttatcattcc aagaacgggt attaaaccaa    60

<210> SEQ ID NO 84
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 84
gtaccgcact catcgagaac aagcaagccg tttttatttt catcgtagga atcattaccg    60

<210> SEQ ID NO 85
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 85
cgcccaatag caagcaaatc agatatagaa ggcttatccg gtattctaag aacgcgaggc    60

<210> SEQ ID NO 86
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 86
attttgcacc cagctacaat tttatcctga atcttaccaa cgctaacgag cgtctttcca    60

<210> SEQ ID NO 87
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 87
gagcctaatt tgccagttac aaaataaaca gccatattat ttatcccaat ccaaataaga    60

<210> SEQ ID NO 88
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 88
aacgattttt tgtttaacgt caaaaatgaa aatagcagcc tttacagaga gaataacata    60

<210> SEQ ID NO 89
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 89
aaaacaggga agcgcattag acgggagaat taactgaaca ccctgaacaa agtcagaggg    60

```
<210> SEQ ID NO 90
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 90
taattgagcg ctaatatcag agagataacc cacaagaatt gagttaagcc caataataag    60

<210> SEQ ID NO 91
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 91
agcaagaaac aatgaaatag caatagctat cttaccgaag ccctttttaa gaaaagtaag    60

<210> SEQ ID NO 92
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 92
cagatagccg aacaaagtta ccagaaggaa accgaggaaa cgcaataata acggaatacc    60

<210> SEQ ID NO 93
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 93
caaaagaact ggcatgatta agactcctta ttacgcagta tgttagcaaa cgtagaaaat    60

<210> SEQ ID NO 94
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 94
acatacataa aggtggcaac atataaaaga aacgcaaaga caccacggaa taagtttatt    60

<210> SEQ ID NO 95
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 95
ttgtcacaat caatagaaaa ttcatatggt ttaccagcgc caaagacaaa agggcgacat    60

<210> SEQ ID NO 96
<211> LENGTH: 60
<212> TYPE: DNA
<213> ORGANISM: Artificial Sequence
<220> FEATURE:
<223> OTHER INFORMATION: single strand nucleic acid scaffold
```

```
<400> SEQUENCE: 96
tcaccgtcac cgacttgagc catttgggaa ttagagccag caaaatcacc agtagcacca      60

<210> SEQ ID NO 97
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 97
ttaccattag caaggccgga aacgtcacca atgaaaccat cgatagcagc accgtaatca      60

<210> SEQ ID NO 98
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 98
gtagcgacag aatcaagttt gcctttagcg tcagactgta gcgcgttttc atcggcattt      60

<210> SEQ ID NO 99
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 99
tcggtcatag ccccttatt agcgtttgcc atcttttcat aatcaaaatc accggaacca      60

<210> SEQ ID NO 100
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 100
gagccaccac cggaaccgcc tccctcagag ccgccaccct cagaaccgcc accctcagag      60

<210> SEQ ID NO 101
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 101
ccaccaccct cagagccgcc accagaacca ccaccagagc cgccgccagc attgacagga      60

<210> SEQ ID NO 102
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 102
ggttgaggca ggtcagacga ttggccttga tattcacaaa caaataaatc ctcattaaag      60

<210> SEQ ID NO 103
<211> LENGTH: 60
```

```
<212> TYPE: DNA
<213> ORGANISM: Artificial Sequence
<220> FEATURE:
<223> OTHER INFORMATION: single strand nucleic acid scaffold

<400> SEQUENCE: 103
ccagaatgga aagcgcagtc tctgaattta ccgttccagt aagcgtcata catggctttt      60

<210> SEQ ID NO 104
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 104
gatgatacag gagtgtactg gtaataagtt ttaacggggt cagtgccttg agtaacagtg      60

<210> SEQ ID NO 105
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 105
cccgtataaa cagttaatgc ccctgccta tttcggaacc tattattctg aaacatgaaa       60

<210> SEQ ID NO 106
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 106
ccaggcggat aagtgccgtc gagagggttg atataagtat agcccggaat aggtgtatca      60

<210> SEQ ID NO 107
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 107
ccgtactcag gaggtttagt accgccaccc tcagaaccgc caccctcaga accgccaccc      60

<210> SEQ ID NO 108
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 108
tcagagccac caccctcatt ttcagggata gcaagcccaa taggaaccca tgtaccgtaa      60

<210> SEQ ID NO 109
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 109
```
cactgagttt cgtcaccagt acaaactaca acgcctgtag cattccacag acagccctca    60

<210> SEQ ID NO 110
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 110
tagttagcgt aacgatctaa agttttgtcg tctttccaga cgttagtaaa tgaattttct    60

<210> SEQ ID NO 111
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 111
gtatgggatt ttgctaaaca actttcaaca gtttcagcgg agtgagaata gaaaggaaca    60

<210> SEQ ID NO 112
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 112
actaaaggaa ttgcgaataa taatttttc acgttgaaaa tctccaaaaa aaaggctcca    60

<210> SEQ ID NO 113
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 113
aaaggagcct ttaattgtat cggtttatca gcttgctttc gaggtgaatt tcttaaacag    60

<210> SEQ ID NO 114
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 114
cttgataccg atagttgcgc cgacaatgac aacaaccatc gcccacgcat aaccgatata    60

<210> SEQ ID NO 115
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 115
ttcggtcgct gaggcttgca gggagttaaa ggccgctttt gcgggatcgt caccctcagc    60

<210> SEQ ID NO 116
<211> LENGTH: 60
<212> TYPE: DNA
<213> ORGANISM: Artificial Sequence

```
<220> FEATURE:
<223> OTHER INFORMATION: single strand nucleic acid scaffold

<400> SEQUENCE: 116 cttttcatg aggaagtttc cattaaacgg gtaaaatacg taatgccact acgaaggcac    60

<210> SEQ ID NO 117
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 117
caacctaaaa cgaaagaggc aaaagaatac actaaaacac tcatctttga ccccagcga    60

<210> SEQ ID NO 118
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 118
ttataccaag cgcgaaacaa agtacaacgg agatttgtat catcgcctga taaattgtgt    60

<210> SEQ ID NO 119
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 119
cgaaatccgc gacctgctcc atgttactta gccggaacga ggcgcagacg gtcaatcata    60

<210> SEQ ID NO 120
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 120
agggaaccga actgaccaac tttgaaagag gacagatgaa cggtgtacag accaggcgca    60

<210> SEQ ID NO 121
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 121
taggctggct gaccttcatc aagagtaatc ttgacaagaa ccggatattc attacccaaa    60

<210> SEQ ID NO 122
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 122
tcaacgtaac aaagctgctc attcagtgaa taaggcttgc cctgacgaga aacaccagaa    60
```

```
<210> SEQ ID NO 123
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 123
cgagtagtaa attgggcttg agatggttta atttcaactt taatcattgt gaattaccttt    60

<210> SEQ ID NO 124
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 124
atgcgatttt aagaactggc tcattatacc agtcaggacg ttgggaagaa aaatctacgt    60

<210> SEQ ID NO 125
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 125
taataaaacg aactaacgga acaacattat tacaggtaga agattcatc agttgagatt    60

<210> SEQ ID NO 126
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 126
taagagcaac actatcataa ccctcgttta ccagacgacg ataaaaacca aaatagcgag    60

<210> SEQ ID NO 127
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 127
aggcttttgc aaaagaagtt ttgccagagg gggtaatagt aaaatgttta gactggatag    60

<210> SEQ ID NO 128
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 128
cgtccaatac tgcggaatcg tcataaatat tcattgaatc ccctcaaat gctttaaaca    60

<210> SEQ ID NO 129
<211> LENGTH: 60
<212> TYPE: DNA
<213> ORGANISM: Artificial Sequence
<220> FEATURE:
<223> OTHER INFORMATION: single strand nucleic acid scaffold
```

<400> SEQUENCE: 129
gttcagaaaa cgagaatgac cataaatcaa aaatcaggtc tttaccctga ctattatagt    60

<210> SEQ ID NO 130
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 130
cagaagcaaa gcggattgca tcaaaaagat taagaggaag cccgaaagac ttcaaatatc    60

<210> SEQ ID NO 131
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 131
gcgttttaat tcgagcttca aagcgaacca gaccggaagc aaactccaac aggtcaggat    60

<210> SEQ ID NO 132
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 132
tagagagtac ctttaattgc tcctttgat aagaggtcat ttttgcggat ggcttagagc    60

<210> SEQ ID NO 133
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 133
ttaattgctg aatataatgc tgtagctcaa catgttttaa atatgcaact aaagtacggt    60

<210> SEQ ID NO 134
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 134
gtctggaagt ttcattccat ataacagttg attcccaatt ctgcgaacga gtagatttag    60

<210> SEQ ID NO 135
<211> LENGTH: 49
<212> TYPE: DNA
<213> ORGANISM: Artificial Sequence
<220> FEATURE:
<223> OTHER INFORMATION: single strand nucleic acid scaffold

<400> SEQUENCE: 135
tttgaccatt agatacattt cgcaaatggt caataacctg tttagctat    49

<210> SEQ ID NO 136

```
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 136
aacatccaat aaatcataca ggcaaggcaa agaattagca aaattaagca ataaagcctc      60

<210> SEQ ID NO 137
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 137
gtgagcgagt aacaacccgt cggattctcc gtgggaacaa acggcggatt gaccgtaatg      60

<210> SEQ ID NO 138
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 138
ttcttttcac cagtgagacg ggcaacagct gattgccctt caccgcctgg ccctgagaga      60

<210> SEQ ID NO 139
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 139
tctgtccatc acgcaaatta accgttgtag caatacttct ttgattagta ataacatcac      60

<210> SEQ ID NO 140
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 140
attcgacaac tcgtattaaa tcctttgccc gaacgttatt aattttaaaa gtttgagtaa      60

<210> SEQ ID NO 141
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 141
tgggttatat aactatatgt aaatgctgat gcaaatccaa tcgcaagaca aagaacgcga      60

<210> SEQ ID NO 142
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 142
```

```
gttttagcga acctcccgac ttgcgggagg ttttgaagcc ttaaatcaag attagttgct    60

<210> SEQ ID NO 143
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 143
tcaaccgatt gagggaggga aggtaaatat tgacggaaat tattcattaa aggtgaatta    60

<210> SEQ ID NO 144
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 144
gtattaagag gctgagactc ctcaagagaa ggattaggat tagcggggtt ttgctcagta    60

<210> SEQ ID NO 145
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 145
agcgaaagac agcatcggaa cgagggtagc aacggctaca gaggctttga ggactaaaga    60

<210> SEQ ID NO 146
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 146
taggaatacc acattcaact aatgcagata cataacgcca aaaggaatta cgaggcatag    60

<210> SEQ ID NO 147
<211> LENGTH: 60
<212> TYPE: DNA
<213> ORGANISM: Artificial Sequence
<220> FEATURE:
<223> OTHER INFORMATION: single strand nucleic acid scaffold

<400> SEQUENCE: 147
attttcattt ggggcgcgag ctgaaaaggt ggcatcaatt ctactaatag tagtagcatt    60
```